United States Patent
Khurana et al.

(10) Patent No.: US 11,028,389 B2
(45) Date of Patent: Jun. 8, 2021

(54) METHODS FOR ENHANCING UTROPHIN PRODUCTION VIA INHIBITION OF MICRORNA

(71) Applicants: THE TRUSTEES OF THE UNIVERSITY OF PENNSYLVANIA, Philadelphia, PA (US); Murdoch University, Murdoch (AU)

(72) Inventors: Tejvir S. Khurana, Narberth, PA (US); Steve Wilton, Applecross (AU)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 16/319,355

(22) PCT Filed: Jul. 19, 2017

(86) PCT No.: PCT/US2017/042862
§ 371 (c)(1),
(2) Date: Jan. 21, 2019

(87) PCT Pub. No.: WO2018/017719
PCT Pub. Date: Jan. 25, 2018

(65) Prior Publication Data
US 2019/0300879 A1  Oct. 3, 2019

Related U.S. Application Data

(60) Provisional application No. 62/364,207, filed on Jul. 19, 2016.

(51) Int. Cl.
*C07H 21/04* (2006.01)
*C07H 21/02* (2006.01)
*C12N 15/113* (2010.01)
*A61P 21/00* (2006.01)
*A61K 31/7088* (2006.01)

(52) U.S. Cl.
CPC ........ *C12N 15/113* (2013.01); *A61K 31/7088* (2013.01); *A61P 21/00* (2018.01); *C12N 2310/113* (2013.01); *C12N 2310/314* (2013.01); *C12N 2310/315* (2013.01); *C12N 2310/321* (2013.01); *C12N 2310/3233* (2013.01); *C12N 2320/32* (2013.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 2011/0117111 A1 | 5/2011 | Kwon et al. |
| 2012/0122953 A1 | 5/2012 | Moorwood et al. |
| 2015/0099791 A1 | 4/2015 | Krieg et al. |
| 2016/0046931 A1 | 2/2016 | Moorwood et al. |

OTHER PUBLICATIONS

Basu et al. (PLoS One, 2011, 6(12):e29376, pp. 1-9).*

* cited by examiner

*Primary Examiner* — Amy H Bowman
(74) *Attorney, Agent, or Firm* — Mark S. Cohen; Pearl Cohen Zedek Latzer Baratz LLP

(57) ABSTRACT

This invention provides a method for enhancing utrophin protein production in a cell by inhibiting an utrophin microRNA molecule. Moreover, the invention provides that methods for enhancing utrophin protein production in a muscle cell are used for treating a muscular dystrophy and/or other myopathies.

6 Claims, 51 Drawing Sheets
Specification includes a Sequence Listing.

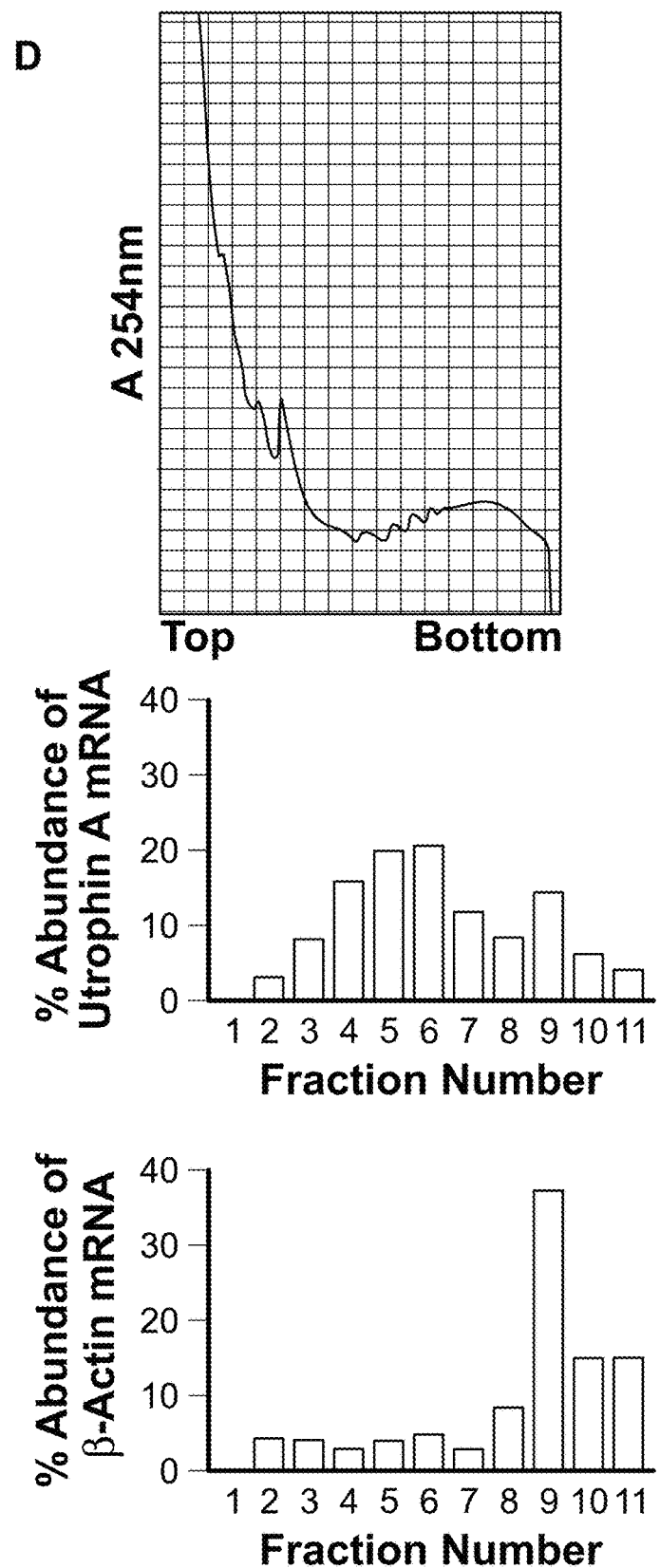
FIG. 1(cont..)

miRNAs Targeting Utrn-A 3'UTR

- Several miRNA Candidates were Predicted to Target Utrn-A Using miRamda v1.0b Algorithm
- Expression Confirmed in C2C12 Cells or TA by Taqman microRNA Assay

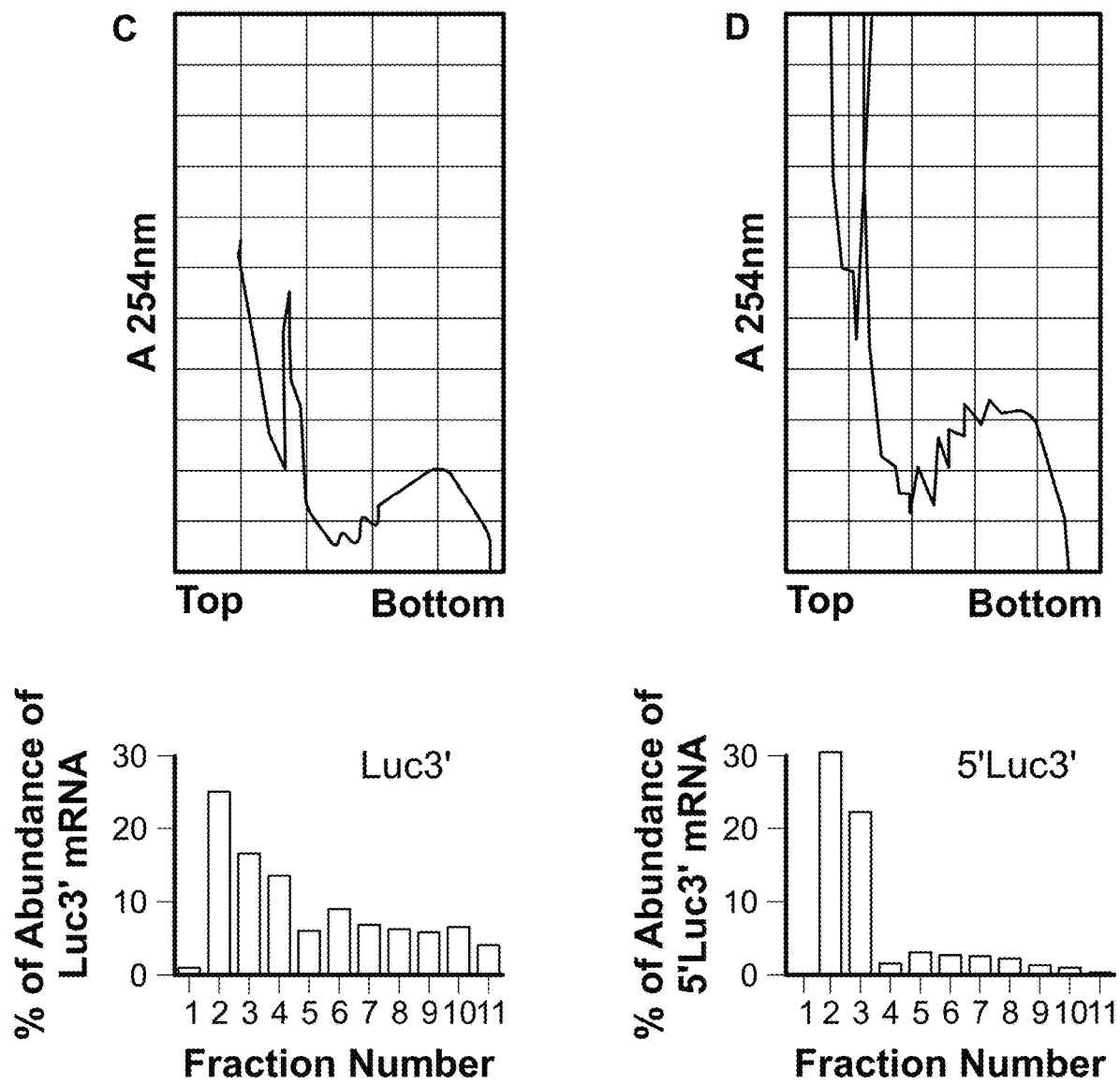
FIG. 10(Cont..)

A
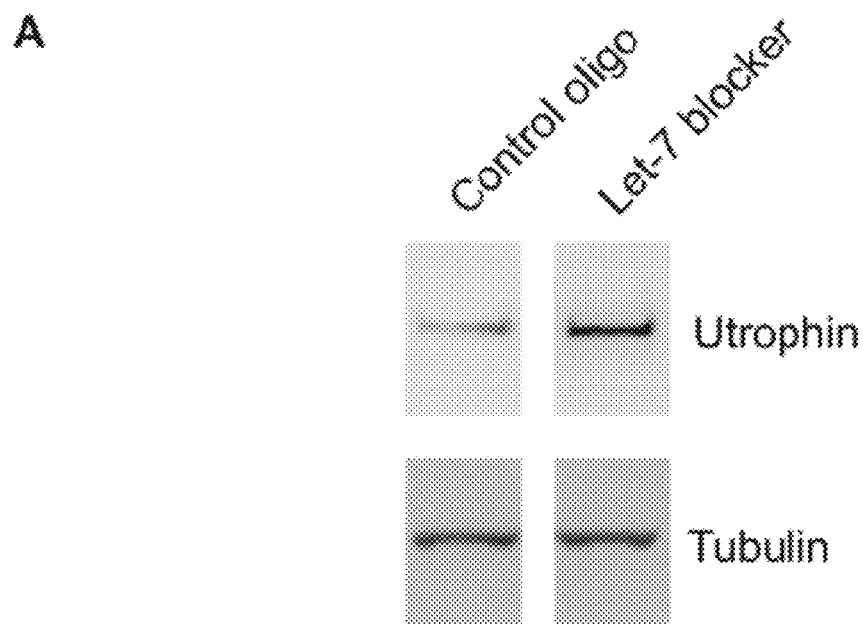
B
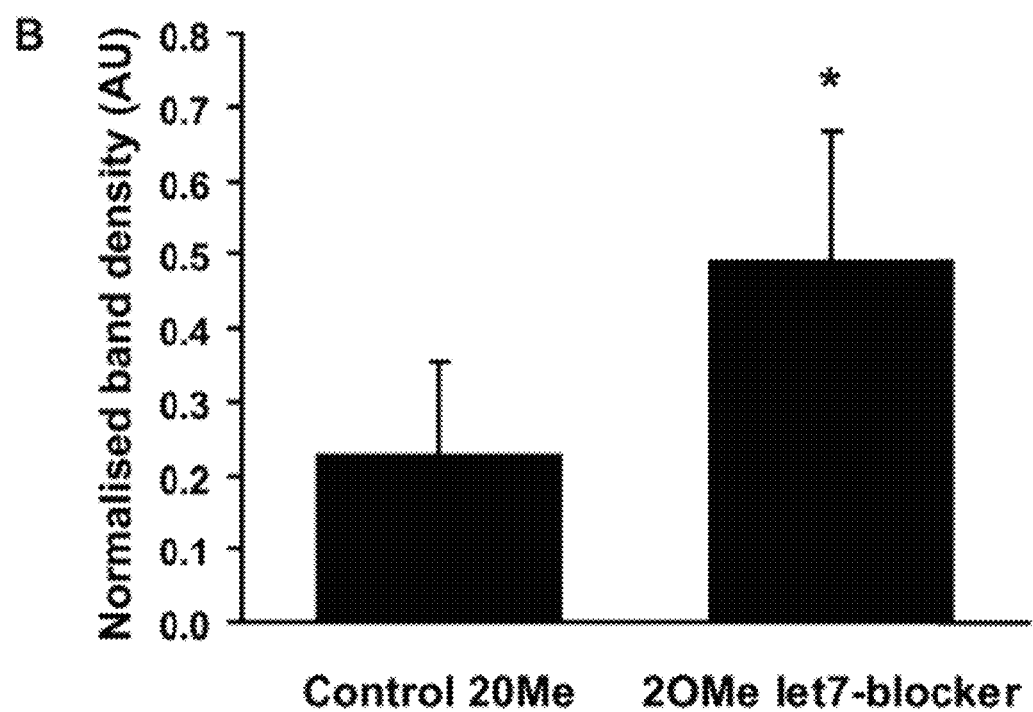
FIGURE 19

| | Oligos | Name | Oligo Sequence (5'→ 3') |
|---|---|---|---|
| 1 | let7 | Let7 blocker | 5'-CUG AGG UAG AAA GGU GAU CAU GGC UC-3' |
| 2 | Control | Rat SMN1 | 5'-GUG AGC ACU UCU UUC CUU CUU UUU U-3' |

Sequence of let7 binding site in mouse/human Utrn 3'UTR (partial SEQ): (let7 binding site is in caps with flanking region)

Mouse 3'UTR :   5'- aggggagAGCCATGATCACCTTTCTACCTCAgaaccac -3'

Human 3'UTR :   5'- aaaggaaAGCCATGACCACCTTTCTACCTCAgatccat -3'

FIGURE 20

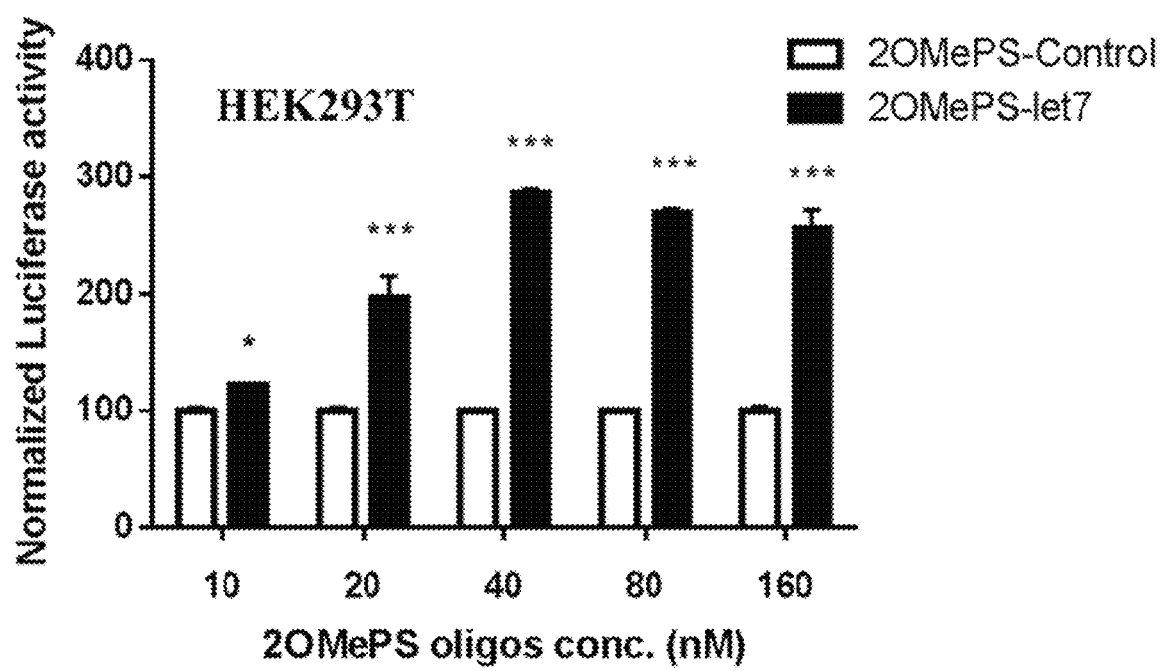

FIGURE 21

Percentage of centrally nucleated fibers (CNFs) in TA muscle
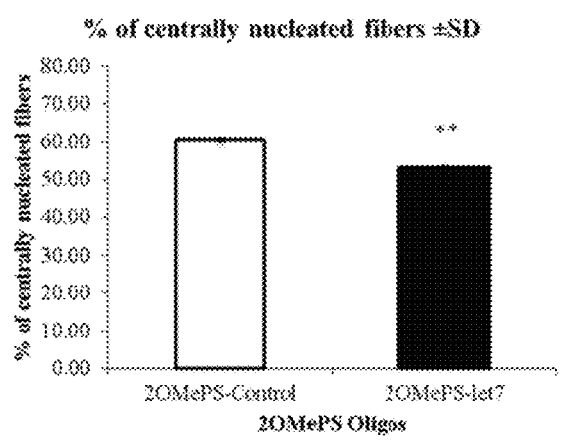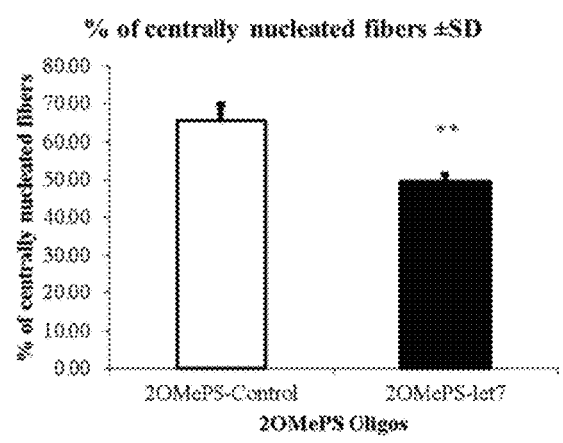
FIGURE 30

Minimum feret diameter of EDL muscle fibers
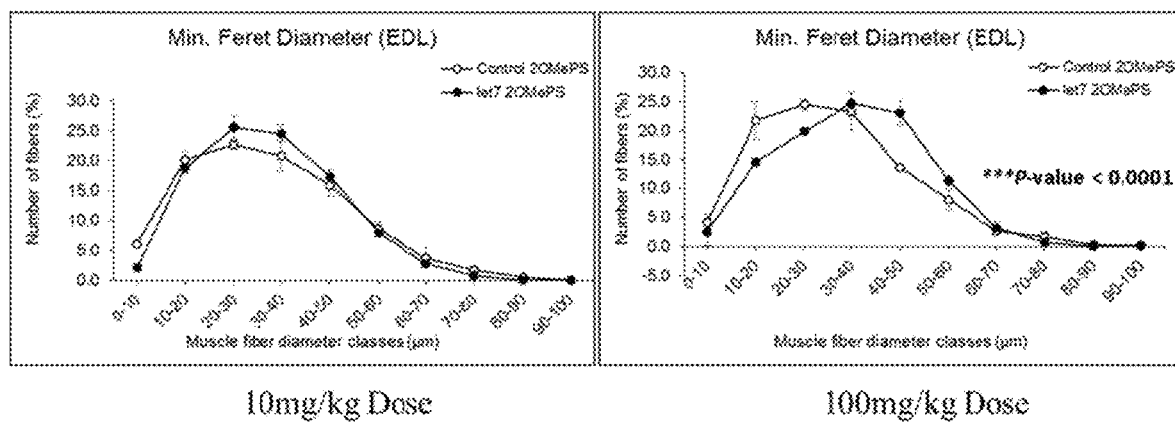
FIGURE 35
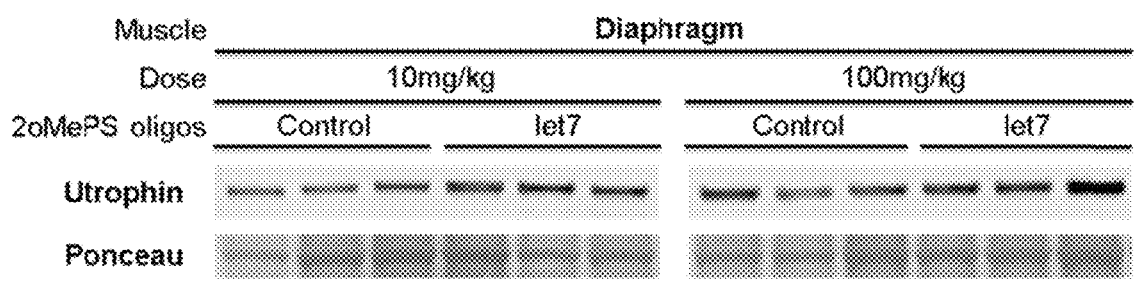
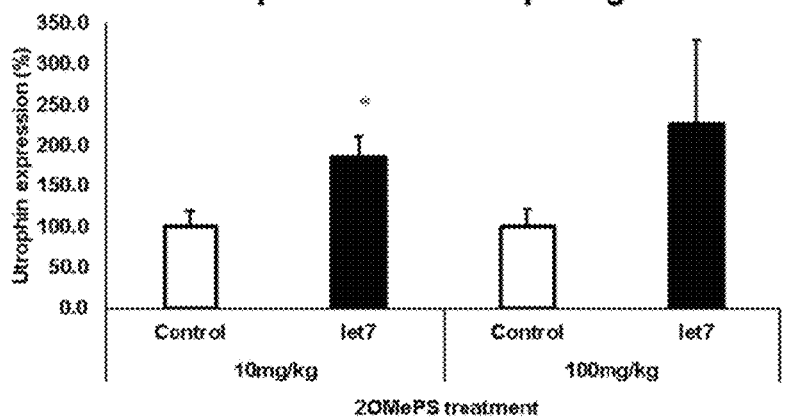
FIGURE 36

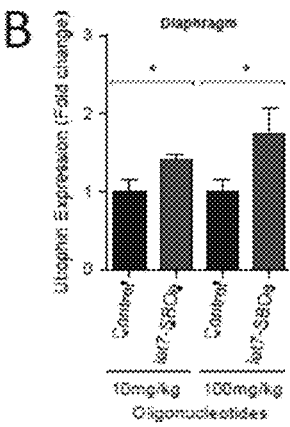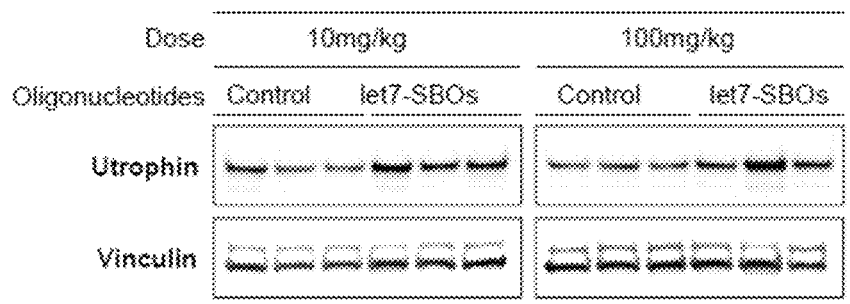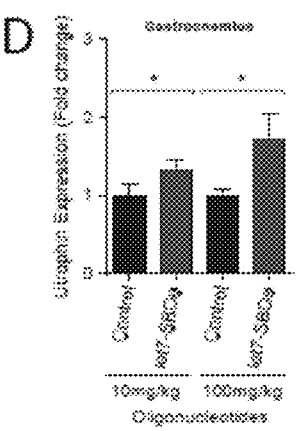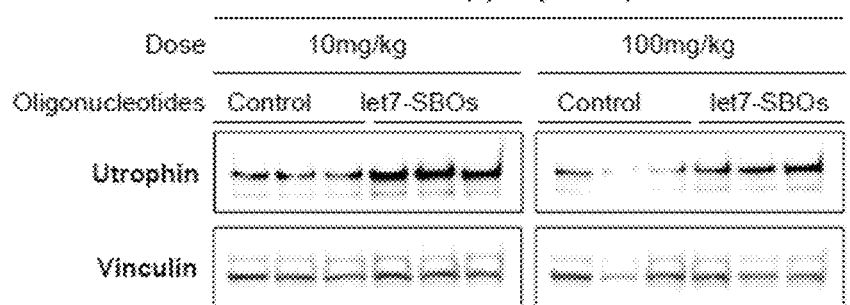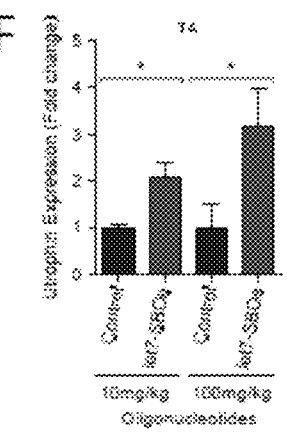
FIGURE 46

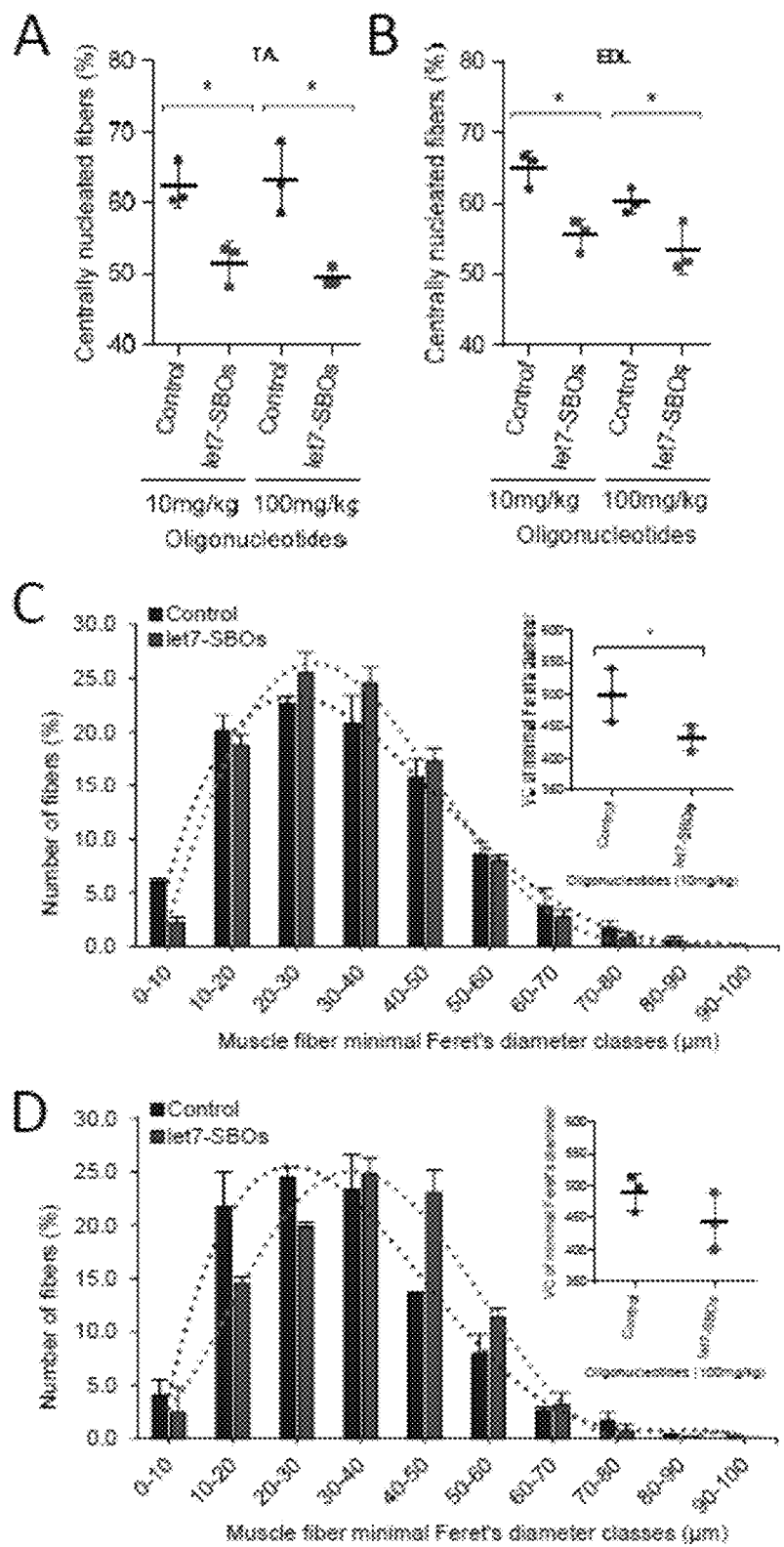
FIGURE 48A-D

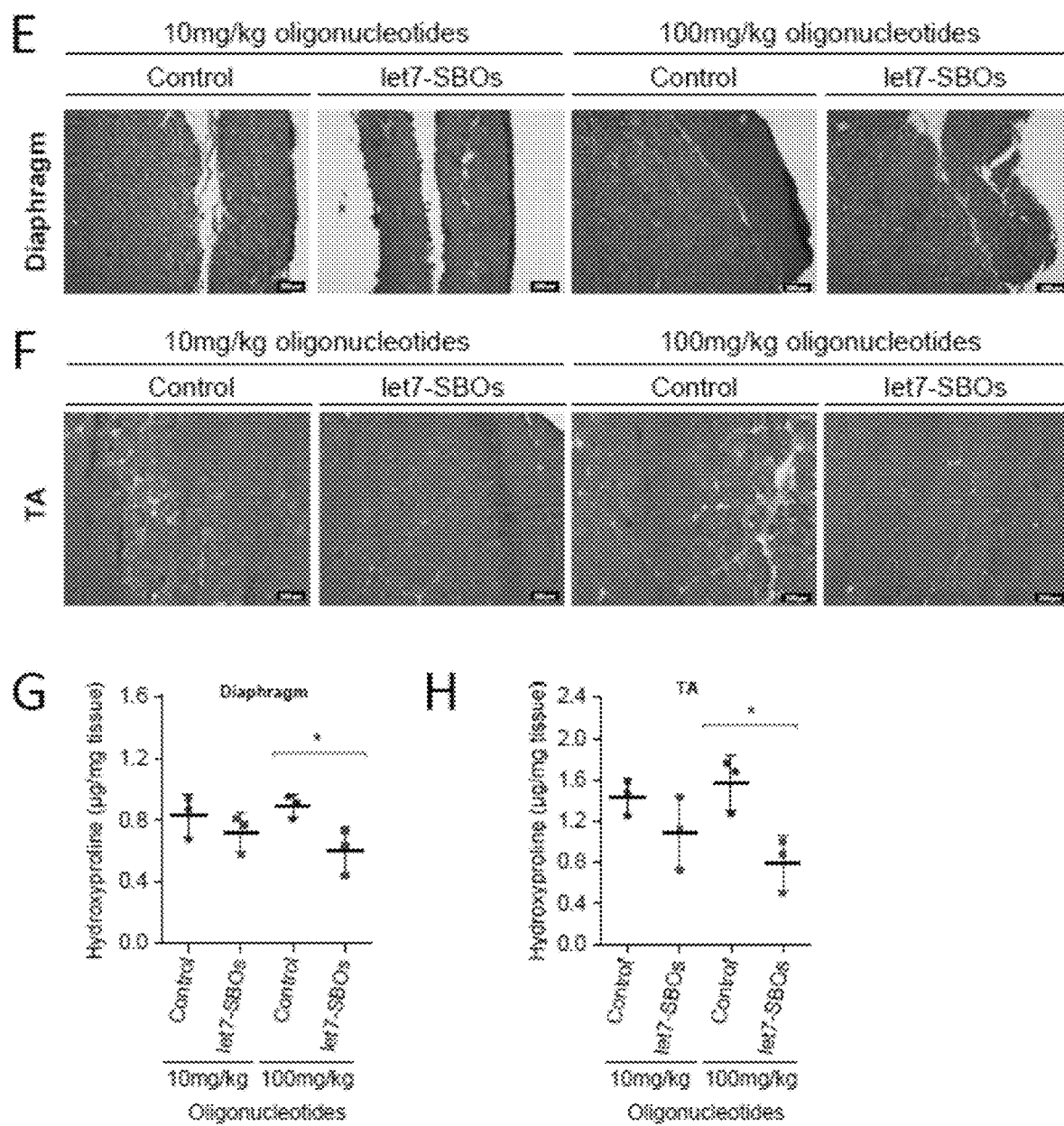
FIGURE 48E-G

A
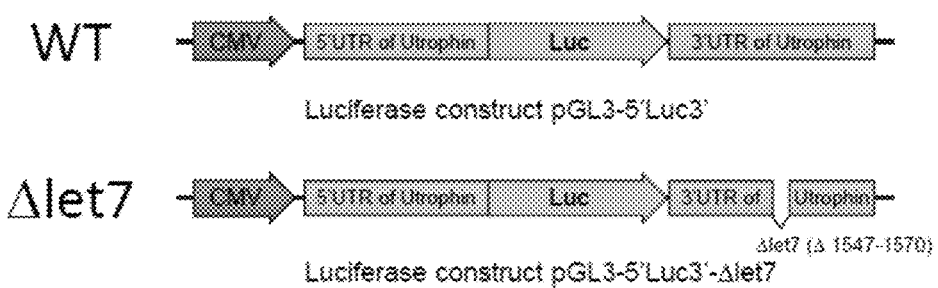
B
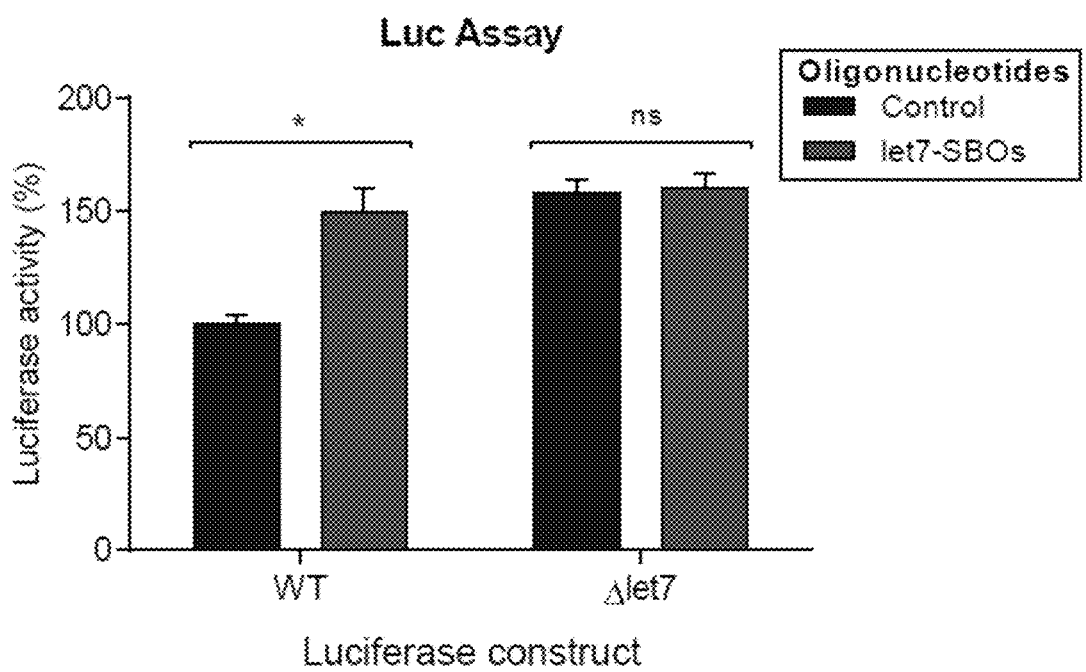
FIGURE 51

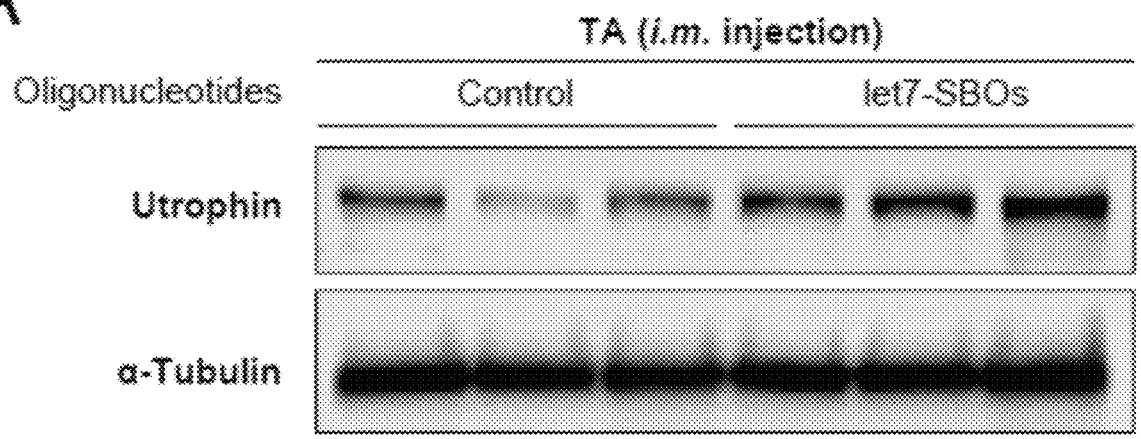
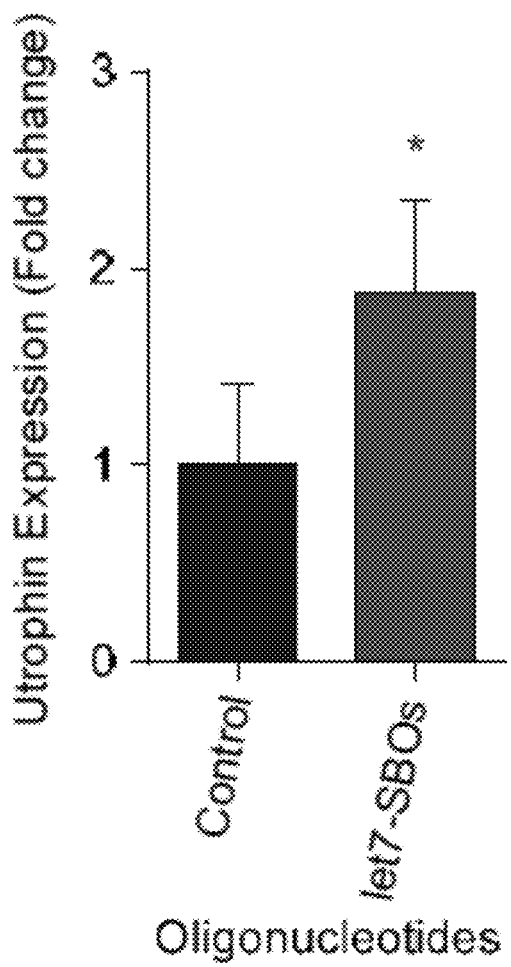
FIGURE 52

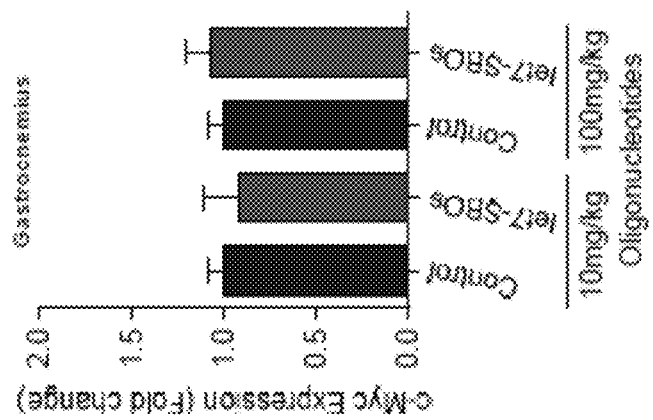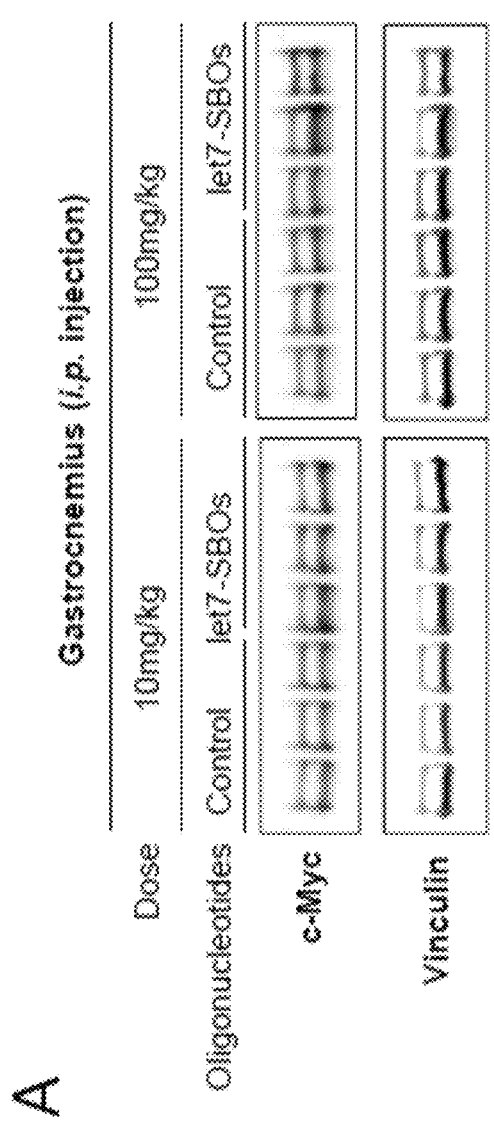
FIGURE 56A-B

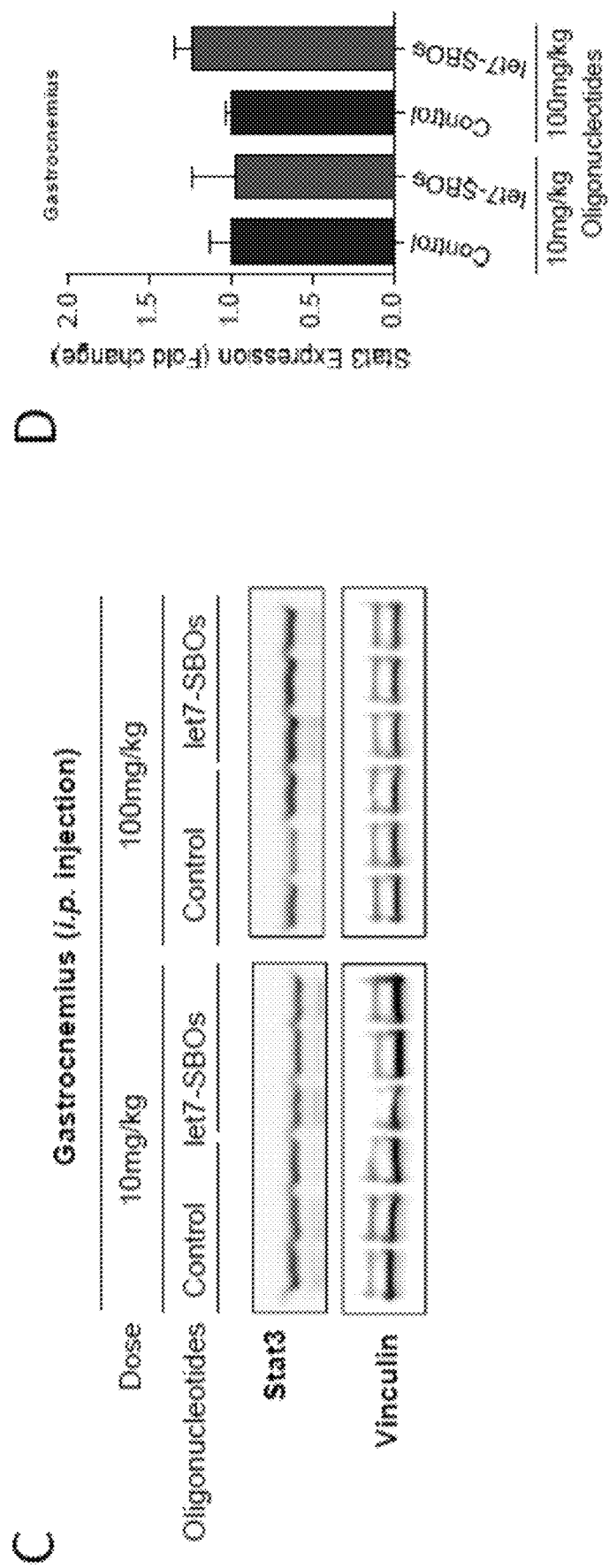
FIGURE 56C-D

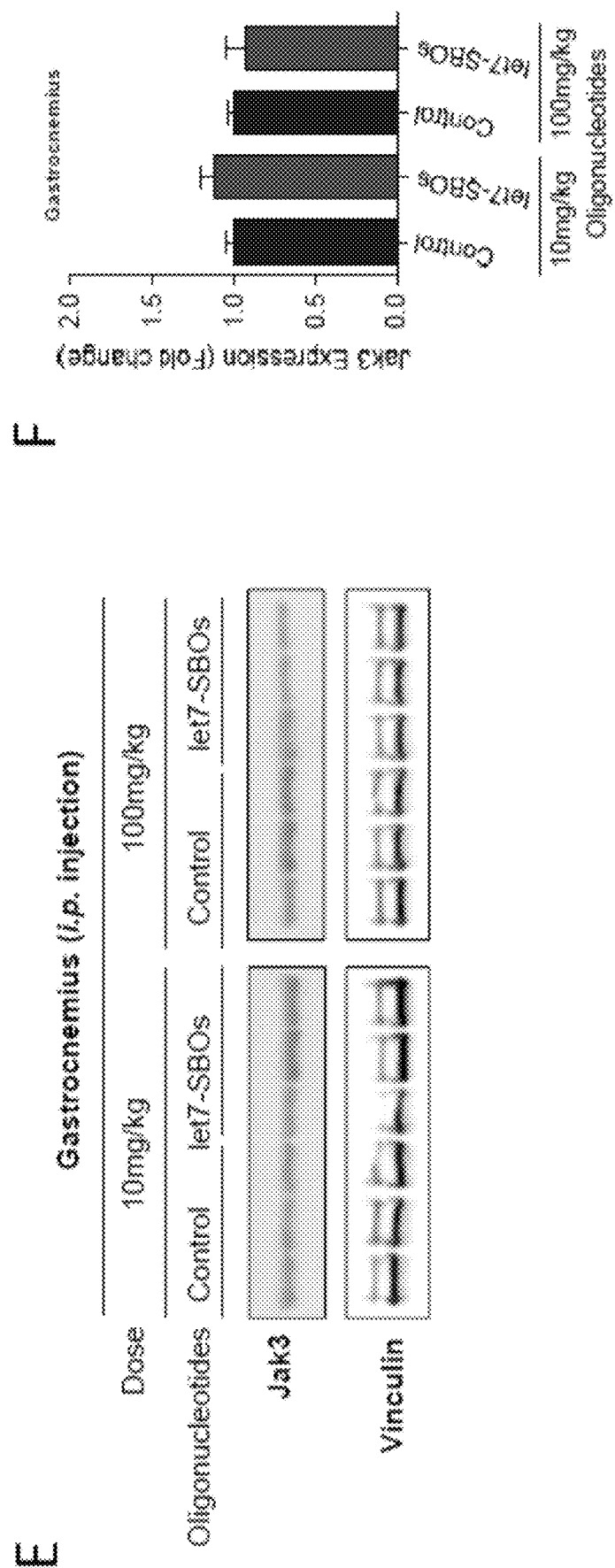
FIGURE 56E-F

```
                              SEQUENCE LISTING

<160> NUMBER OF SEQ ID NOS: 89

<210> SEQ ID NO 1
<211> LENGTH: 22
<212> TYPE: RNA
<213> ORGANISM: Homo sapiens

<400> SEQUENCE: 1
ugagguagua gguuguaugg uu                                                  22

<210> SEQ ID NO 2
<211> LENGTH: 22
<212> TYPE: RNA
<213> ORGANISM: Homo sapiens

<400> SEQUENCE: 2
aaccauacaa ccuacuaccu ca                                                  22

<210> SEQ ID NO 3
<211> LENGTH: 22
<212> TYPE: RNA
<213> ORGANISM: Homo sapiens

<400> SEQUENCE: 3
uuuggucccc uucaaccagc ua                                                  22

<210> SEQ ID NO 4
<211> LENGTH: 21
<212> TYPE: RNA
<213> ORGANISM: Homo sapiens

<400> SEQUENCE: 4
uagcugguug aaggggacca a                                                   21

<210> SEQ ID NO 5
<211> LENGTH: 22
<212> TYPE: RNA
<213> ORGANISM: Homo sapiens

<400> SEQUENCE: 5
ucucccaacc cuuguaccag ug                                                  22

<210> SEQ ID NO 6
<211> LENGTH: 22
<212> TYPE: RNA
<213> ORGANISM: Homo sapiens

<400> SEQUENCE: 6
cacugguaca aggguuggga ga                                                  22

<210> SEQ ID NO 7
<211> LENGTH: 22
<212> TYPE: RNA
<213> ORGANISM: Homo sapiens

<400> SEQUENCE: 7
uagguaguuu ccuguuguug gg                                                  22
```

```
<210> SEQ ID NO 8
<211> LENGTH: 21
<212> TYPE: RNA
<213> ORGANISM: Homo sapiens

<400> SEQUENCE: 8
ccaacaacag gaaacuaccu a                                              21

<210> SEQ ID NO 9
<211> LENGTH: 22
<212> TYPE: RNA
<213> ORGANISM: Homo sapiens

<400> SEQUENCE: 9
uggaauguaa ggaagugugu gg                                             22

<210> SEQ ID NO 10
<211> LENGTH: 22
<212> TYPE: RNA
<213> ORGANISM: Homo sapiens

<400> SEQUENCE: 10
ccacacacuu ccuuacauuc ca                                             22

<210> SEQ ID NO 11
<211> LENGTH: 21
<212> TYPE: RNA
<213> ORGANISM: Homo sapiens

<400> SEQUENCE: 11
agggcccccc cucaauccug u                                              21

<210> SEQ ID NO 12
<211> LENGTH: 21
<212> TYPE: RNA
<213> ORGANISM: Homo sapiens

<400> SEQUENCE: 12
acaggauuga gggggggccc u                                              21

<210> SEQ ID NO 13
<211> LENGTH: 2391
<212> TYPE: DNA
<213> ORGANISM: Mus musculus

<400> SEQUENCE: 13
tgagcatcta tccagccagc caacatttcc cgaccttcag tattgccctc ttctgcaaat    60
gccaatccca agacccattc aaccccaaag ctccgtggct ccacgacaca agctgttgag   120
tgcttactgg gtgttctact gagggaacca acactgact  atccaaagag aaaaggatat   180
tttggttttc taataacgta tattattgtt ttcttctccc ctttctatgc aactgtaaat   240
taatgaacag agaagtattt ggaggtggta aagcatttgt cactgatttg tataatatat   300
acagccatgg gaaagtgggt gggggctttc taatatgaaa ctgtcttttt aataaccaag   360
agaaaaaatt gcataagaat tagaccactt tacattatta cattccttct gctgttcaca   420
ttaaccttgt acaataactt cacttattat ttgactgttt taccattatg ttttggttat   480
ttataaattt atcagccata caaacaaata gattctatgt atttgtttct ataatctggc   540
caaattccta agttcatata tttgaatcaa atattttaca tatgtggagt aggcaggcat   600
```

-continued

```
tctgaagata ctatttaact ttagttgacg tcacacacac catcctttag taaccactgg      660
atgactacac taaaaatcct gtggacttta acggcaagct gctggggtat ttttcctcct      720 gttttttattc cttttttgta agtagatctt gacgtcttta tttatttcat cttgcaatct    780
ctataataaa gaagactgta ttgtaatagt ctcaaaaaat tatttaccagtta agggttacca   840 tttaagcata ttttcatttt gattcagaaa ccaaagttgg tacaacctct cctagtacat     900
gcaaccttgg ttttcatgag aaaacacacg gcaggccttt gcccattgtg aggagagcac     960
acatcatgct cttcagtttc ctttgaatag acttttattg ttgttttttgt attttcgag     1020 tcctgtgtaa gttttgaaag ctctggttgt ttcctttgtg aaagcaggca gatacttagt     1080
tggctgtctc atttgaagct ttggagcaga tagtcagatg tctcatgacc cctcacttgg     1140
ccagcagcac atccgagaag gatgtcactc acaagcctac accacggctt ctctagaatg    1200
aaatcagtgc tcggatgatt gtatccctgc ctctacttct gagtgtgttc aactaggtat     1260
tggcttcttt ttctttttct tttctttttt ttttaattta acacttaatt gccgatttta    1320
gagaaaccaa aaataaaggt gaaggtaata tgttttgatt caaacatata tgcttttaaa    1380
catcagacat gctaactttg gttctcttta ctggaatctg gcccagagga ggtgaaattt     1440
agaaatgtta ttctttagat gggtgggtgg gttggggggc caagggtgtc tattttccag    1500
cattagatat ttttgagacg aagaaaattg ttttatataa ggggagagcc atgatcacct    1560
ttctacctca gaaccacctt cctccattgt gttggacata gctttatatg ccgcagtgtg    1620
caaaacctag ggctgtagtc aggccttttcc atacccagga agcacctgtg taaagaagat    1680
caacagaaac tcccggaact cagaaccccca agttgtagat tggtgtcgt ccttgttctt     1740 gctttgagga gtcatgtatt cttttatttc ctgcctgtat ttgtatgcaa aatgatctct    1800
atctgctatt acagaaaaag ctacacaaaa cactacattg taaccttctg agtaataaat    1860
aagaggaaat atattacagt aaccatgatg agaaataagt gtattgttct tttgaaatat    1920
gtggttaatc gcagactgtc atctaatctg ttacataccg tattttttcat cctgaataaa   1980 agtaatttta acacaaaatg actttgatgt ttggctgtgt tcagctgatg aaatcagatc    2040
tctgaatgta tgtgatgaaa gctaactata agatgatcta tattctgata aatctaaata   2100
ttttctgaaa ctctctctta tacattaatc tagtctccat tcactcatta tctctctctc    2160
ctttcttgca tataaatatg attatatatt tttcaatttc ctgtacaaat cagagtctta    2220
ttactaggga aaatggatgt tataagtaca ttcctaaagc ccattgggcc ttcattttta    2280
taacttggag ctactgagat ttatcaggtt actctctcaa atccactttc atcactagac    2340
tcatagtttt ctatgtatct atattattat aactaaataa aaatatacat g             2391
```

<210> SEQ ID NO 14
<211> LENGTH: 23
<212> TYPE: DNA
<213> ORGANISM: Homo sapiens

<400> SEQUENCE: 14

```
atgggaaagt gggtgggggc ttt                                              23
```

<210> SEQ ID NO 15
<211> LENGTH: 22
<212> TYPE: DNA
<213> ORGANISM: Homo sapiens

<400> SEQUENCE: 15

```
ccactttaca ttattacatt cc                                               22
```

<210> SEQ ID NO 16
<211> LENGTH: 20
<212> TYPE: DNA
<213> ORGANISM: Homo sapiens

<400> SEQUENCE: 16
atgggtgggt gggttggggg                                              20

<210> SEQ ID NO 17
<211> LENGTH: 17
<212> TYPE: DNA
<213> ORGANISM: Homo sapiens

<400> SEQUENCE: 17
gtgggttggg gggccaa                                                 17

<210> SEQ ID NO 18
<211> LENGTH: 24
<212> TYPE: DNA
<213> ORGANISM: Mus musculus

<400> SEQUENCE: 18
agccatgatc acctttctac ctca                                         24

<210> SEQ ID NO 19
<211> LENGTH: 19
<212> TYPE: DNA
<213> ORGANISM: Homo sapiens

<400> SEQUENCE: 19
ccatacccag gaagcacct                                               19

<210> SEQ ID NO 20
<211> LENGTH: 21
<212> TYPE: RNA
<213> ORGANISM: Homo sapiens

<400> SEQUENCE: 20
aaguggauau uguugccauc a                                            21

<210> SEQ ID NO 21
<211> LENGTH: 21
<212> TYPE: DNA
<213> ORGANISM: Homo sapiens

<400> SEQUENCE: 21
aguacugcuu acgauacggt t                                            21

<210> SEQ ID NO 22
<211> LENGTH: 21
<212> TYPE: DNA
<213> ORGANISM: Homo sapiens

<400> SEQUENCE: 22
ccguaucgua agcaguacut t                                            21

<210> SEQ ID NO 23
<211> LENGTH: 21
<212> TYPE: DNA
<213> ORGANISM: Homo sapiens

<400> SEQUENCE: 23

```
gggtgggtgg gttgggggc c                                          21
```

<210> SEQ ID NO 24
<211> LENGTH: 26
<212> TYPE: RNA
<213> ORGANISM: Mus musculus

<400> SEQUENCE: 24

```
cugagguaga aaggugauca uggcuc                                    26
```

<210> SEQ ID NO 25
<211> LENGTH: 26
<212> TYPE: RNA
<213> ORGANISM: Homo sapiens

<400> SEQUENCE: 25

```
cugagguaga aaggugguca uggcuu                                    26
```

<210> SEQ ID NO 26
<211> LENGTH: 27
<212> TYPE: RNA
<213> ORGANISM: Mus musculus

<400> SEQUENCE: 26

```
cugagguaga aaggugauca uggcucu                                   27
```

<210> SEQ ID NO 27
<211> LENGTH: 28
<212> TYPE: RNA
<213> ORGANISM: Mus musculus

<400> SEQUENCE: 27

```
cugagguaga aaggugauca uggcucuc                                  28
```

<210> SEQ ID NO 28
<211> LENGTH: 29
<212> TYPE: RNA
<213> ORGANISM: Mus musculus

<400> SEQUENCE: 28

```
cugagguaga aaggugauca uggcucucc                                 29
```

<210> SEQ ID NO 29
<211> LENGTH: 27
<212> TYPE: RNA
<213> ORGANISM: Mus musculus

<400> SEQUENCE: 29

```
ucugagguag aaaggugauc auggcuc                                   27
```

<210> SEQ ID NO 30
<211> LENGTH: 28
<212> TYPE: RNA
<213> ORGANISM: Mus musculus

<400> SEQUENCE: 30

```
uucugaggua gaaaggugau cauggcuc                                  28
```

<210> SEQ ID NO 31
<211> LENGTH: 29
<212> TYPE: RNA
<213> ORGANISM: Mus musculus

<400> SEQUENCE: 31

```
guucugaggu agaaagguga ucauggcuc                                        29

<210> SEQ ID NO 32
<211> LENGTH: 28
<212> TYPE: RNA
<213> ORGANISM: Mus musculus

<400> SEQUENCE: 32
ucugagguag aaaggugauc auggcucu                                         28

<210> SEQ ID NO 33
<211> LENGTH: 29
<212> TYPE: RNA
<213> ORGANISM: Mus musculus

<400> SEQUENCE: 33
uucugaggua gaaaggugau cauggcucu                                        29

<210> SEQ ID NO 34
<211> LENGTH: 30
<212> TYPE: RNA
<213> ORGANISM: Mus musculus

<400> SEQUENCE: 34
guucugaggu agaaagguga ucauggcucu                                       30

<210> SEQ ID NO 35
<211> LENGTH: 29
<212> TYPE: RNA
<213> ORGANISM: Mus musculus

<400> SEQUENCE: 35
ucugagguag aaaggugauc auggcucuc                                        29

<210> SEQ ID NO 36
<211> LENGTH: 30
<212> TYPE: RNA
<213> ORGANISM: Mus musculus

<400> SEQUENCE: 36
uucugaggua gaaaggugau cauggcucuc                                       30

<210> SEQ ID NO 37
<211> LENGTH: 31
<212> TYPE: RNA
<213> ORGANISM: Mus musculus

<400> SEQUENCE: 37
guucugaggu agaaagguga ucauggcucu c                                     31

<210> SEQ ID NO 38
<211> LENGTH: 30
<212> TYPE: RNA
<213> ORGANISM: Mus musculus

<400> SEQUENCE: 38
ucugagguag aaaggugauc auggcucucc                                       30

<210> SEQ ID NO 39
<211> LENGTH: 31
<212> TYPE: RNA
<213> ORGANISM: Mus musculus
```

```
<400> SEQUENCE: 39
uucugaggua gaaaggugau cauggcucuc c                              31

<210> SEQ ID NO 40
<211> LENGTH: 32
<212> TYPE: RNA
<213> ORGANISM: Mus musculus

<400> SEQUENCE: 40
guucugaggu agaaagguga ucauggcucu cc                             32

<210> SEQ ID NO 41
<211> LENGTH: 27
<212> TYPE: RNA
<213> ORGANISM: Homo sapiens

<400> SEQUENCE: 41
cugagguaga aaggugguca uggcuuu                                   27

<210> SEQ ID NO 42
<211> LENGTH: 28
<212> TYPE: RNA
<213> ORGANISM: Homo sapiens

<400> SEQUENCE: 42
cugagguaga aaggugguca uggcuuuc                                  28

<210> SEQ ID NO 43
<211> LENGTH: 29
<212> TYPE: RNA
<213> ORGANISM: Homo sapiens

<400> SEQUENCE: 43
cugagguaga aaggugguca uggcuuucc                                 29

<210> SEQ ID NO 44
<211> LENGTH: 27
<212> TYPE: RNA
<213> ORGANISM: Homo sapiens

<400> SEQUENCE: 44
ucugagguag aaaggugguc auggcuu                                   27

<210> SEQ ID NO 45
<211> LENGTH: 28
<212> TYPE: RNA
<213> ORGANISM: Homo sapiens

<400> SEQUENCE: 45
aucugaggua gaaagguggu cauggcuu                                  28

<210> SEQ ID NO 46
<211> LENGTH: 29
<212> TYPE: RNA
<213> ORGANISM: Homo sapiens

<400> SEQUENCE: 46
gaucugaggu agaaaggugg ucauggcuu                                 29

<210> SEQ ID NO 47
<211> LENGTH: 28
<212> TYPE: RNA
<213> ORGANISM: Homo sapiens
```

```
<400> SEQUENCE: 47
ucugagguag aaaggugguc auggcuuu                                    28

<210> SEQ ID NO 48
<211> LENGTH: 29
<212> TYPE: RNA
<213> ORGANISM: Homo sapiens

<400> SEQUENCE: 48
aucugaggua gaaaggyggu cauggcuuu                                   29

<210> SEQ ID NO 49
<211> LENGTH: 30
<212> TYPE: RNA
<213> ORGANISM: Homo sapiens

<400> SEQUENCE: 49
gaucugaggu agaaaggugg ucauggcuuu                                  30

<210> SEQ ID NO 50
<211> LENGTH: 29
<212> TYPE: RNA
<213> ORGANISM: Homo sapiens

<400> SEQUENCE: 50
ucugagguag aaaggugguc auggcuuuc                                   29

<210> SEQ ID NO 51
<211> LENGTH: 30
<212> TYPE: RNA
<213> ORGANISM: Homo sapiens

<400> SEQUENCE: 51
aucugaggua gaaaggyggu cauggcuuuc                                  30

<210> SEQ ID NO 52
<211> LENGTH: 31
<212> TYPE: RNA
<213> ORGANISM: Homo sapiens

<400> SEQUENCE: 52
gaucugaggu agaaaggugg ucauggcuuu c                                31

<210> SEQ ID NO 53
<211> LENGTH: 30
<212> TYPE: RNA
<213> ORGANISM: Homo sapiens

<400> SEQUENCE: 53
ucugagguag aaaggugguc auggcuuucc                                  30

<210> SEQ ID NO 54
<211> LENGTH: 31
<212> TYPE: RNA
<213> ORGANISM: Homo sapiens

<400> SEQUENCE: 54
aucugaggua gaaaggyggu cauggcuuuc c                                31

<210> SEQ ID NO 55
<211> LENGTH: 32
<212> TYPE: RNA
```

<213> ORGANISM: Homo sapiens

<400> SEQUENCE: 55

| gaucugaggu agaaaggugg ucauggcuuu cc | 32 |

<210> SEQ ID NO 56
<211> LENGTH: 2045
<212> TYPE: DNA
<213> ORGANISM: Homo sapiens

<400> SEQUENCE: 56

| tgaagtattc atccggccaa ccaatgtttc ctgacgtaca gtgttgccct tttcagcaaa | 60 |
| tgccaattcc aagttccatt aaatcagaag ctccatggct ccttggccca cgatgttgag | 120 |
| tgctgactgt gtgttctact gaagagtaa aacactgact atccaaagag aaatggatat | 180 |
| tttgttttta taataaccat atattattgt tttcttcttc cctttctatg caagtgtaaa | 240 |
| ttaatgaaca gagaggtatt tggaaatggt aatacatttg tcacggattt gtataatgta | 300 |
| tacagcattg ggaaagtggg tgggggcttt ctaatatgat accgtctttt taataactat | 360 |
| gacaaagctt acataagaat tagaagacca ctttacattt ttacattcct tctgctgttc | 420 |
| atattaacct tgcacaatta cttcattttt tctttgactc ttttaccaca atgttttggt | 480 |
| tatttataat ttatcagcca tatgtttatc agccatataa ccaactagat cccaaataga | 540 |
| tccatgtatt tgtttccgtg atttggccac attaataaat tcataaattt caatcaaata | 600 |
| tcttatatat acacacatat ggtttaagct acagccctgt gtatgccgtt aactttatt | 660 |
| tgacgttgcc cacttacttc tttgctgacc acttggataa ccgtaataaa atcctataa | 720 |
| gcctaaatgg catttctttt gggatatttt tcctgcattt tattccctt ttatataagt | 780 |
| aggaattaat tatttatttt atgtcttaat ctatttgata agaagacta cattataata | 840 |
| atctcaaaga tcatattacc aaaggttgcc cacttgagca tattttcatt ttgacacaga | 900 |
| aacaaaattt agtacaacct ttcctagttc ccatgtcttg atttcatca ttacatgcac | 960 |
| agcagacctt tacctattgt gataccagaa cacatcattg tctttggttc ccttcaaaga | 1020 |
| gaattttatt gttgttttgt attttcaagt ccttaatagt tcttgaaact cctagttgtt | 1080 |
| ttcttgttga aagcagacac acatttagtg cacggcttat tttaccttc gggtgaaaga | 1140 |
| tcagatgttt ttatacccct cacttgatca atatatttgg aaagaatgtt tatcaaaagt | 1200 |
| ctatgtcact gcttctacag aagaatgaaa ttaatgctta ggtgatggta cctccaccta | 1260 |
| catcttttg agtgcattca attatgtatt ttggtttagc ttctgattta acatttaatt | 1320 |
| gattcagttt aaacatgtta cttaattagc aaatgtagag gaaccaaaaa aaggtgaaaa | 1380 |
| taatatgttt tgattcaaac ctaaagacat aaaaacataa agacatttta actttgggtt | 1440 |
| ctctttagct gggatctggc cagaaggagg cttaaagtta gaaattgcta ttatttaga | 1500 |
| ataggttggg tgggttgggg ggcaagggtg tctatttgca gcagagatat tttgaaaaga | 1560 |
| agaaaattgt tttatataaa aaggaaagcc atgaccacct ttctacctca gatccatctt | 1620 |
| catccattgc attggaaact gctttatgct gctgcagtct gcaaagtcta gagcttttat | 1680 |
| caggccatgt cataccccaag aaagcaccta tttaagaaa aaacaattcc ctgagctctc | 1740 |
| aactccaagt tgtagatttg gtgtcttcct tgttcttact ttaaaaagtc atgtgttaat | 1800 |
| ttttttttctg cctgtatttg tatgcaaaat gtcctctatc tgctattaaa gaaaagctac | 1860 |
| gtaaaacact acattgtaac cttctaagta ataataaata aaaagaaata tattgcagta | 1920 |
| acaatgggaa gtaagtatgt agttcttttg aaatatgtgg taaagaacta atcacagact | 1980 |

```
atcatctaat ctggttacat attgtatttt tcatcctgaa taaaagtaat tttaacacaa    2040
aaaaa                                                                2045

<210> SEQ ID NO 57
<211> LENGTH: 23
<212> TYPE: DNA
<213> ORGANISM: Homo sapiens

<400> SEQUENCE: 57
ttgggaaagt gggtgggggc ttt                                              23

<210> SEQ ID NO 58
<211> LENGTH: 26
<212> TYPE: DNA
<213> ORGANISM: Homo sapiens

<400> SEQUENCE: 58
ataggttggg tgggttgggg ggcaag                                           26

<210> SEQ ID NO 59
<211> LENGTH: 25
<212> TYPE: DNA
<213> ORGANISM: Homo sapiens

<400> SEQUENCE: 59
gaccacttta catttttaca ttcct                                            25

<210> SEQ ID NO 60
<211> LENGTH: 22
<212> TYPE: DNA
<213> ORGANISM: Homo sapiens

<400> SEQUENCE: 60
ataggttggg tgggttgggg gg                                               22

<210> SEQ ID NO 61
<211> LENGTH: 24
<212> TYPE: DNA
<213> ORGANISM: Homo sapiens

<400> SEQUENCE: 61
aggttgggtg ggttgggggg caag                                             24

<210> SEQ ID NO 62
<211> LENGTH: 24
<212> TYPE: DNA
<213> ORGANISM: Homo sapiens

<400> SEQUENCE: 62
agccatgacc acctttctac ctca                                             24

<210> SEQ ID NO 63
<211> LENGTH: 24
<212> TYPE: DNA
<213> ORGANISM: Homo sapiens

<400> SEQUENCE: 63
atccattgca ttggaaactg cttt                                             24

<210> SEQ ID NO 64
<211> LENGTH: 22
<212> TYPE: DNA
```

<213> ORGANISM: Homo sapiens

<400> SEQUENCE: 64
tcaagtcagt gtacaggcca gc                                    22

<210> SEQ ID NO 65
<211> LENGTH: 19
<212> TYPE: DNA
<213> ORGANISM: Homo sapiens

<400> SEQUENCE: 65
aaagttgcgc ggaggagtt                                        19

<210> SEQ ID NO 66
<211> LENGTH: 21
<212> TYPE: DNA
<213> ORGANISM: Homo sapiens

<400> SEQUENCE: 66
cccttcttgg cctttatgag g                                     21

<210> SEQ ID NO 67
<211> LENGTH: 21
<212> TYPE: DNA
<213> ORGANISM: Homo sapiens

<400> SEQUENCE: 67
atcggaccca ggattctttt c                                     21

<210> SEQ ID NO 68
<211> LENGTH: 20
<212> TYPE: DNA
<213> ORGANISM: Homo sapiens

<400> SEQUENCE: 68
ccatttcatc aggtgcatct                                       20

<210> SEQ ID NO 69
<211> LENGTH: 23
<212> TYPE: DNA
<213> ORGANISM: Homo sapiens

<400> SEQUENCE: 69
cgtgcgtgac atcaaagaga agc                                   23

<210> SEQ ID NO 70
<211> LENGTH: 23
<212> TYPE: DNA
<213> ORGANISM: Homo sapiens

<400> SEQUENCE: 70
cccaagaagg aaggctggaa aag                                   23

<210> SEQ ID NO 71
<211> LENGTH: 25
<212> TYPE: RNA
<213> ORGANISM: Homo sapiens

<400> SEQUENCE: 71
gugagcacuu cuuccuucu uuuuu                                  25

<210> SEQ ID NO 72
<211> LENGTH: 25

```
<212> TYPE: RNA
<213> ORGANISM: Homo sapiens

<400> SEQUENCE: 72
gugagcacuu cuuccuucu uuuuu                                          25

<210> SEQ ID NO 73
<211> LENGTH: 32
<212> TYPE: DNA
<213> ORGANISM: Homo sapiens

<400> SEQUENCE: 73
gtccaagcct gtattgatgt caagctgaac ca                                 32

<210> SEQ ID NO 74
<211> LENGTH: 33
<212> TYPE: DNA
<213> ORGANISM: Homo sapiens

<400> SEQUENCE: 74
acttaagcct cttgccagag tttcaagata atc                                33

<210> SEQ ID NO 75
<211> LENGTH: 31
<212> TYPE: DNA
<213> ORGANISM: Homo sapiens

<400> SEQUENCE: 75
caggggccgg ccagtattca tccggccaac c                                  31

<210> SEQ ID NO 76
<211> LENGTH: 39
<212> TYPE: DNA
<213> ORGANISM: Homo sapiens

<400> SEQUENCE: 76
caaaggccgg ccgtgttaaa attactttta ttcaggatg                          39

<210> SEQ ID NO 77
<211> LENGTH: 28
<212> TYPE: DNA
<213> ORGANISM: Homo sapiens

<400> SEQUENCE: 77
gcgtgcagat cgagcgttta tccatttg                                      28

<210> SEQ ID NO 78
<211> LENGTH: 21
<212> TYPE: DNA
<213> ORGANISM: Homo sapiens

<400> SEQUENCE: 78
gggcatcacc acgaaaatct c                                             21

<210> SEQ ID NO 79
<211> LENGTH: 19
<212> TYPE: DNA
<213> ORGANISM: Homo sapiens

<400> SEQUENCE: 79
ctgccgttgt caaacacct                                                19

<210> SEQ ID NO 80
```

```
<211> LENGTH: 23
<212> TYPE: DNA
<213> ORGANISM: Homo sapiens

<400> SEQUENCE: 80
ccatgggatc cacggctccg agg                                             23

<210> SEQ ID NO 81
<211> LENGTH: 34
<212> TYPE: DNA
<213> ORGANISM: Homo sapiens

<400> SEQUENCE: 81
ccatggcttg aatgagtttc agtataatcc aaag                                 34

<210> SEQ ID NO 82
<211> LENGTH: 26
<212> TYPE: DNA
<213> ORGANISM: Homo sapiens

<400> SEQUENCE: 82
atccatttgg taaaggtttt cttctg                                          26

<210> SEQ ID NO 83
<211> LENGTH: 26
<212> TYPE: DNA
<213> ORGANISM: Homo sapiens

<400> SEQUENCE: 83
acgaattcag tgacatcatt aagtcc                                          26

<210> SEQ ID NO 84
<211> LENGTH: 20
<212> TYPE: DNA
<213> ORGANISM: Homo sapiens

<400> SEQUENCE: 84
atcattgtgt tcatcagatc                                                 20

<210> SEQ ID NO 85
<211> LENGTH: 28
<212> TYPE: DNA
<213> ORGANISM: Homo sapiens

<400> SEQUENCE: 85
gcgtgcagtg gaccattttt cagattta                                        28

<210> SEQ ID NO 86
<211> LENGTH: 28
<212> TYPE: DNA
<213> ORGANISM: Homo sapiens

<400> SEQUENCE: 86
gcgtgcagat cgagcgttta tccatttg                                        28

<210> SEQ ID NO 87
<211> LENGTH: 21
<212> TYPE: DNA
<213> ORGANISM: Homo sapiens

<400> SEQUENCE: 87
ttctttgcag ctccttcgtt g                                               21
```

```
<210> SEQ ID NO 88
<211> LENGTH: 38
<212> TYPE: DNA
<213> ORGANISM: Mus musculus

<400> SEQUENCE: 88
aggggagagc catgatcacc tttctacctc agaaccac                                38

<210> SEQ ID NO 89
<211> LENGTH: 38
<212> TYPE: DNA
<213> ORGANISM: Homo sapiens

<400> SEQUENCE: 89
aaaggaaagc catgaccacc tttctacctc agatccat                                38
```

METHODS FOR ENHANCING UTROPHIN PRODUCTION VIA INHIBITION OF MICRORNA

CROSS-REFERENCE TO RELATED APPLICATIONS

This application is a National Phase Application of PCT International Application No. PCT/US2017/042862, International Filing Date Jul. 19, 2017, claiming the benefit of U.S. Patent Application No. 62/364,207, filed Jul. 19, 2016 which are hereby incorporated by reference.

FIELD OF THE INVENTION

The invention relates to methods for enhancing utrophin protein production and methods for treating myopathies, such as Duchenne Muscular Dystrophy (DMD). Specifically, the invention relates to compositions and methods for enhancing utrophin protein translation in a subject by inhibition of microRNAs.

BACKGROUND OF THE INVENTION

Duchenne Muscular Dystrophy (DMD) is one of a group of muscular dystrophies characterized by the enlargement of muscles. DMD is one of the most prevalent types of muscular dystrophy and is characterized by rapid progression of muscle degeneration which occurs early in life. DMD is X-linked and affect mainly males—an estimated 1 in 3,500 boys worldwide.

The gene for DMD, found on the X chromosome, encodes a large protein—dystrophin. Dystrophin is required inside muscle cells for structural support: it is thought to strengthen muscle cells by anchoring elements of the internal cytoskeleton to the surface membrane and external structures. Without it, the muscle cannot produce force effectively and is susceptible to damage during contraction, eventually leading to muscle death and replacement by fatty and fibrous tissue. The accompanying immune response can add to the damage.

A mouse model for DMD exists, and is proving useful for furthering understanding of both the normal function of dystrophin and the pathology of the disease. In particular, experiments that enhance the production of utrophin, a dystrophin relative, in order to compensate for the loss of dystrophin are promising, and may lead to the development of effective therapies for this devastating disease. Accordingly, a need exists for enhancing utrophin production in order to treat muscular dystrophies and other myopathies.

MicroRNAs (miRNAs) are small, RNA molecules encoded in the genomes of plants and animals. These highly conserved, ~21-mer RNAs regulate the expression of genes by binding to the 3' or 5'-untranslated regions (3'-UTR or 5'-UTR) of specific mRNAs.

Although miRNA was first described well over a decade ago, only in recent years has the breadth and diversity of this class of small, regulatory RNAs been appreciated. A great deal of effort has gone into understanding how, when, and where miRNAs are produced and function in cells, tissues, and organisms. Each miRNA is thought to regulate multiple genes, and since hundreds of miRNA genes are predicted to be present in higher eukaryotes the potential regulatory circuitry afforded by miRNA is enormous.

MicroRNAs may act as key regulators of processes as diverse as early development, cell proliferation and cell death, apoptosis and fat metabolism, and cell differentiation. Studies of microRNA expression implicate microRNAs in brain development chronic lymphocytic leukemia, colonic adenocarcinoma, Burkett's Lymphoma, and viral infection suggesting possible links between miRNAs and viral disease, neurodevelopment, and cancer. miRNAs are differentially expressed in myopathies and have been implicated in heart disease. Accordingly, a need exists for determining the role of microRNAs in utrophin production in order to treat myopathies or utrophin mediated diseases.

SUMMARY OF THE INVENTION

The present invention relates to methods and compositions for enhancing utrophin protein production in a cell by inhibiting a utrophin microRNA molecule.

In one aspect, provided herein are methods of treating a muscle disease or muscular dystrophy (e.g., Duchenne Muscular Dystrophy (DMD)) in a subject, by administering to the subject an effective amount of an antisense oligonucleotide that specifically hybridizes to a microRNA binding sequence in a utrophin mRNA 3' untranslated region (UTR) and inhibits the binding of the microRNA to the utrophin mRNA 3'-UTR, wherein the microRNA is selected from the group consisting of Let-7c, miR-133b, miR-150, miR-196b, miR-206, miR-296-5p, and a combination thereof.

In another aspect, provided herein are pharmaceutical compositions that include an antisense oligonucleotide that specifically hybridizes to a microRNA binding sequence in a utrophin mRNA 3' untranslated region (UTR) and inhibits the binding of the microRNA to the 3'-UTR utrophin mRNA, wherein the microRNA is selected from the group consisting of Let-7c, miR-133b, miR-150, miR-196b, miR-206, and miR-296-5p, and a combination thereof and at least one pharmaceutically acceptable excipient, wherein the oligonucleotide is present in an amount effective to block or interfere the binding of the microRNA to the utrophin 3' untranslated region (UTR).

In another aspect, provided herein are methods of treating a muscle disease or muscular dystrophy (e.g., Duchenne Muscular Dystrophy (DMD)), in a human subject, by administering to the subject an effective amount of an antisense oligonucleotide that specifically hybridizes to a Let-7c microRNA binding sequence in a utrophin mRNA 3' untranslated region (UTR) and inhibits the binding of the Let-7c microRNA to the utrophin mRNA 3'-UTR. In some embodiments, the oligonucleotide has a sequence that includes a nucleic acid sequence set forth in SEQ ID NO: 24 (5'-CUG AGG UAG AAA GGU GAU CAU GGC UC-3') or SEQ ID NO: 25 (5'-CUG AGG UAG AAA GGU GGU CAU GGC UU-3'). In some embodiments, the oligonucleotide has a sequence that includes the nucleic acid sequence set forth SEQ ID NOs: 24-55.

In another aspect, provided herein are pharmaceutical compositions that include an antisense oligonucleotide that specifically hybridizes to a Let-7c microRNA binding sequence in a 3' untranslated region (UTR) of a utrophin mRNA and inhibits the binding of the Let-7c microRNA to the utrophin mRNA 3'-UTR and at least one pharmaceutically acceptable excipient, wherein the antisense oligonucleotide is present in an amount effective in a human subject to inhibit the binding of Let-7 microRNA with its utrophin mRNA 3'-UTR binding sequence. In some embodiments, the oligonucleotide has a sequence that includes a nucleic acid sequence set forth in SEQ ID NO: 24 (5'-CUG AGG UAG AAA GGU GAU CAU GGC UC-3') or SEQ ID NO: 25 (5'-CUG AGG UAG AAA GGU GGU CAU GGC UU-3'). In some embodiments, the oligonucleotide has a sequence that includes the nucleic acid sequence set forth SEQ ID NOs: 24-55.

In another aspect, provided herein are methods for treating a muscle disease or muscular dystrophy (e.g., Duchenne Muscular Dystrophy (DMD)), in a subject, by administering to the subject an effective amount of a composition that inhibits a utrophin microRNA molecule. Also provided herein are the methods for reducing the symptoms associated with a muscular dystrophy (e.g., DMD), in a subject, by administering to the subject an effective amount of a composition that inhibits a utrophin microRNA molecule.

In another aspect, provided herein are pharmaceutical compositions that include an effective amount of an agent that inhibits utrophin microRNA molecule. For example, the agent is selected from a let-7c antisense molecule, a miR-196b antisense molecule, a miR-133b antisense molecule, a miR-150 antisense molecule, a miR-206 antisense molecule, a miR-296-5p antisense molecule, or a combination thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIG. 19. 2OMePS let7-blocker upregulates endogenous utrophin protein. C2C12 cells were transfected with 300 nM control or let7-blocking 2OMePS oligomers (DMSO (0.025%) was also present in both cases). Endogenous utrophin protein was assayed by Western blotting after 72 hours. A. Representative Western blot. B. Quantification of utrophin band density normalized to tubulin band density. Bars represent mean±standard error from 3 independent experiments. The let7-blocker increased endogenous utrophin protein by 2.2-fold, compared to the control 2OMePS. * Significantly different from control 2OMePS by paired t test, p,0.05.

FIG. 20 shows 2OMePS oligos (i.e., Let-7 Oligos) which are synthetic molecules designed to bind the microRNA binding sites in 3'UTR of utrophin mRNA.

FIG. 21. Utrophin Let-7 blockers were able to upregulate utrophin reporter constructs in human HEK293T cells.

FIG. 30. Utrophin Let-7 SBO treatment decreased centrally nucleated fibers (CNFs) in TA muscle.

FIG. 35. Utrophin Let-7 SBO treatment decreased muscle fiber size variability.

FIG. 36. Utrophin Let-7 SBO administration increased utrophin protein expression in the diaphragm. B. let-7 SBO Rx increases Utrophin protein expression.

FIG. 46: Effect of intraperitoneal let7-SBOs treatment on utrophin upregulation in muscles of 2 months old mdx mice after 1 month of treatment. Western blots and quantification of utrophin expression in diaphragm (A, B), gastrocnemius (C, D) and TA (E, F) muscles with low and high dose let7-SBOs treatment compared with control oligonucleotides. Vinculin was used to control for equal loading. Bands were densitometrically evaluated, normalized to Vinculin. Bars represent mean±SD (n=3 per group). Differences between groups were analyzed by the Mann-Whitney U test (*P≤0.05).

FIG. 48: Effect of intraperitoneal let7-SBOs treatment on muscles morphology. Regeneration was quantified from the central nucleation counted from H&E-stained transverse TA (A) and EDL (B) muscles (n=3 per group) sections from let7-SBOs treated mdx mice compared to the respective dose of control oligonucleotides (Mann-Whitney U test, *P≤0.05). Scatter dot plot represent mean±SD (n=3 per group). (C, D) Histogram distribution of EDL muscle fibers minimal Feret's diameter in mdx mice (n=3 per group) injected with low (C) and high (D) dose of let7-SBOs treated (red) and control oligonucleotides (blue). Variance coefficient of minimal Feret's diameter are shown in inset graph (variance coefficient 500±24 versus 431±11 in low dose group and 489±16 versus 444±26 in high dose group). Statistical analysis was performed by Mann-Whitney U test (*P≤0.05). Data represent mean±SD (n=3 per group). (E, F) Representative images of H&E staining showing decreased muscle damage, lack of cellular infiltration and fibrosis resulting from low and high dose of let7-SBOs treatment in diaphragm (E) and TA (F) compared to the respective dose of Control oligonucleotides (Scale bar=200 rpm). (G, H) Muscles fibrosis analyzed by the hydroxyproline content of diaphragm (G) and TA (H) muscles from let7-SBOs treated mdx showing hydroxyproline content in high dose of let7-SBOs treatment compared to the respective dose of control oligonucleotides. Significant differences were assessed by Mann-Whitney U test (*P≤0.05). Scatter dot plot represent mean±SD (n=3 per group).

FIG. 51: Luciferase activity of C2C12 cells transiently transfected with pGL3-5'Luc3', pGL3-5'Luc3'-Δlet7 construct and let7-SBOs. (A) Schematics of the WT reporter construct pGL3-5'Luc3' (luciferase reporter flanked by the 5'- and 3'-UTRs of mouse utrophin-A) and pGL3-5'Luc3'-Δlet7 reporter construct (luciferase reporter flanked by the 5'- and 3'-UTRs of mouse utrophin-A in which the let-7c binding site has been deleted) (B) C2C12 cells were transiently transfected with pGL3-5'Luc3' or pGL3-5'Luc3'-Δlet7 along with control oligonucleotides (blue) or let7-SBOs (red). Figure shows luciferase activity measured after 24 hrs of transfection. Bars represent mean±SD from 4 independent experiments. Statistical analysis was performed by 2-way ANOVA for multiple comparison followed by Bonferroni correction (*P≤0.01).

FIG. 52: Utrophin expression in TA muscle of mdx mice treated with intramuscular injection of let7-SBOs. (A) Utrophin expression in TA muscles of mdx mice (n=3 per group) with intramuscular injection of let7-SBOs and control oligonucleotides. α-Tubulin staining was used to control for equal loading. (B) Quantification of utrophin normalized to α-tubulin band density in western blot assay. Bars represent mean±SD (n=3 mice per experimental group). Statistical comparison was analyzed by Mann-Whitney U test (*P≤0.05).

Statistical analysis was performed by Mann-Whitney U test (*P≤0.05) to low and high dose treatment group, respectively.

Figure 55:
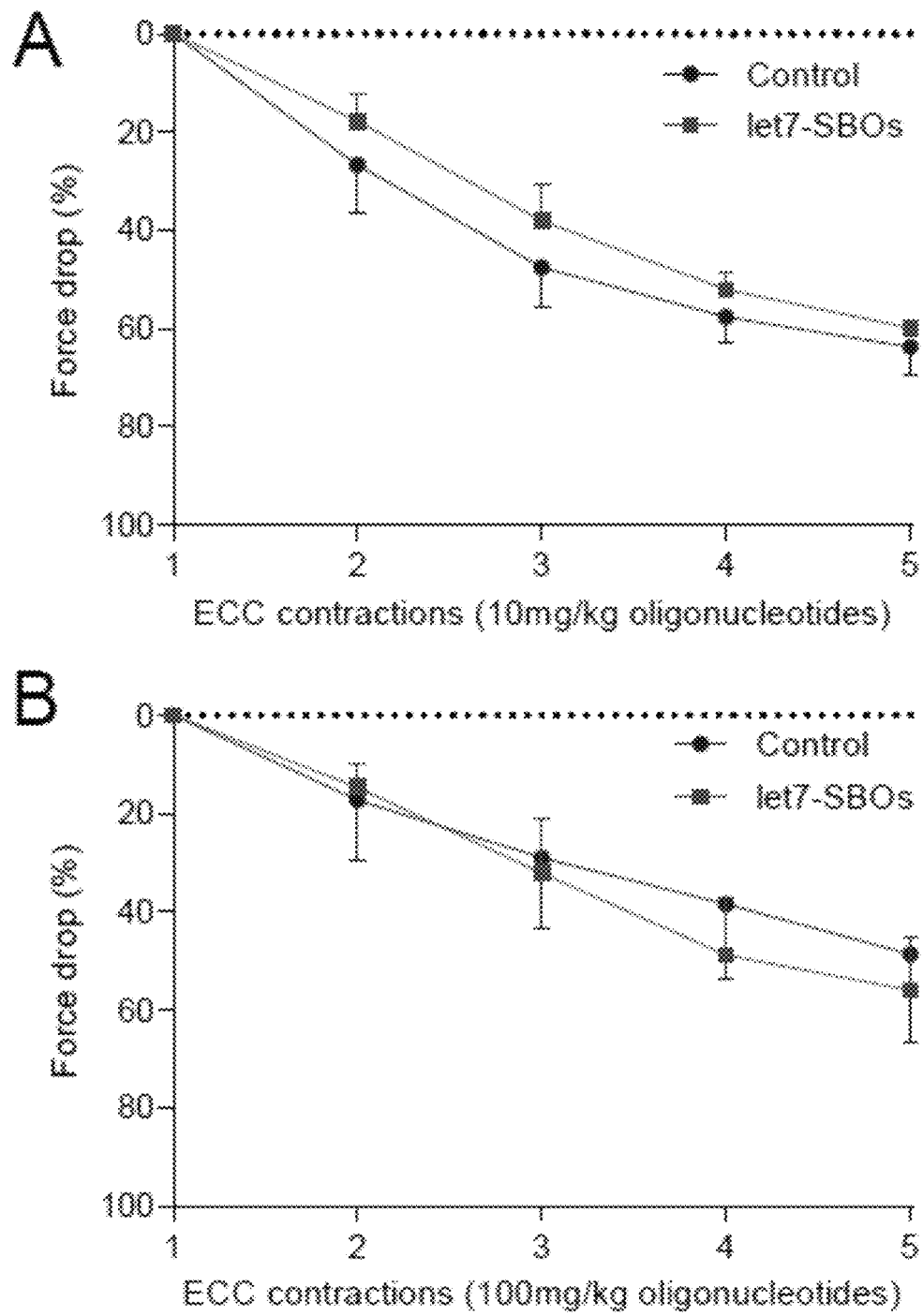

FIG. 55: Comparisons of drop in ECC force after five successive ECC's of EDL muscles of mdx mice. Force drop after five successive ECC's in EDL muscles of mdx mice treated with low (A) and high (B) dose of let7-SBOs and control oligonucleotides (n=3 for each group). Significant differences were assessed by 2-way ANOVA for multiple comparisons followed by Bonferroni correction (*P≤0.05).

FIG. 56: Effect of let7-SBOs on other let7 target genes. Western blots and quantification of other let-7 target genes c-Myc (A, B), Stat3 (C, D) and Jak3 (E, F) in gastrocnemius muscles with low and high dose let7-SBOs treatment compared with control oligonucleotides. Vinculin was used to control for equal loading. Bands were densitometrically evaluated, normalized to Vinculin. Significant differences were assessed by Mann-Whitney U test (*P≤0.05). Bars represent mean±SD (n=3 per group).

Figure 57:
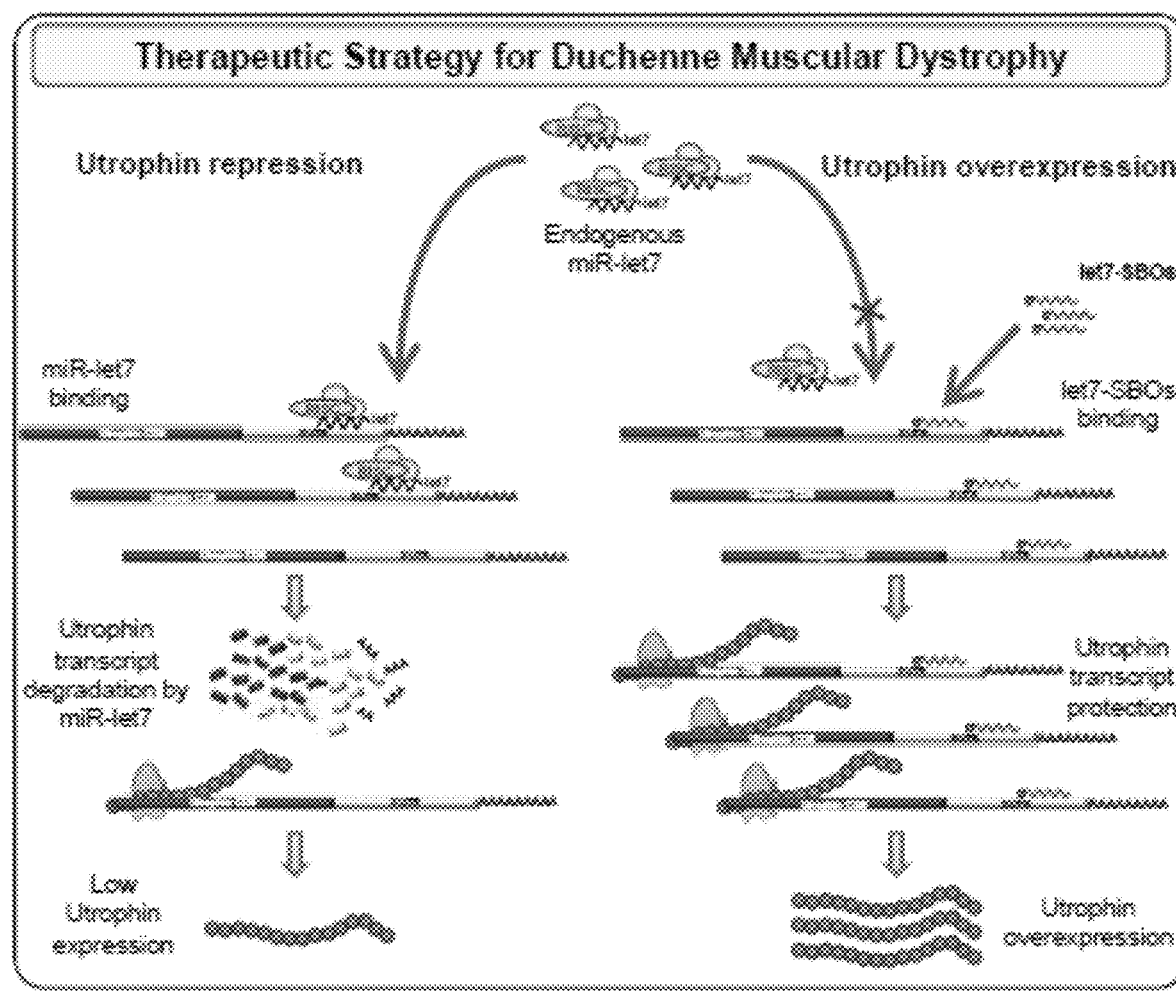

FIG. 57: Therapeutic Strategy for Duchenne Muscular Dystrophy.

DETAILED DESCRIPTION OF THE INVENTION

In one aspect, provided herein is a method of enhancing utrophin protein production in a cell, comprising the step of inhibiting a utrophin microRNA molecule. In one embodiment, the cell is a muscle cell.

In another aspect, provided herein are methods of treating a muscle disease or muscular dystrophy (e.g., Duchenne Muscular Dystrophy (DMD)), in a human subject, by administering to the subject an effective amount of an antisense oligonucleotide that specifically hybridizes to a Let-7c microRNA binding sequence in a utrophin mRNA 3' untranslated region (UTR) and inhibits the binding of the Let-7c microRNA to the utrophin mRNA 3'-UTR. In some embodiments, the oligonucleotide has a sequence that includes a nucleic acid sequence set forth in SEQ ID NO: 24 (5'-CUG AGG UAG AAA GGU GAU CAU GGC UC-3') or SEQ ID NO: 25 (5'-CUG AGG UAG AAA GGU GGU CAU GGC UU-3'). In some embodiments, the oligonucleotide has a sequence that includes the nucleic acid sequence set forth SEQ ID NOs: 24-55.

In another aspect, provided herein are pharmaceutical compositions that include an antisense oligonucleotide that specifically hybridizes to a Let-7c microRNA binding sequence in a 3'-UTR of a utrophin mRNA 3' untranslated region (UTR) and inhibits the binding of the Let-7c microRNA to the utrophin mRNA 3'-UTR and at least one pharmaceutically acceptable excipient, wherein the antisense oligonucleotide is present in an amount effective in a human subject to inhibit the binding of Let-7 microRNA with its utrophin mRNA 3'-UTR binding sequence. In some embodiments, the oligonucleotide has a sequence that includes a nucleic acid sequence set forth in SEQ ID NO: 24 (5'-CUG AGG UAG AAA GGU GAU CAU GGC UC-3') or SEQ ID NO: 25 (5'-CUG AGG UAG AAA GGU GGU CAU GGC UU-3'). In some embodiments, the oligonucleotide has a sequence that includes the nucleic acid sequence set forth SEQ ID NOs: 24-55.

In another embodiment, provided herein is a method of enhancing utrophin protein production in a cell, comprising the step of contacting a microRNA molecule that binds an utrophin mRNA with an inhibitor.

In another embodiment, provided herein is a method of enhancing utrophin protein production in a cell, comprising the step of contacting a microRNA molecule that binds an utrophin mRNA 3'-UTR with an inhibitor.

In another embodiment, provided herein is a method of enhancing utrophin protein production in a cell, comprising the step of contacting a microRNA molecule that binds an utrophin mRNA 5'-UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA 3'-UTR with an antisense molecule which inhibits the binding of the microRNA molecule to a 3'-UTR utrophin mRNA, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA 5'-UTR with an antisense molecule which inhibits the binding of the microRNA molecule to a 5'-UTR utrophin mRNA, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 3'-UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 5'-UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 3'-UTR with an antisense molecule which inhibits the binding of the microRNA molecule to a 3'-UTR utrophin mRNA, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 5'-UTR with an antisense molecule which inhibits the binding of the microRNA molecule to a 5'-UTR utrophin mRNA, thereby enhancing utrophin protein production in a cell. In another embodiment, the cell is a muscle cell.

The sequence of wild-type mouse (*Mus musculus*) utrophin mRNA can be found in GenBank with GenBank Accession #AK035043.1. The utrophin mouse mRNA 3'-UTR has the following nucleotide sequence:

```
                                         (SEQ ID NO: 13)
TGAGCATCTATCCAGCCAGCCAACATTTCCCGACCTTCAGTATTGCCCTC

TTCTGCAAATGCCAATCCCAAGACCCATTCAACCCCAAAGCTCCGTGGCT

CCACGACACAAGCTGTTGAGTGCTTACTGGGTGTTCTACTGAGGGAACCA

AACACTGACTATCCAAAGAGAAAAGGATATTTTGGTTTTCTAATAACGTA

TATTATTGTTTTCTTCTCCCCTTTCTATGCAACTGTAAATTAATGAACAG
```

-continued

```
AGAAGTATTTGGAGGTGGTAAAGCATTTGTCACTGATTTGTATAATATAT

ACAGCCATGGGAAAGTGGGTGGGGGCTTTCTAATATGAAACTGTCTTTTT

AATAACCAAGAGAAAAAATTGCATAAGAATTAGACCACTTTACATTATTA

CATTCCTTCTGCTGTTCACATTAACCTTGTACAATAACTTCACTTATTAT

TTGACTGTTTTACCATTATGTTTTGGTTATTTATAAATTTATCAGCCATA

CAAACAAATAGATTCTATGTATTTGTTTCTATAATCTGGCCAAATTCCTA

AGTTCATATATTTGAATCAAATATTTTACATATGTGGAGTAGGCAGGCAT

TCTGAAGATACTATTTAACTTTAGTTGACGTCACACACACCATCCTTTAG

TAACCACTGGATGACTACACTAAAAATCCTGTGGACTTTAACGGCAAGCT

GCTGGGGTATTTTTCCTCCTGTTTTTATTCCTTTTTTGTAAGTAGATCTT

GACGTCTTTATTTATTTCATCTTGCAATCTCTATAATAAAGAAGACTGTA

TTGTAATAGTCTCAAAAAATTATTTTACCAAGGGTTACCATTTAAGCATA

TTTTCATTTTGATTCAGAAACCAAAGTTGGTACAACCTCTCCTAGTACAT

GCAACCTTGGTTTTCATGAGAAAACACACGGCAGGCCTTTGCCCATTGTG

AGGAGAGCACACATCATGCTCTTCAGTTTCCTTTGAATAGACTTTTATTG

TTGTTTTTGTATTTTTCGAGTCCTGTGTAAGTTTTGAAAGCTCTGGTTGT

TTCCTTTGTGAAAGCAGGCAGATACTTAGTTGGCTGTCTCATTTGAAGCT

TTGGAGCAGATAGTCAGATGTCTCATGACCCCTCACTTGGCCAGCAGCAC

ATCCGAGAAGGATGTCACTCACAAGCCTACACCACGGCTTCTCTAGAATG

AAATCAGTGCTCGGATGATTGTATCCCTGCCTCTACTTCTGAGTGTGTTC

AACTAGGTATTGGCTTCTTTTTCTTTTTCTTTCTTTTTTTTTAATTTA

ACACTTAATTGCCGATTTTAGAGAAACCAAAAATAAAGGTGAAGGTAATA

TGTTTTGATTCAAACATATATGCTTTTAAACATCAGACATGCTAACTTTG

GTTCTCTTTACTGGAATCTGGCCCAGAGGAGGTGAAATTTAGAAATGTTA

TTCTTTAGATGGGTGGGTGGGTTGGGGGGCCAAGGGTGTCTATTTTCCAG

CATTAGATATTTTTGAGACGAAGAAAATTGTTTTATATAAGGGGAGAGCC

ATGATCACCTTTCTACCTCAGAACCACCTTCCTCCATTGTGTTGGACATA

GCTTTATATGCCGCAGTGTGCAAAACCTAGGGCTGTAGTCAGGCCTTTCC

ATACCCAGGAAGCACCTGTGTAAAGAAGATCAACAGAAACTCCCGGAACT

CAGAACCCCAAGTTGTAGATTTGGTGTCGTCCTTGTTCTTGCTTTGAGGA

GTCATGTATTCTTTTATTTCCTGCCTGTATTTGTATGCAAAATGATCTCT

ATCTGCTATTACAGAAAAGCTACACAAAACACTACATTGTAACCTTCTG

AGTAATAAATAAGAGGAAATATATTACAGTAACCATGATGAGAAATAAGT

GTATTGTTCTTTTGAAATATGTGGTTAATCGCAGACTGTCATCTAATCTG

TTACATACCGTATTTTTCATCCTGAATAAAAGTAATTTTAACACAAAATG

ACTTTGATGTTTGGCTGTGTTCAGCTGATGAAATCAGATCTCTGAATGTA

TGTGATGAAAGCTAACTATAAGATGATCTATATTCTGATAAATCTAAATA

TTTTCTGAAACTCTCTCTTATACATTAATCTAGTCTCCATTCACTCATTA

TCTCTCTCTCCTTTCTTGCATATAAATATGATTATATATTTTTCAATTTC

CTGTACAAATCAGAGTCTTATTACTAGGGAAAATGGATGTTATAAGTACA

TTCCTAAAGCCCATTGGGCCTTCATTTTTATAACTTGGAGCTACTGAGAT

TTATCAGGTTACTCTCTCAAATCCACTTTCATCACTAGACTCATAGTTTT

CTATGTATCTATATTATTATAACTAAATAAAAATATACATG.
```

The sequence of wild-type human (*Homo sapiens*) utrophin mRNA can be found in GenBank with GenBank Accession #NM_007124.2. The utrophin human mRNA 3'-UTR has the following nucleotide sequence:

(SEQ ID NO: 56)
```
TGAAGTATTCATCCGGCCAACCAATGTTTCCTGACGTACAGTGTTGCCCT

TTTCAGCAAATGCCAATTCCAAGTTCCATTAAATCAGAAGCTCCATGGCT

CCTTGGCCCACGATGTTGAGTGCTGACTGTGTGTTCTACTGAAAGAGTAA

AACACTGACTATCCAAAGAGAAATGGATATTTTGTTTTTATAATAACCAT

ATATTATTGTTTTCTTCTTCCCTTTCTATGCAAGTGTAAATTAATGAACA

GAGAGGTATTTGGAAATGGTAATACATTTGTCACGGATTTGTATAATGTA

TACAGCATTGGGAAAGTGGGTGGGGCTTTCTAATATGATACCGTCTTTT

TAATAACTATGACAAAGCTTACATAAGAATTAGAAGACCACTTTACATTT

TTACATTCCTTCTGCTGTTCATATTAACCTTGCACAATTACTTCATTTTT

TCTTTGACTCTTTTACCACAATGTTTTGGTTATTTATAATTTATCAGCCA

TATGTTTATCAGCCATATAACCAACTAGATCCCAAATAGATCCATGTATT

TGTTTCCGTGATTTGGCCACATTAATAAATTCATAAATTTCAATCAAATA

TCTTATATATACACACATATGGTTTAAGCTACAGCCCTGTGTATGCCGTT

TAACTTTATTTGACGTTGCCCACTTACTTCTTTGCTGACCACTTGGATAA

CCGTAATAAAAATCCTATAAGCCTAAATGGCATTTCTTTTGGGATATTTT

TCCTGCATTTTATTCCCTTTTTATATAAGTAGGAATTAATTATTTATTTT

ATGTCTTAATCTATTTGATAAAGAAGACTACATTATAATAATCTCAAAGA

TCATATTACCAAAGGTTGCCCACTTGAGCATATTTTCATTTTGACACAGA

AACAAAATTTAGTACAACCTTTCCTAGTTCCCATGTCTTGATTTTCATCA

TTACATGCACAGCAGACCTTTACCTATTGTGATACCAGAACACATCATTG

TCTTTGGTTCCCTTCAAAGAGAATTTTATTGTTGTTTTGTATTTTCAAGT

CCTTAATAGTTCTTGAAACTCCTAGTTGTTTTCTTGTTGAAAGCAGACAC

ACATTTAGTGCACGGCTTATTTTACCTTTCGGGTGAAAGATCAGATGTTT

TTATACCCTTCACTTGATCAATATATTTGGAAAGAATGTTTATCAAAAGT

CTATGTCACTGCTTCTACAGAAGAATGAAATTAATGCTTAGGTGATGGTA

CCTCCACCTACATCTTTTTGAGTGCATTCAATTATGTATTTTGGTTTAGC

TTCTGATTTAACATTTAATTGATTCAGTTTAAACATGTTACTTAATTAGC

AAATGTAGAGGAACCAAAAAAAGGTGAAAATAATATGTTTTGATTCAAAC

CTAAAGACATAAAAACATAAAGACATTTTAACTTGGGTTCTCTTTAGCT

GGGATCTGGCCAGAAGGAGGCTTAAAGTTAGAAATTGCTATTATTTTAGA

ATAGGTTGGGTGGGTTGGGGGCAAGGGTGTCTATTTGCAGCAGAGATAT

TTTGAAAAGAAGAAAATTGTTTTATATAAAAAGGAAAGCCATGACCACCT

TTCTACCTCAGATCCATCTTCATCCATTGCATTGGAAACTGCTTTATGCT

GCTGCAGTCTGCAAAGTCTAGAGCTTTTATCAGGCCATGTCATACCCAAG
```

-continued

AAAGCACCTATTTAAAGAAAAAACAATTCCCTGAGCTCTCAACTCCAAGT

TGTAGATTTGGTGTCTTCCTTGTTCTTACTTTAAAAAGTCATGTGTTAAT

TTTTTTTCTGCCTGTATTTGTATGCAAAATGTCCTCTATCTGCTATTAAA

GAAAAGCTACGTAAAACACTACATTGTAACCTTCTAAGTAATAATAAATA

AAAAGAAATATATTGCAGTAACAATGGGAAGTAAGTATGTAGTTCTTTTG

AAATATGTGGTAAAGAACTAATCACAGACTATCATCTAATCTGGTTACAT

ATTGTATTTTTCATCCTGAATAAAAGTAATTTTAACACAAAAAAA.

In one embodiment, the utrophin mRNA 3'-UTR nucleic acid sequence is a homologue, a variant, or a functional fragment of SEQ ID NO: 13. In one embodiment, the utrophin mRNA 3'-UTR nucleic acid sequence is a homologue, a variant, or a functional fragment of SEQ ID NO: 56.

Without wishing to be bound by theory, a microRNA of the invention inhibits utrophin protein production by binding to an utrophin 3'-UTR binding sequence.

In mouse mRNA, miR-296-5p has the following two binding sequences in utrophin 3'-UTR: 5'-ATGG-GAAAGTGGGTGGGGGCTTT-3' (SEQ ID NO: 14) and 5'-GGGTGGGTGGGTTGGGGGGCC-3' (SEQ ID NO: 23), respectively. In mouse mRNA, miR-206 binding sequence in utrophin 3'-UTR is: 5'-CCACTTTACATTAT-TACATTCC-3' (SEQ ID NO: 15). In mouse mRNA, miR-150 binding sequence in utrophin 3'-UTR is: 5'-ATGGGTGGGTGGGTTGGGGG-3' (SEQ ID NO: 16). In mouse mRNA, miR-133b binding sequence in utrophin 3'-UTR is: 5'-GTGGGTTGGGGGGCCAA-3' (SEQ ID NO: 17). In mouse mRNA, let-7c binding sequence in utrophin 3'-UTR is: 5'-AGCCATGATCACCTTTCTACCTCA-3' (SEQ ID NO: 18). In mouse mRNA, miR-196b binding sequence in utrophin 3'-UTR is: 5'-CCATACCCAG-GAAGCACCT-3' (SEQ ID NO: 19).

In human mRNA, miR-296-5p has the following two binding sequences in utrophin 3'-UTR: 5'-TTGG-GAAAGTGGGTGGGGGCTTT-3' (SEQ ID NO: 57) and 5'-ATAGGTTGGGTGGGTTGGGGGGCAAG-3' (SEQ ID NO: 58), respectively. In human mRNA, miR-206 binding sequence in utrophin 3'-UTR is: 5'-GACCACTTTACAT-TTTTACATTCCT-3' (SEQ ID NO: 59). In human mRNA, miR-150 binding sequence in utrophin 3'-UTR is: 5'-ATAGGTTGGGTGGGTTGGGGGG-3' (SEQ ID NO: 60). In human mRNA, miR-133b binding sequence in utrophin 3'-UTR is: 5'-AGGTTGGGTGGGTTGGGGGGCAAG-3' (SEQ ID NO: 61). In human mRNA, let-7c binding sequence in utrophin 3'-UTR is: 5'-AGCCATGACCACCTTTC-TACCTCA-3' (SEQ ID NO: 62). In human mRNA, miR-196b binding sequence in utrophin 3'-UTR is: 5'-ATCCAT-TGCATTGGAAACTGCTTT-3' (SEQ ID NO: 63).

In another embodiment, the cell is a skeletal muscle cell. In another embodiment, the cell is a smooth muscle cell. In another embodiment, the cell is a satellite muscle cell. In another embodiment, the cell is a cardiac muscle cell.

In another embodiment, the microRNA molecule is a muscle cell specific microRNA molecule. In another embodiment, the microRNA molecule binds to utrophin. In another embodiment, a microRNA molecule is complementary to a utrophin RNA sequence. In another embodiment, a microRNA molecule is complementary to a 5' untranslated region (UTR) of an utrophin RNA sequence. In another embodiment, a microRNA molecule is complementary to a 3'-UTR of an utrophin RNA sequence. In another embodiment, a microRNA molecule decreases the levels of utrophin protein. In another embodiment, a microRNA molecule decreases the levels of utrophin protein without decreasing the utrophin mRNA. In another embodiment, a microRNA molecule targets utrophin-A IRES. In another embodiment, a microRNA molecule targets utrophin-A IRES in a muscle cell. In another embodiment, a microRNA molecule represses utrophin-A IRES activity (FIGS. 3 and 7-9).

In another embodiment, the microRNA molecule is miR-206. In another embodiment, the microRNA molecule is let-7c. In another embodiment, the microRNA molecule is miR-196b. In another embodiment, the microRNA molecule is miR-133b. In another embodiment, the microRNA molecule is miR-150. In another embodiment, the microRNA molecule is miR-296-5p.

The sequence of Let-7c microRNA (mouse and human) is: 5'-UGAGGUAGUAGGUUGUAUGGUU-3' (SEQ ID NO: 1). In one embodiment, the sequence of a Let-7c microRNA inhibitor or anti-Let-7c is: 5'-AACCAUA-CAACCUACUACCUCA-3' (SEQ ID NO: 2).

The sequence of miR-133b microRNA (mouse and human) is: 5'-UUUGGUCCCCUUCAACCAGCUA-3' (SEQ ID NO: 3). In one embodiment, the sequence of a miR-133b microRNA inhibitor or anti-miR-133b is: 5'-UAGCUGGUUGAAGGGGACCAA-3'(SEQ ID NO: 4). The sequence of miR-150 microRNA (mouse and human) is: 5'-UCUCCCAACCCUUGUACCAGUG-3' (SEQ ID NO: 5). In one embodiment, the sequence of a miR-150 microRNA inhibitor or anti-miR-150 is: 5'-CACUGGUA-CAAGGGUUGGGAGA-3' (SEQ ID NO: 6). The sequence of miR-196b microRNA (mouse and human) is: 5'-UAG-GUAGUUUCCUGUUGUUGGG-3' (SEQ ID NO: 7). In one embodiment, the sequence of a miR-196b microRNA inhibitor or anti-miR-196b is: 5'-CCAACAACAGGAAAC-UACCUA-3' (SEQ ID NO: 8). The sequence of miR-206 microRNA (mouse and human) is: 5'-UGGAAU-GUAAGGAAGUGUGUGG-3' (SEQ ID NO: 9). In one embodiment, the sequence of a miR-206 microRNA inhibitor or anti-miR-206 is: 5'-CCACACACUUCCUUA-CAUUCCA-3' (SEQ ID NO: 10). The sequence of miR-296-5p microRNA (mouse and human) is: 5'-AGGGCCCCCCCUCAAUCCUGU-3' (SEQ ID NO: 11). In one embodiment, the sequence of a miR-296-5p microRNA inhibitor or anti-miR-296-5p is: 5'-ACAG-GAUUGAGGGGGGGCCCU-3' (SEQ ID NO: 12).

In another embodiment, the microRNA molecule miR-206 comprises the sequence of miRBase (http://www.mirbase.org) accession number MI0000249. In another embodiment, the microRNA molecule miR-206 comprises the sequence of miRBase accession number MI0000490. In another embodiment, the microRNA molecule miR-206 comprises the sequence of miRBase accession number MI0000948. In another embodiment, the microRNA molecule miR-206 comprises the sequence of miRBase accession number MI0001207. In another embodiment, the microRNA molecule miR-206 comprises the sequence of miRBase accession number MI0002045. In another embodiment, the microRNA molecule miR-206 comprises the sequence of miRBase accession number MI0002046. In another embodiment, the microRNA molecule miR-206 comprises the sequence of miRBase accession number MI0002619. In another embodiment, the microRNA molecule miR-206 comprises the sequence of miRBase accession number MI0002620. In another embodiment, the microRNA molecule miR-206 comprises the sequence of miRBase accession number MI0004863. In another embodiment, the microRNA molecule miR-206 comprises the sequence of miRBase accession number MI0005317. In another embodiment, the microRNA molecule miR-206 comprises the sequence of miRBase accession number MI0007667. In another embodiment, the microRNA molecule miR-206 comprises the sequence of miRBase accession number MI0008002.

In another embodiment, the microRNA molecule let-7c comprises the sequence of miRBase accession number MI0000064. In another embodiment, the microRNA molecule let-7c comprises the sequence of miRBase accession number MI0000559. In another embodiment, the microRNA molecule let-7c comprises the sequence of miRBase accession number MI0000560. In another embodiment, the microRNA molecule let-7c comprises the sequence of miRBase accession number MI0000830. In another embodiment, the microRNA molecule let-7c comprises the sequence of miRBase accession number MI0000831. In another embodiment, the microRNA molecule let-7c comprises the sequence of miRBase accession number MI0001174. In another embodiment, the microRNA molecule let-7c comprises the sequence of miRBase accession number MI0001866. In another embodiment, the microRNA molecule let-7c comprises the sequence of miRBase accession number MI0001867. In another embodiment, the microRNA molecule let-7c comprises the sequence of miRBase accession number MI0002445. In another embodiment, the microRNA molecule let-7c comprises the sequence of miRBase accession number MI0004886. In another embodiment, the microRNA molecule let-7c comprises the sequence of miRBase accession number MI0005124. In another embodiment, the microRNA molecule let-7c comprises the sequence of miRBase accession number MI0005454. In another embodiment, the microRNA molecule let-7c comprises the sequence of miRBase accession number MI0007138. In another embodiment, the microRNA molecule let-7c comprises the sequence of miRBase accession number MI0007152. In another embodiment, the microRNA molecule let-7c comprises the sequence of miRBase accession number MI0007183. In another embodiment, the microRNA molecule let-7c comprises the sequence of miRBase accession number MI0007184. In another embodiment, the microRNA molecule let-7c comprises the sequence of miRBase accession number MI0007574. In another embodiment, the microRNA molecule let-7c comprises the sequence of miRBase accession number MI0008076.

In another embodiment, the microRNA molecule miR-196b comprises the sequence of miRBase accession number MI0001150. In another embodiment, the microRNA molecule miR-196b comprises the sequence of miRBase accession number MI0001151. In another embodiment, the microRNA molecule miR-196b comprises the sequence of miRBase accession number MI0001152. In another embodiment, the microRNA molecule miR-196b comprises the sequence of miRBase accession number MI0002036. In another embodiment, the microRNA molecule miR-196b comprises the sequence of miRBase accession number MI0003365. In another embodiment, the microRNA molecule miR-196b comprises the sequence of miRBase accession number MI0003366. In another embodiment, the microRNA molecule miR-196b comprises the sequence of miRBase accession number MI0004943. In another embodiment, the microRNA molecule miR-196b comprises the sequence of miRBase accession number MI0005313. In another embodiment, the microRNA molecule miR-196b comprises the sequence of miRBase accession number MI0007660. In another embodiment, the microRNA molecule miR-196b comprises the sequence of miRBase accession number MI0008016.

In another embodiment, the microRNA molecule miR-133b comprises the sequence of miRBase accession number MI0000821. In another embodiment, the microRNA molecule miR-133b comprises the sequence of miRBase accession number MI0000822. In another embodiment, the microRNA molecule miR-133b comprises the sequence of miRBase accession number MI0001206. In another embodiment, the microRNA molecule miR-133b comprises the sequence of miRBase accession number MI0001994. In another embodiment, the microRNA molecule miR-133b comprises the sequence of miRBase accession number MI0003490. In another embodiment, the microRNA molecule miR-133b comprises the sequence of miRBase accession number MI0004837. In another embodiment, the microRNA molecule miR-133b comprises the sequence of miRBase accession number MI0007622.

In another embodiment, the microRNA molecule miR-150 comprises the sequence of miRBase accession number MI0000172. In another embodiment, the microRNA molecule miR-150 comprises the sequence of miRBase accession number MI0000479. In another embodiment, the microRNA molecule miR-150 comprises the sequence of miRBase accession number MI0000920. In another embodiment, the microRNA molecule miR-150 comprises the sequence of miRBase accession number MI0002016. In another embodiment, the microRNA molecule miR-150 comprises the sequence of miRBase accession number MI0004846. In another embodiment, the microRNA molecule miR-150 comprises the sequence of miRBase accession number MI0005058. In another embodiment, the microRNA molecule miR-150 comprises the sequence of miRBase accession number MI0007122. In another embodiment, the microRNA molecule miR-150 comprises the sequence of miRBase accession number MI0007123. In another embodiment, the microRNA molecule miR-150 comprises the sequence of miRBase accession number MI0007124. In another embodiment, the microRNA molecule miR-150 comprises the sequence of miRBase accession number MI0007125. In another embodiment, the microRNA molecule miR-150 comprises the sequence of miRBase accession number MI0007126. In another embodiment, the microRNA molecule miR-150 comprises the sequence of miRBase accession number MI0007127. In another embodiment, the microRNA molecule miR-150 comprises the sequence of miRBase accession number MI0007128. In another embodiment, the microRNA molecule miR-150 comprises the sequence of miRBase accession number MI0007641. In another embodiment, the microRNA molecule miR-150 comprises the sequence of miRBase accession number MI0007998.

In another embodiment, the microRNA molecule is miR-296-5p. In another embodiment, the microRNA molecule miR-296-5p comprises the sequence of miRBase accession number MI0000394. In another embodiment, the microRNA molecule miR-296-5p comprises the sequence of miRBase accession number MI0000747. In another embodiment, the microRNA molecule miR-296-5p comprises the sequence of miRBase accession number MI0007681.

Figure 1:
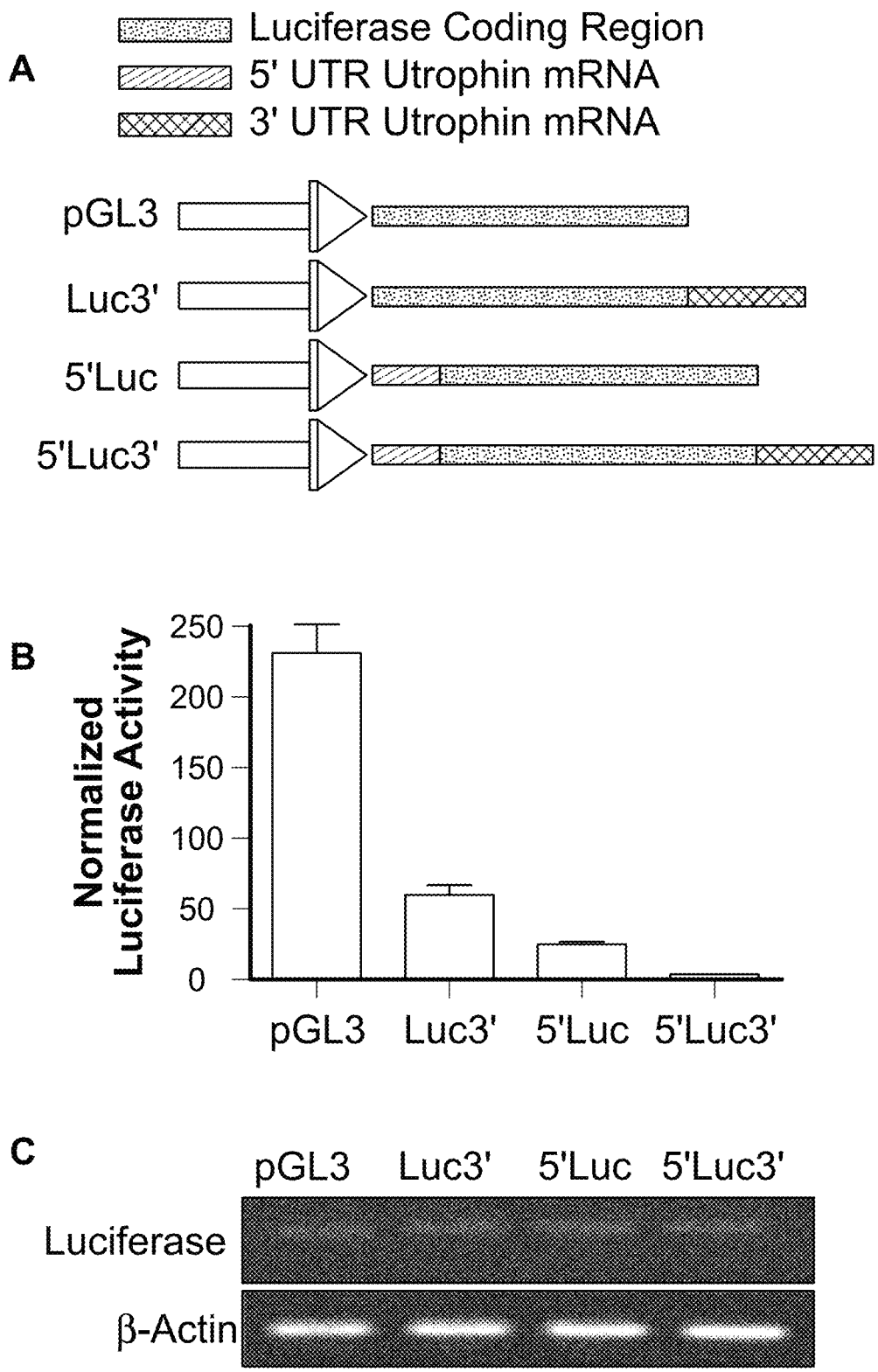
FIG. 1 shows the utrophin UTR-luciferase constructs used in C2C12 cells (A); a bar graph showing the luciferase activity in the transfected C2C12 cells (B); a gel showing mRNA expression in C2C12 of luciferase and β-actin by RT-PCR (C); a graph showing ribosomal profiling of utrophin-A mRNA in C2C12 cells by sucrose density gradient analysis (D). C2C12 cell extract was resolved on a sucrose density gradient, collected into eleven fractions, and the target mRNA level in each fraction was determined (D).

Utrophin upregulation is a therapeutic strategy for DMD. Normally, Utrophin-A expression is repressed through the 5' and 3'-UTRs by >98% at the translational level (FIG. 1). The Utrophin 5' and 3'-UTR contains microRNA target sites. In another embodiment, Utrophin 3'-UTR exhibits its inhibitory effect both on IRES and on cap-dependent translation.

Inhibition of microRNAs that target Utrophin UTRs by blocking the microRNA binding site in the mRNA or by binding to the microRNA itself are therapeutic strategies for DMD.

In another embodiment, inhibiting a microRNA molecule comprises contacting a microRNA molecule with a complementary antisense oligonucleotide sequence. In another embodiment, inhibiting an utrophin microRNA molecule comprises contacting an utrophin microRNA molecule with an utrophin microRNA antisense molecule. In another embodiment, inhibiting an utrophin microRNA molecule comprises contacting an utrophin microRNA molecule with an antisense molecule that specifically binds to or hybridizes with the utrophin microRNA. An oligonucleotide "specifically hybridizes" to a target polynucleotide if it hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense oligomer to the target sequence, as well as with exact complementarity.

In another embodiment, inhibiting let-7c, miR-196b, miR-133b, miR-150, miR-296-5p, miR-206 or any combination thereof leads to utrophin upregulation. In another embodiment, an inhibitor of let-7c, miR-196b, miR-133b, miR-150, miR-296-5p, miR-296 or any combination thereof is used as a Duchenne muscular dystrophy therapeutic agent.

In another embodiment, an antisense specific molecule comprises at least 3 consecutive nucleotides which are complementary to an utrophin microRNA molecule or a fragment thereof. In another embodiment, an antisense specific molecule comprises at least 3 consecutive nucleotides which are complementary to a muscle cell utrophin microRNA molecule or a fragment thereof. In another embodiment, an antisense specific molecule comprises at least 3 consecutive nucleotides which are complementary to an utrophin microRNA molecule or a fragment thereof as described herein. In another embodiment, an antisense specific molecule comprises at least 3 consecutive nucleotides which are complementary to any microRNA molecule represented by a miRBase accession number as described hereinabove or a fragment thereof. In another embodiment, an antisense specific molecule comprises at least 4 consecutive nucleotides which are complementary to any microRNA molecule represented by a miRBase accession number as described hereinabove or a fragment thereof. In another embodiment, an antisense specific molecule comprises at least 5 consecutive nucleotides which are complementary to any microRNA molecule represented by a miRBase accession number as described hereinabove or a fragment thereof. In another embodiment, an antisense specific molecule comprises at least 7 consecutive nucleotides which are complementary to any microRNA molecule represented by a miRBase accession number as described hereinabove or a fragment thereof. In another embodiment, an antisense specific molecule comprises at least 9 consecutive nucleotides which are complementary to any microRNA molecule represented by a miRBase accession number as described hereinabove or a fragment thereof. In another embodiment, an antisense specific molecule comprises at least 11 consecutive nucleotides which are complementary to any microRNA molecule represented by a miRBase accession number as described hereinabove or a fragment thereof.

In another embodiment, an antisense specific molecule comprises at least 3 consecutive nucleotides derived from the 5'-UTR or the 3'-UTR of utrophin RNA molecule. In another embodiment, an antisense specific molecule comprises at least 4 consecutive nucleotides derived from the 5'-UTR or the 3'-UTR of utrophin RNA molecule. In another embodiment, an antisense specific molecule comprises at least 5 consecutive nucleotides derived from the 5'-UTR or the 3'-UTR of utrophin RNA molecule. In another embodiment, an antisense specific molecule comprises at least 6 consecutive nucleotides derived from the 5'-UTR or the 3'-UTR of utrophin RNA molecule. In another embodiment, an antisense specific molecule comprises at least 8 consecutive nucleotides derived from the 5'-UTR or the 3'-UTR of utrophin RNA molecule. In another embodiment, an antisense specific molecule comprises at least 10 consecutive nucleotides derived from the 5'-UTR or the 3'-UTR of utrophin RNA molecule. In another embodiment, an antisense specific molecule comprises at least 12 consecutive nucleotides derived from the 5'-UTR or the 3'-UTR of utrophin RNA molecule. In another embodiment, an antisense specific molecule comprises at least 14 consecutive nucleotides derived from the 5'-UTR or the 3'-UTR of utrophin RNA molecule. For example, an antisense oligonucleotide derived from the 5'-UTR or the 3'-UTR of utrophin mRNA encompasses sequences that are complementary to sequences in the 5'-UTR or the 3'-UTR. In another embodiment, an antisense specific molecule comprises a complementary sequence to any microRNA molecule represented by a miRBase accession number as described hereinabove or a fragment thereof. In another embodiment, an antisense specific molecule comprises a homologous complementary sequence to any microRNA molecule represented by a miRBase accession number as described hereinabove or a fragment thereof.

A homologous complementary sequence is at least 60% homologous, at least 70% homologous, at least 80% homologous, at least 90% homologous, at least 95% homologous, at least 98% homologous, at least 99% homologous, or even 100% homologous.

In another embodiment, an antisense specific molecule comprises at least 3, at least 5, at least 7, at least 9, at least 11, or at least 13 consecutive nucleotides complementary to let-7c (e.g., a sequence set forth in SEQ ID NO: 2).

In another embodiment, an antisense specific molecule comprises at least 3, at least 5, at least 7, at least 9, at least 11, or at least 13 consecutive nucleotides complementary to miR-196b (e.g., a sequence set forth in SEQ ID NO: 8). In another embodiment, an antisense specific molecule comprises at least 3, at least 5, at least 7, at least 9, at least 11, or at least 13 consecutive nucleotides complementary to miR-133b (e.g., a sequence set forth in SEQ ID NO: 4). In another embodiment, an antisense specific molecule comprises at least 3, at least 5, at least 7, at least 9, at least 11, or at least 13 consecutive nucleotides complementary to miR-150 (e.g., a sequence set forth in SEQ ID NO: 6). In another embodiment, an antisense specific molecule comprises at least 3, at least 5, at least 7, at least 9, at least 11, or at least 13 consecutive nucleotides complementary to miR-296-5p (e.g., a sequence set forth in SEQ ID NO: 12). In another embodiment, an antisense specific molecule comprises at least 3, at least 5, at least 7, at least 9, at least 11, or at least 13 consecutive nucleotides complementary to miR-206 (e.g., a sequence set forth in SEQ ID NO: 10).

In another embodiment, an antisense molecule is a synthetic peptide nucleic acid (PNA). In another embodiment, an antisense molecule is a LNA.

In another aspect, the invention provides an antisense oligonucleotide effective to inhibit the binding of Let-7 microRNA with its corresponding 3' untranslated region (UTR) in utrophin mRNA. In one embodiment, the antisense oligonucleotide includes a nucleic acid sequence set forth in SEQ ID NO: 24, a fragment thereof, or a variant thereof. In another embodiment, the antisense oligonucleotide includes a nucleic acid sequence set forth in SEQ ID NO: 25, a fragment thereof, or a variant thereof. In some embodiments, a variant antisense oligonucleotide includes oligonucleotides where one or more additional bases have been added to and/or deleted from the 3' and/or 5' end. Examples of a variant antisense oligonucleotide include, for example, the nucleic acid sequences set forth in SEQ ID NOs. 26-55.

Examples of a variant antisense oligonucleotide of SEQ ID NO: 24 include, for example, the nucleic acid sequences set forth in SEQ ID NOs. 26-40. Examples of a variant antisense oligonucleotide of SEQ ID NO: 25 include, for example, nucleic acid sequences set forth in SEQ ID NOs. 41-55. The nucleic acid sequences of SEQ ID NOs. 24-55 are listed in Table below.

| SEQ ID NO: | SEQUENCE | Organism |
|---|---|---|
| SEQ ID NO: 24 | 5'-CUG AGG UAG AAA GGU GAU CAU GGC UC-3' | Mouse |
| SEQ ID NO: 25 | 5'-CUG AGG UAG AAA GGU GGU CAU GGC UU-3' | Human |
| SEQ ID NO: 26 | 5'-CUG AGG UAG AAA GGU GAU CAU GGC UCU-3' | Mouse |
| SEQ ID NO: 27 | 5'-CUG AGG UAG AAA GGU GAU CAU GGC UCU C-3' | Mouse |
| SEQ ID NO: 28 | 5'-CUG AGG UAG AAA GGU GAU CAU GGC UCU CC-3' | Mouse |
| SEQ ID NO: 29 | 5'-U CUG AGG UAG AAA GGU GAU CAU GGC UC-3' | Mouse |
| SEQ ID NO: 30 | 5'-UU CUG AGG UAG AAA GGU GAU CAU GGC UC-3' | Mouse |
| SEQ ID NO: 31 | 5'-GUU CUG AGG UAG AAA GGU GAU CAU GGC UC-3' | Mouse |
| SEQ ID NO: 32 | 5'-U CUG AGG UAG AAA GGU GAU CAU GGC UCU-3' | Mouse |
| SEQ ID NO: 33 | 5'-UU CUG AGG UAG AAA GGU GAU CAU GGC UCU-3' | Mouse |
| SEQ ID NO: 34 | 5'-GUU CUG AGG UAG AAA GGU GAU CAU GGC UCU-3' | Mouse |
| SEQ ID NO: 35 | 5'-U CUG AGG UAG AAA GGU GAU CAU GGC UCU C-3' | Mouse |
| SEQ ID NO: 36 | 5'-UU CUG AGG UAG AAA GGU GAU CAU GGC UCU C-3' | Mouse |
| SEQ ID NO: 37 | 5'-GUU CUG AGG UAG AAA GGU GAU CAU GGC UCU C-3' | Mouse |
| SEQ ID NO: 38 | 5'-U CUG AGG UAG AAA GGU GAU CAU GGC UCU CC-3' | Mouse |
| SEQ ID NO: 39 | 5'-UU CUG AGG UAG AAA GGU GAU CAU GGC UCU CC-3' | Mouse |
| SEQ ID NO: 40 | 5'-GUU CUG AGG UAG AAA GGU GAU CAU GGC UCU CC-3' | Mouse |
| SEQ ID NO: 41 | 5'-CUG AGG UAG AAA GGU GGU CAU GGC UUU-3' | Human |
| SEQ ID NO: 42 | 5'-CUG AGG UAG AAA GGU GGU CAU GGC UUU C-3' | Human |
| SEQ ID NO: 43 | 5'-CUG AGG UAG AAA GGU GGU CAU GGC UUU CC-3' | Human |
| SEQ ID NO: 44 | 5'-U CUG AGG UAG AAA GGU GGU CAU GGC UU-3' | Human |
| SEQ ID NO: 45 | 5'-AU CUG AGG UAG AAA GGU GGU CAU GGC UU-3' | Human |
| SEQ ID NO: 46 | 5'-GAU CUG AGG UAG AAA GGU GGU CAU GGC UU-3' | Human |
| SEQ ID NO: 47 | 5'-U CUG AGG UAG AAA GGU GGU CAU GGC UUU-3' | Human |
| SEQ ID NO: 48 | 5'-AU CUG AGG UAG AAA GGU GGU CAU GGC UUU-3' | Human |
| SEQ ID NO: 49 | 5'-GAU CUG AGG UAG AAA GGU GGU CAU GGC UUU-3' | Human |
| SEQ ID NO: 50 | 5'-U CUG AGG UAG AAA GGU GGU CAU GGC UUU C-3' | Human |
| SEQ ID NO: 51 | 5'-AU CUG AGG UAG AAA GGU GGU CAU GGC UUU C-3' | Human |
| SEQ ID NO: 52 | 5'-GAU CUG AGG UAG AAA GGU GGU CAU GGC UUU C-3' | Human |
| SEQ ID NO: 53 | 5'-U CUG AGG UAG AAA GGU GGU CAU GGC UUU CC-3' | Human |
| SEQ ID NO: 54 | 5'-AU CUG AGG UAG AAA GGU GGU CAU GGC UUU CC-3' | Human |
| SEQ ID NO: 55 | 5'-GAU CUG AGG UAG AAA GGU GGU CAU GGC UUU CC-3' | Human |

In another aspect, the invention provides a composition that comprises an antisense oligonucleotide of the invention, wherein the oligomeric molecule is present in an amount effective to inhibit the binding of Let-7 microRNA with its corresponding 3' untranslated region (UTR) in utrophin. In another aspect, the invention provides a composition that comprises an antisense oligonucleotide of the invention with at least one suitable excipient, for example, a pharmaceutically acceptable excipient, or an additive, known in the art.

In some embodiments, the antisense oligonucleotide is a synthetic oligonucleotide.

The antisense oligonucleotide can be synthesized by any suitable method known in the art. In some embodiments, the antisense oligonucleotide is a morpholino or phosphorodiamidate morpholino oligonucleotide (PMO) or Vivo-morpholino molecule.

Morpholinos and PMOs are known in the art and are synthetic molecules that are the product of a redesign of natural nucleic acid structure. See e.g., Summerton et al., "Morpholino Antisense Oligomers: Design, Preparation and Properties". *Antisense & Nucleic Acid Drug Development* 7 (3): 187-95. PMOs can bind to complementary sequences by standard nucleic acid base-pairing. The structural difference between morpholinos and DNA is that, while morpholinos have standard nucleic acid bases, those bases are bound to morpholine rings instead of deoxyribose rings. In addition, PMOs are linked through phosphorodiamidate groups instead of phosphates. Replacement of the anionic phosphates with the uncharged phosphorodiamidate groups eliminates ionization in the usual physiological pH range, and thus morpholinos in organisms or cells are uncharged molecules. Vivo-Morpholinos are comprised of a Morpholino oligo with a unique covalently linked delivery moiety that is comprised of an octa-guanidine dendrimer.

In other embodiments, the antisense oligonucleotide is a phosphorothioate molecule, for example, a 2'-O-methyl phosphorothioate oligoribonucleotide molecule. Phosphorothioate molecules are known in the art. These molecules include a phosphorothioate (PS) bond, which substitutes a sulfur atom for a non-bridging oxygen in the phosphate backbone of an oligo. This modification renders the internucleotide linkage resistant to nuclease degradation.

Without wishing to be bound by theory, when an antisense blocks the binding of Let-7 microRNA with its corresponding binding sequence in the 3'-UTR utrophin mRNA, the molecule is capable of enhancing utrophin production, and thereby treating Duchenne Muscular Dystrophy (DMD).

The antisense oligonucleotide may be made by any suitable method known in the art. For example, the antisense oligonucleotide is produced by a chemical process, for example by the chemical phosphoamidite method comprising sulfuration with tetraethylthiuram disulfide in acetonitrile (Tetrahedron Lett., 1991, 32, 3005-3008). In some embodiments, the antisense nucleic acid is an oligoribonucleotide molecule, for example, a 2'-O-methyl oligoribonucleotides molecule.

In another embodiment, provided herein is a method for treating or reducing the signs and symptoms associated with muscular dystrophy, in a subject, the method comprising the step of administering to said subject a composition for inhibiting utrophin microRNA molecule.

Muscular dystrophy may refer to any type of muscular dystrophy. In one embodiment, the muscular dystrophy is Duchenne Muscular Dystrophy (DMD). In another embodiment, the muscular dystrophy is Becker Muscular Dystrophy (BMD).

In another embodiment, provided herein is a method for treating a muscle disease in a subject, comprising the step of administering to said subject a composition for inhibiting utrophin microRNA molecule, thereby treating said disease in said subject.

The term "treatment" or "treating," as used herein, refers to any treatment of a disease in a mammal and includes: (1) preventing the disease from occurring in a mammal which may be predisposed to the disease but does not yet experience or display symptoms of the disease; e.g. prevention of the outbreak of the clinical symptoms; (2) inhibiting the disease, e.g., arresting its development; or (3) relieving the disease, e.g., causing regression of the symptoms of the disease.

Effective dosage for the treatment of a disease means that amount which, when administered to a mammal in need thereof, is sufficient to effect treatment, as defined above, for that disease. The method of treatment described herein can be used to treat any suitable mammal, preferably the mammal is a human.

The term "subject," as used herein, includes any human or non-human animal. The term "non-human animal" includes all vertebrates, e.g., mammals and non-mammals, such as non-human primates, sheep, dog, cow, chickens, amphibians, reptiles, etc.

In another embodiment, provided herein is a method of treating Duchene muscular dystrophy (DMD) in a subject, comprising the step of administering to said subject a composition for inhibiting utrophin microRNA molecule, thereby treating Duchene muscular dystrophy (DMD) in a subject. In another embodiment, provided herein is a method of reducing the signs and symptoms associated with Duchenne muscular dystrophy (DMD) in a subject, comprising the step of administering to said subject a composition for inhibiting utrophin microRNA molecule, thereby reducing the symptoms associated with Duchenne muscular dystrophy (DMD) in a subject.

In another embodiment, provided herein is a method of treating Becker muscular dystrophy (BMD) in a subject, comprising the step of administering to said subject a composition for inhibiting utrophin microRNA molecule, thereby treating Becker muscular dystrophy (BMD) in a subject. In another embodiment, provided herein is a method of reducing the signs and symptoms associated with Becker muscular dystrophy (BMD) in a subject, comprising the step of administering to said subject a composition for inhibiting utrophin microRNA molecule, thereby reducing the symptoms associated with Becker muscular dystrophy (BMD) in a subject.

In another embodiment, provided herein is a composition comprising an effective amount of an agent that inhibits utrophin microRNA molecule. In an exemplary embodiment, the agent comprises a let-7c antisense molecule (e.g., a sequence set forth in SEQ ID NO: 2), a miR-133b antisense molecule (e.g., a sequence set forth in SEQ ID NO: 4), a miR-150 antisense molecule (e.g., a sequence set forth in SEQ ID NO: 6), a miR-196b antisense molecule (e.g., a sequence set forth in SEQ ID NO: 8), a miR-206 antisense molecule (e.g., a sequence set forth in SEQ ID NO: 10), or a miR-296-5p antisense molecule (e.g., a sequence set forth in SEQ ID NO: 12).

In another embodiment, a composition for inhibiting utrophin microRNA molecule also induces utrophin protein production. In another embodiment, an utrophin microRNA molecule is a microRNA molecule which binds the 5' or 3'-UTR of utrophin RNA and inhibits utrophin protein production.

In another embodiment, administering a composition for inhibiting utrophin microRNA molecule comprises contacting an utrophin microRNA molecule with an utrophin microRNA antisense specific molecule. In another embodiment, a composition for inhibiting utrophin microRNA molecule comprises an utrophin microRNA antisense molecule. In another embodiment, a composition for inhibiting utrophin microRNA molecule comprises an utrophin microRNA antisense specific molecule. In another embodiment, a composition for inhibiting a muscle cell specific microRNA molecule comprises an utrophin microRNA antisense specific molecule.

In another embodiment, a composition for inhibiting utrophin microRNA molecule is administered to a muscle cell in a subject. In another embodiment, a composition for inhibiting utrophin microRNA molecule is administered to a subject and is targeted to a muscle cell.

In another embodiment, the method of the present invention reduces signs and symptoms associated with Duchenne muscular dystrophy (DMD) or Becker muscular dystrophy (BMD). In another embodiment, the method of the present invention improves walking of a DMD or BMD patient. In another embodiment, the method of the present invention reduces or inhibits calves swelling with fibrous tissue. In another embodiment, the methods of the present invention induce muscle growth. In another embodiment, the methods of the present invention induce muscle regeneration. In another embodiment, the method of the present invention reduces or inhibits contractures. In another embodiment, the method of the present invention reduces or inhibits scoliosis. In another embodiment, the method of the present invention reduces or inhibits diaphragm weakening. In another embodiment, the method of the present invention reduces or inhibits a cardiac disease caused by or associated with lack of dystrophin.

The inhibitors of the present invention and pharmaceutical compositions comprising same can be administered to a subject by any suitable method known in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally. In some embodiments, administration is systemic. In some embodiments, administration is intramuscular.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelatin capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in the composition of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g.

hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which of the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In one embodiment, the methods of the present invention comprise administering an active compound as the sole active ingredient. However, also encompassed within the scope of the present invention are methods for treating diseases and disorders that comprise administering the active compound in combination with one or more other therapeutic agents. These agents include, but are not limited to, insulin agents, immunosuppressive agents, or drugs treating MS. In another embodiment, these agents are appropriate for the disease or disorder that is being treated, as is well known in the art.

EXAMPLES

Example 1: Utrophin-A is Translated Inefficiently

Figure 2:
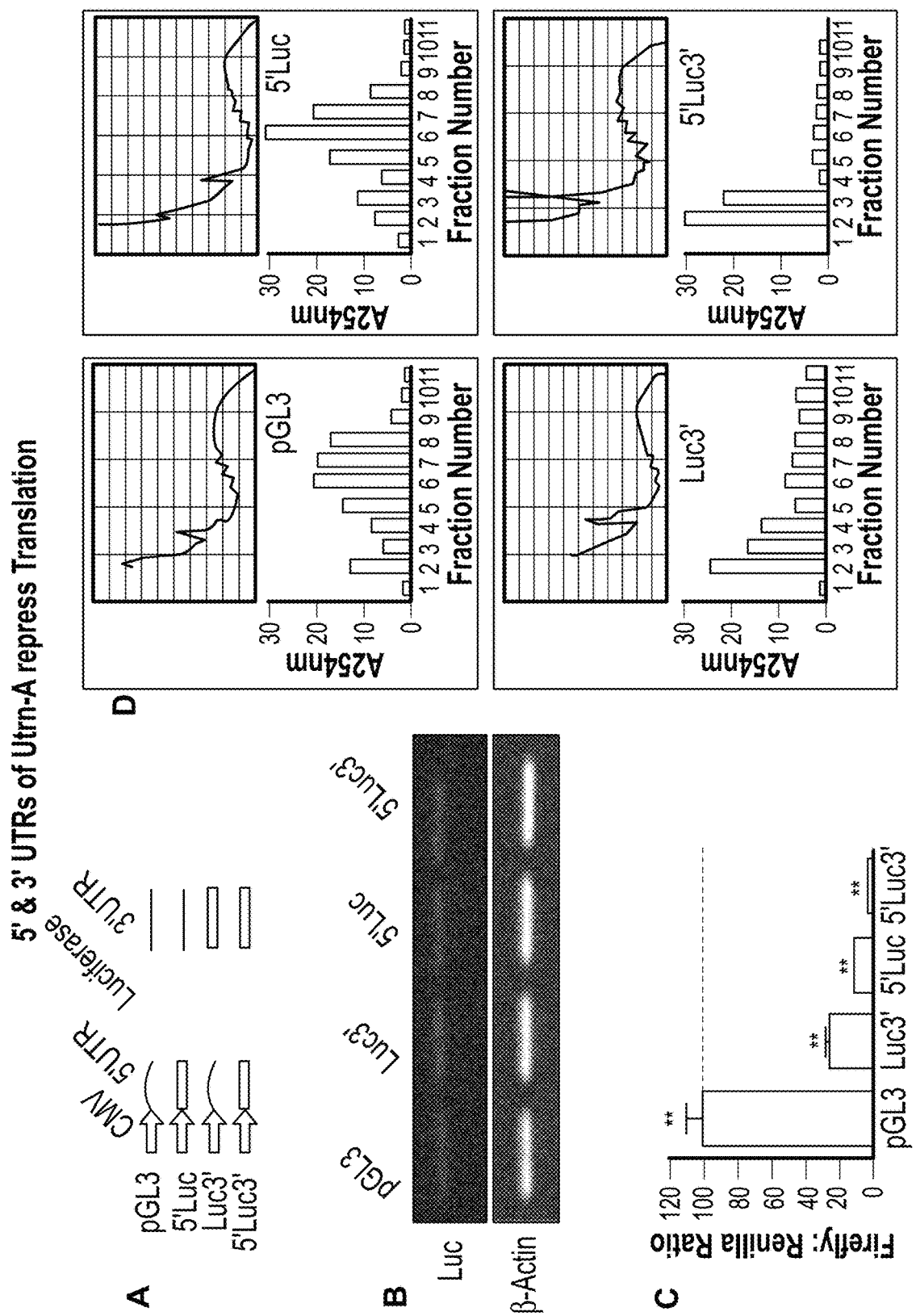
FIG. 2 shows that C2C12 cells were transfected with luciferase reporter constructs (A and B) and the mRNA levels and luciferase activity were analyzed (C). Also, C2C12 cell extract was resolved on a sucrose density gradient, collected into eleven fractions, and the target mRNA level in each fraction was determined by q-PCR analysis (D).
Figure 3:
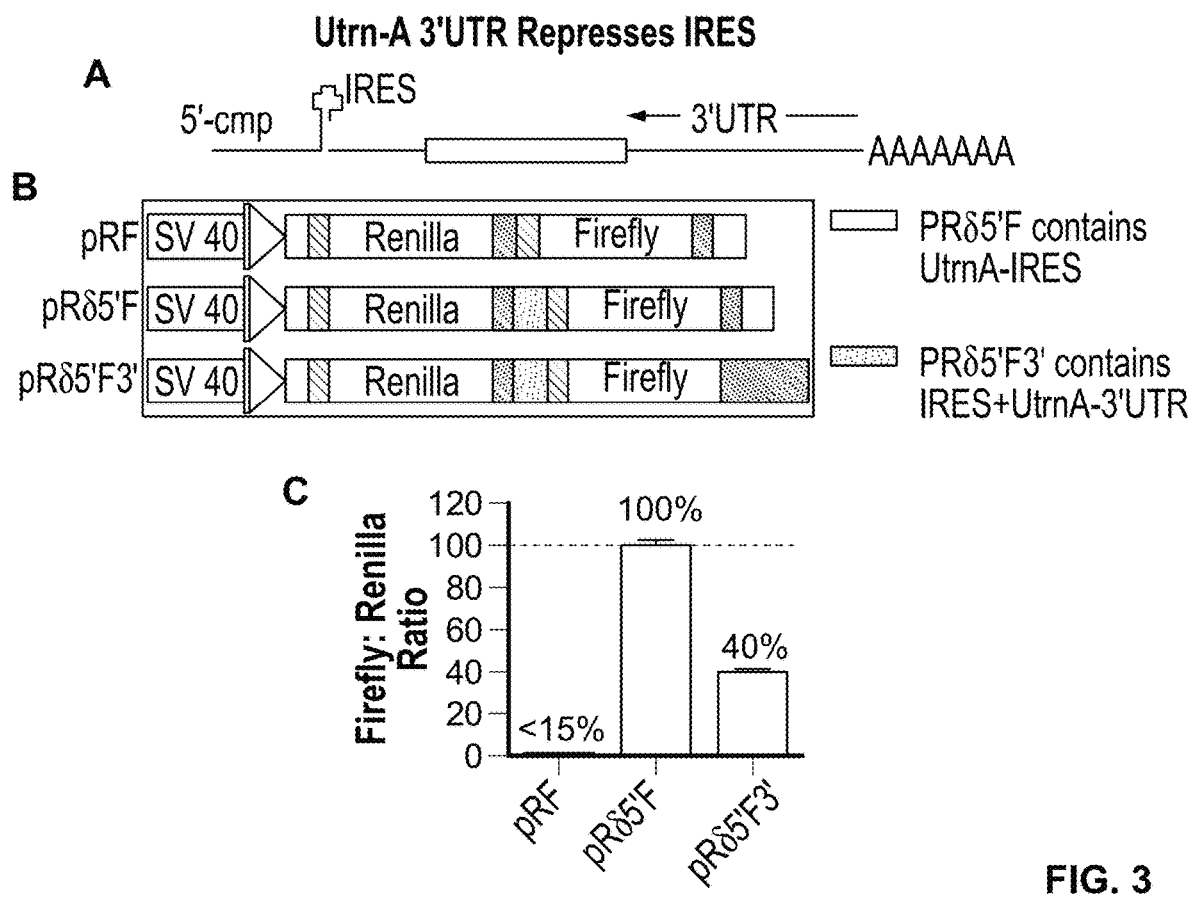
FIG. 3 shows that Utrophin 3'-UTR represses IRES. (A) is a schematic representation of utrophin-A mRNA. 3 bicistronic constructs comprising control, utrophin IRES or utrophin IRES plus utrophin 3'-UTR. (B) A bar graph showing the ratio of expression from the two cistrons, under the control of the 3 different constructs.
Figure 10:
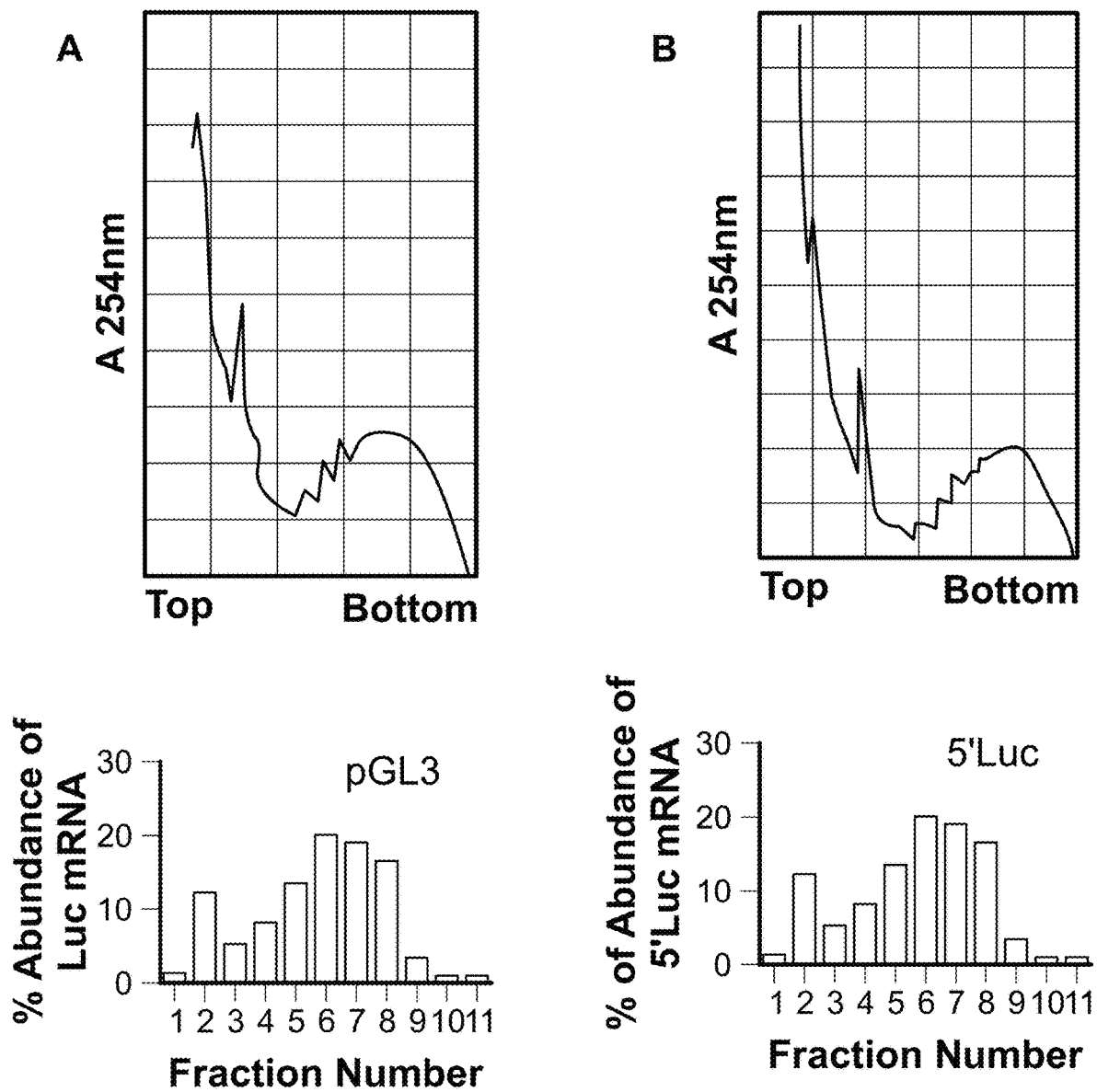
FIG. 10 shows that C2C12 cell extract was resolved on a sucrose density gradient, collected into eleven fractions, and the target mRNA level in each fraction was determined by q-PCR analysis and quantified as shown in the bar graphs for the constructs of FIG. 1.
Figure 11A:
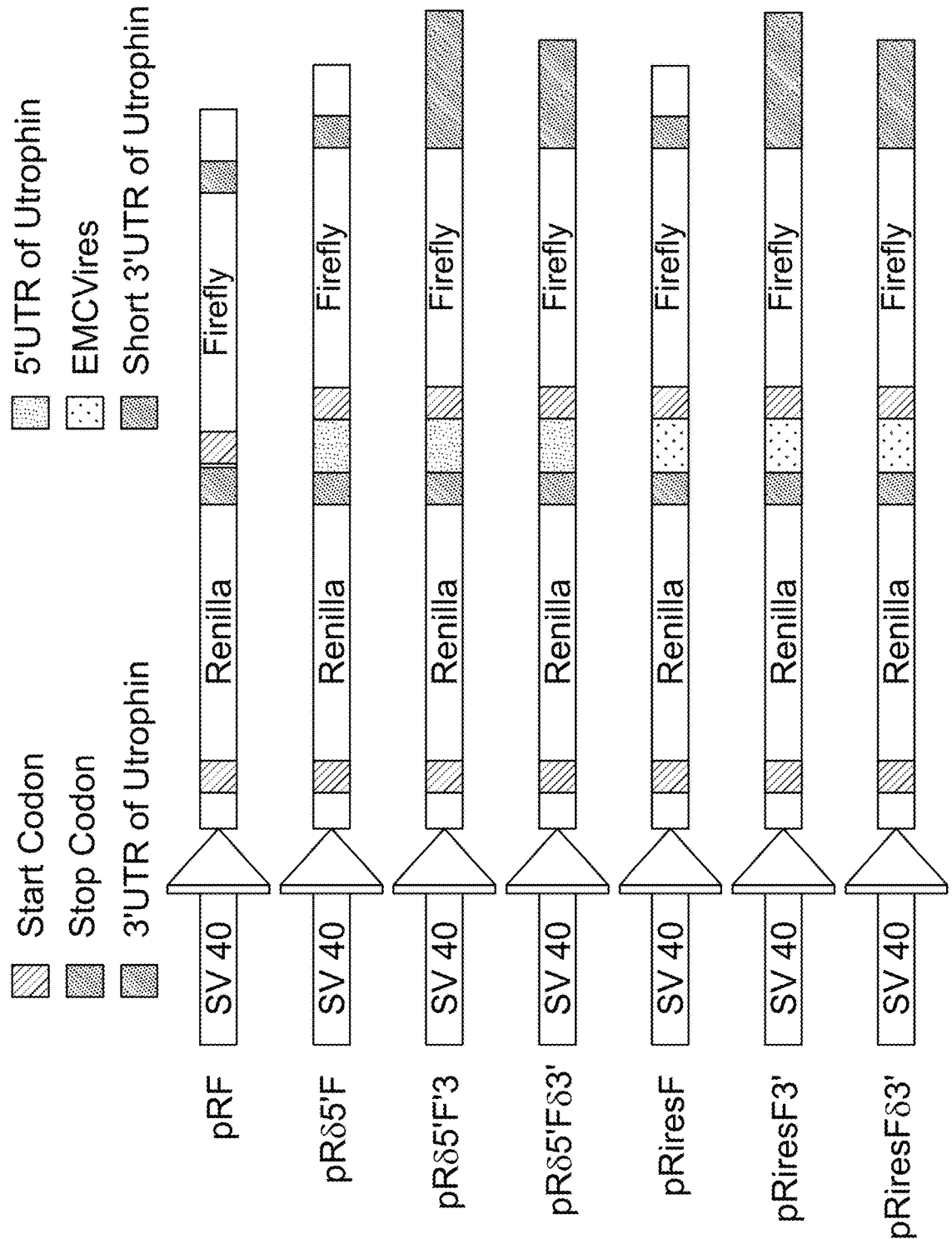
FIG. 11 shows that Utrophin 3'-UTR represses IRES. The 7 bicistronic constructs comprising control, or utrophin-A or EMCV IRES with and without the utrophin 3'-UTR(A). Bar graphs showing the ratio of firefly/*renilla* expression from the two cistrons, under the control of the 7 different construct (B and C).
Figure 11B:
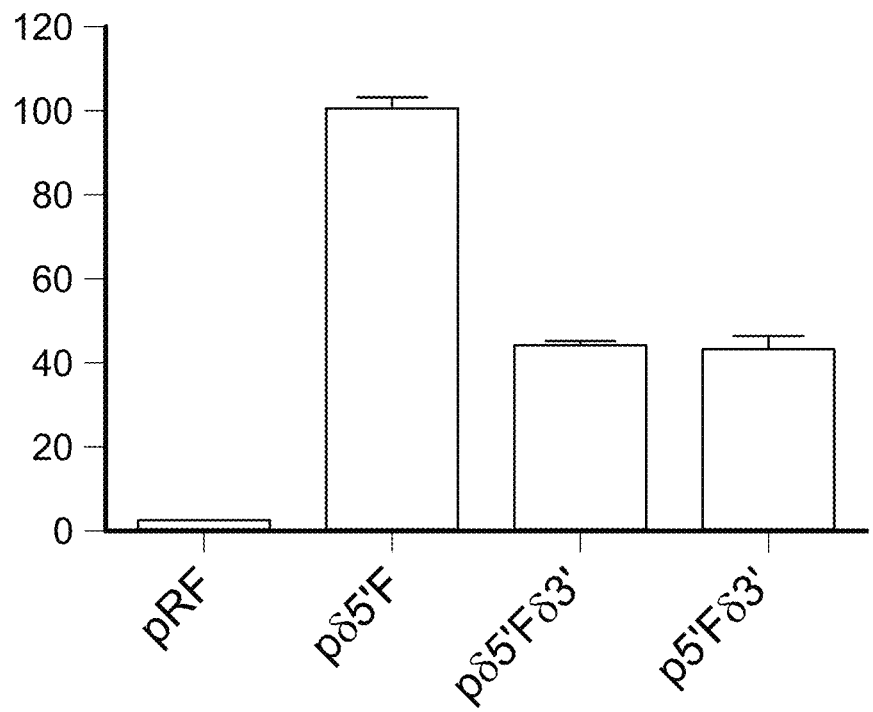
Figure 11C:
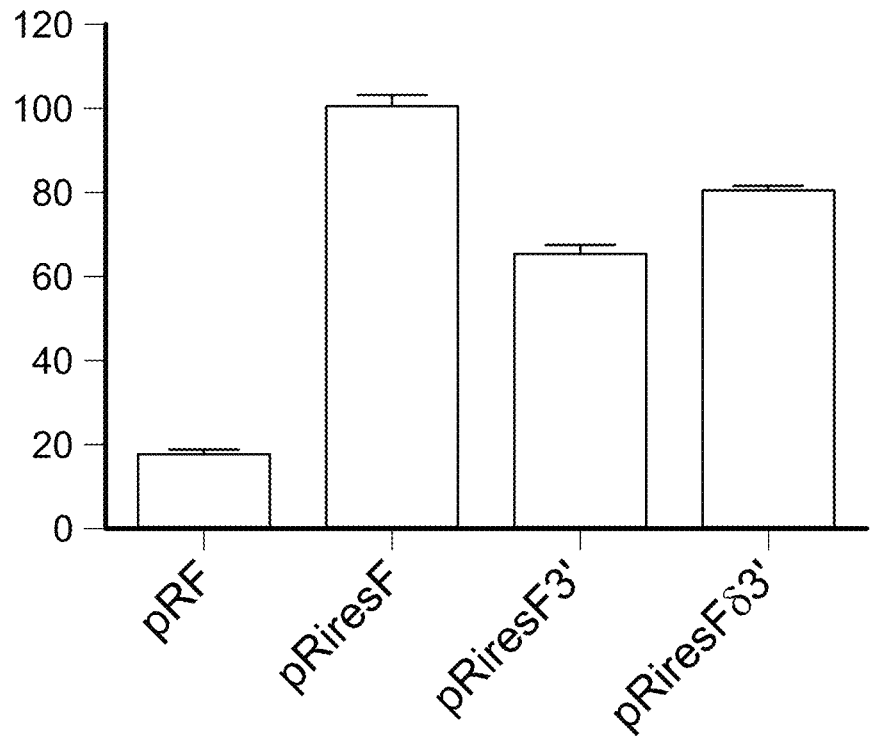

Ribosomal profiling of utrophin-A mRNA in C2C12 muscle cell line by a sucrose gradient provided that utrophin-A is translated inefficiently (FIG. 1). This observation led to an experiment wherein the 5' and 3'-UTRs were dissected in order to confirm that utrophin-A non-coding regions are responsible for the translation repression observed. An experiment wherein the 5' or the 3'-UTR was cloned into a reporter gene construct (luciferase) showed that these non-coding regions are indeed responsible for this inefficient utrophin-A translation (FIGS. 2 and 10).

Example 2: MicroRNA Candidates

Figure 5:
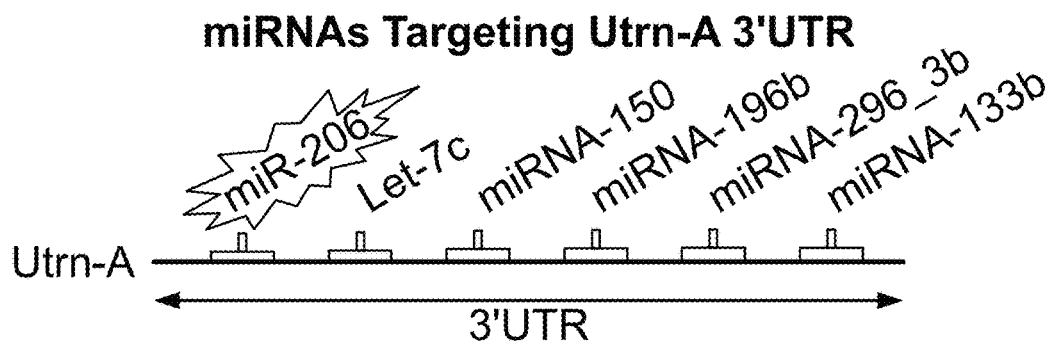
FIG. 5 is a schematic representation of utrophin 3'-UTR microRNA binding sites.

MicroRNA candidates were predicted to target utrophin RNA using the miRanda v1.0.b algorithm. The expression of the predicted microRNAs was confirmed in C2C12 cells or TA by Taqman microRNA assay (FIG. 5).

Example 3: Utrophin-A Repression by MicroRNA

Figure 4:
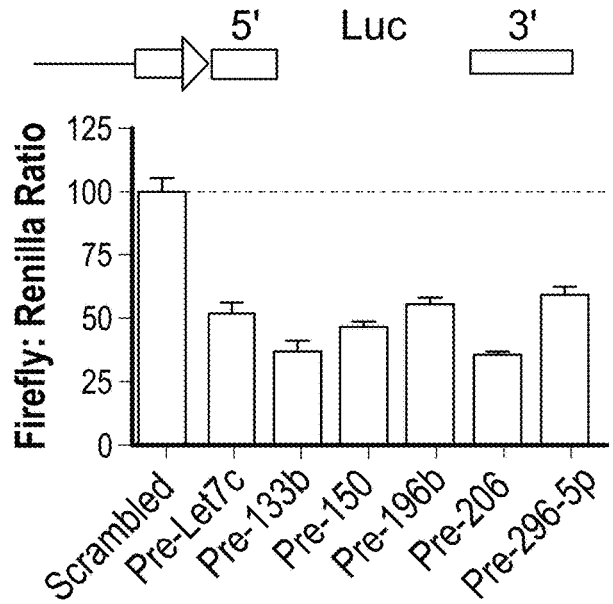
FIG. 4 is a graph showing a decrease in light produced (due to luciferase) on addition of different microRNAs.
Figure 12A:
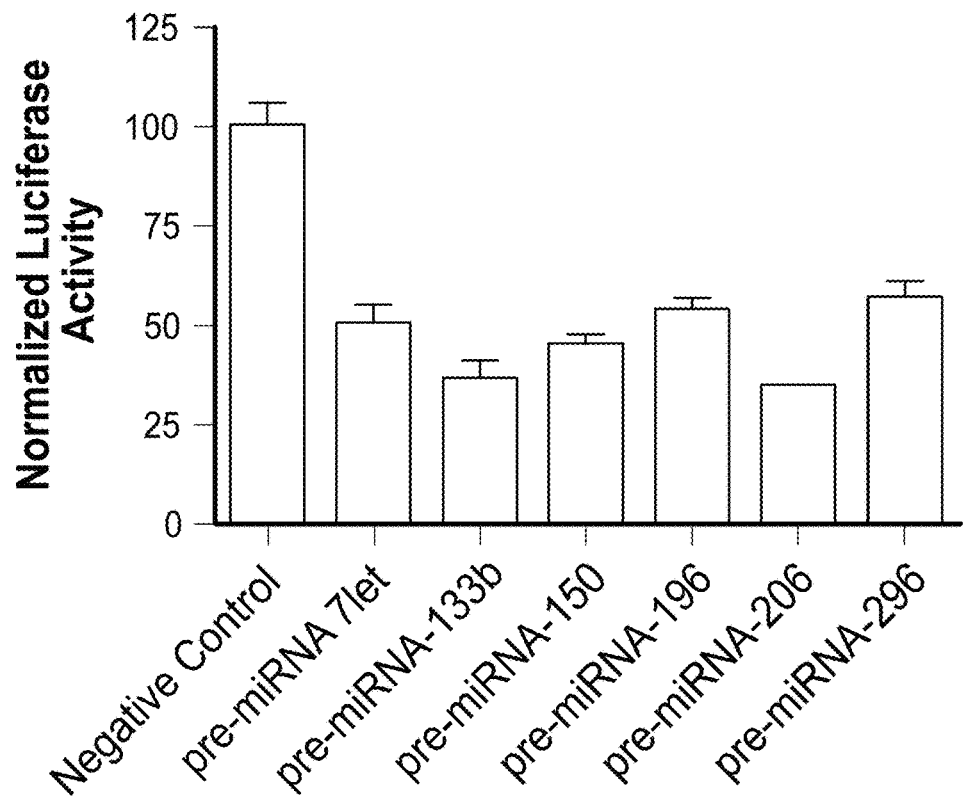
FIG. 12 is a graph showing a decrease in light produced by utrophin UTR-luciferase construct (A) and firefly/*renilla* expression by utrophin UTR-firefly construct (C) on addition of different microRNAs. (B) A graph showing an increase in light produced (due to luciferase) on inhibition of certain microRNAs.
Figure 12B:
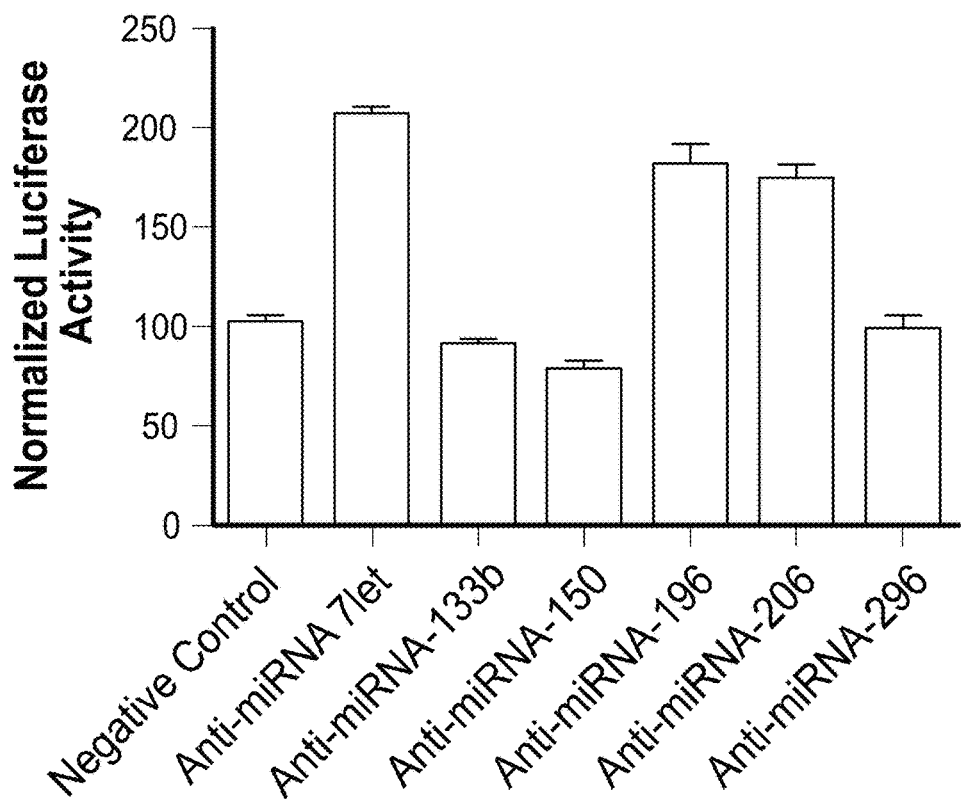
Figure 12C:
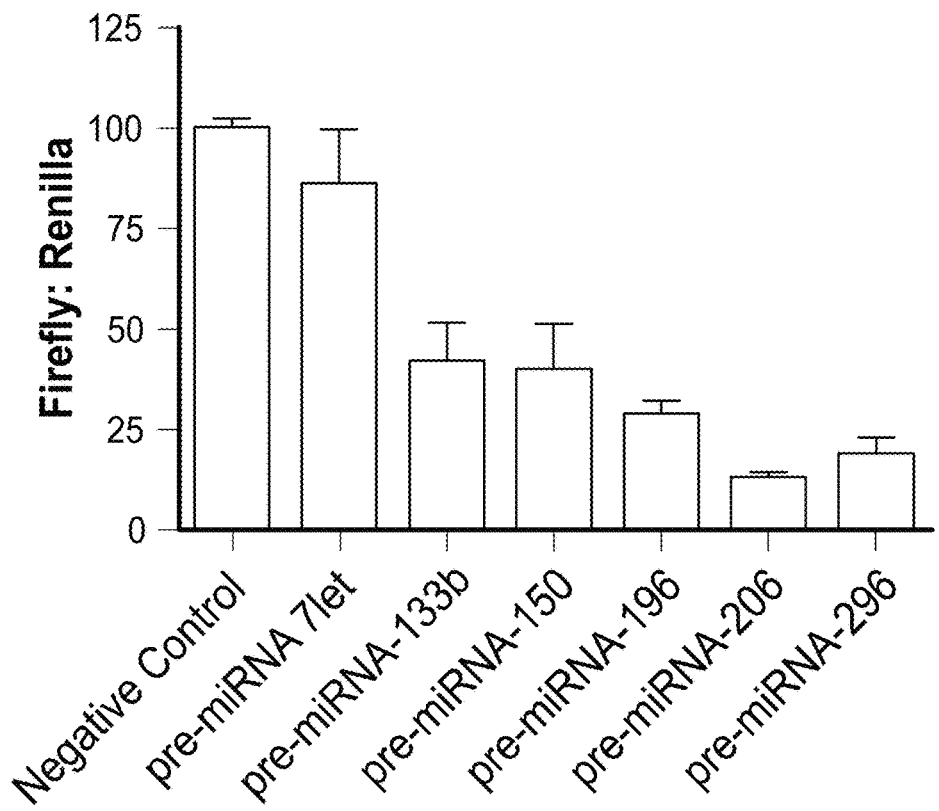
Figure 13:
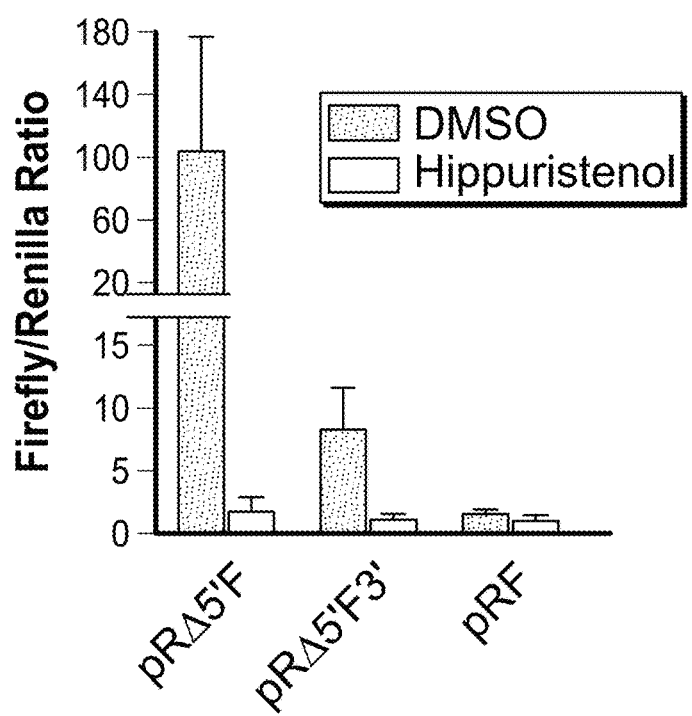
FIG. 13 shows that Utrophin-A IRES requires eIF4A. 3 bicistronic constructs comprising control, or utrophin-A IRES with and without the utrophin 3'-UTR. The bar graph shows the firefly/*Renilla* ratio in cells transfected with plasmids comprising the constructs provided in FIG. 9 with and without the eIF4A inhibitor hippuristanol.
Figure 14:
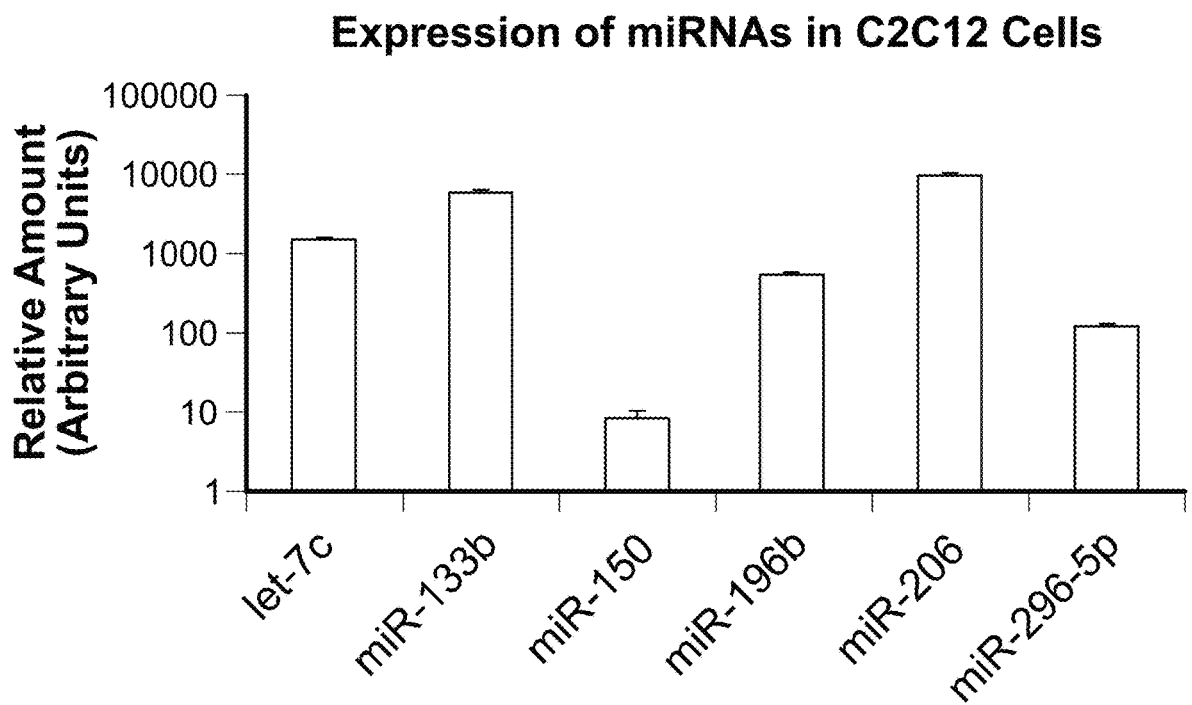
FIG. 14 shows detection and relative quantification of microRNAs in C2C12 muscle cells by miRNA TaqMan assays.
Figure 15:
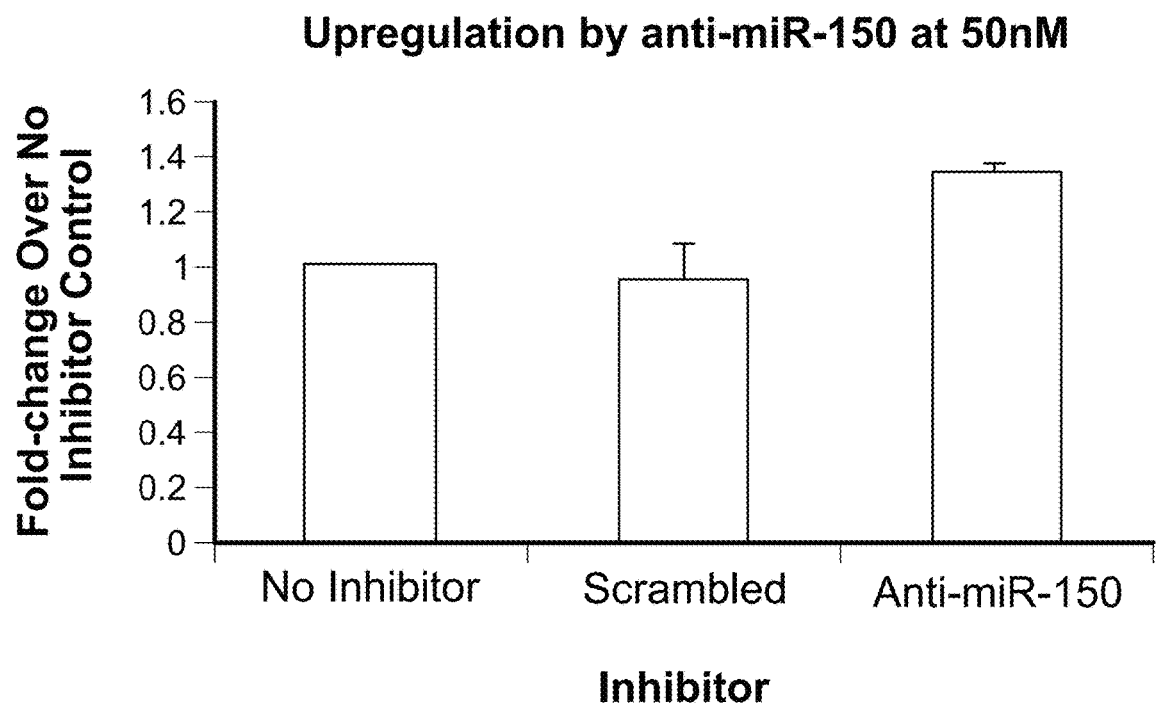
FIG. 15 shows upregulation of luciferase expression by 5'Luc3' construct on treatment of miR-150 inhibitor at a lower concentration (50 nM).

C2C12 cells were transfected with a plasmid comprising a construct containing the 5'-UTR of the utrophin-A mRNA, a luciferase reporting gene, and the 3'-UTR of the utrophin mRNA as described in Example 1. The transfected cells were treated with pre-Let-7c, pre-miR-133b, pre-miR-150, pre-miR-196b, pre-miR-206, pre-miR-296-5p, or a scrambled control sequence. As shown in FIGS. 4 and 12 the scrambled control sequence did not affect luciferase translation, still all 6 microRNA constructs repressed luciferase translation. Thus, Let-7c, miR-133b, miR-150, miR-196b, miR-206, and miR-296-5p are able to repress the translation of a gene comprising the 5'-UTR of the utrophin-A mRNA and the 3'-UTR of the utrophin mRNA. This experiment demonstrated that Let-7c, miR-133b, miR-150, miR-196b, miR-206, and miR-296-5p are responsible for the repression of utrophin-A mRNA translation. Thus, both 5' and 3'-UTRs play an important role in utrophin-A translational repression and the 3'-UTR preferentially represses IRES-mediated translation. Moreover, this experiment demonstrates that the 5'-UTR of the utrophin-A mRNA and the 3'-UTR of the utrophin mRNA are required for the microRNA induced repression.

Example 4: Utrophin is Upregulated by MicroRNA Repression

Figure 6:
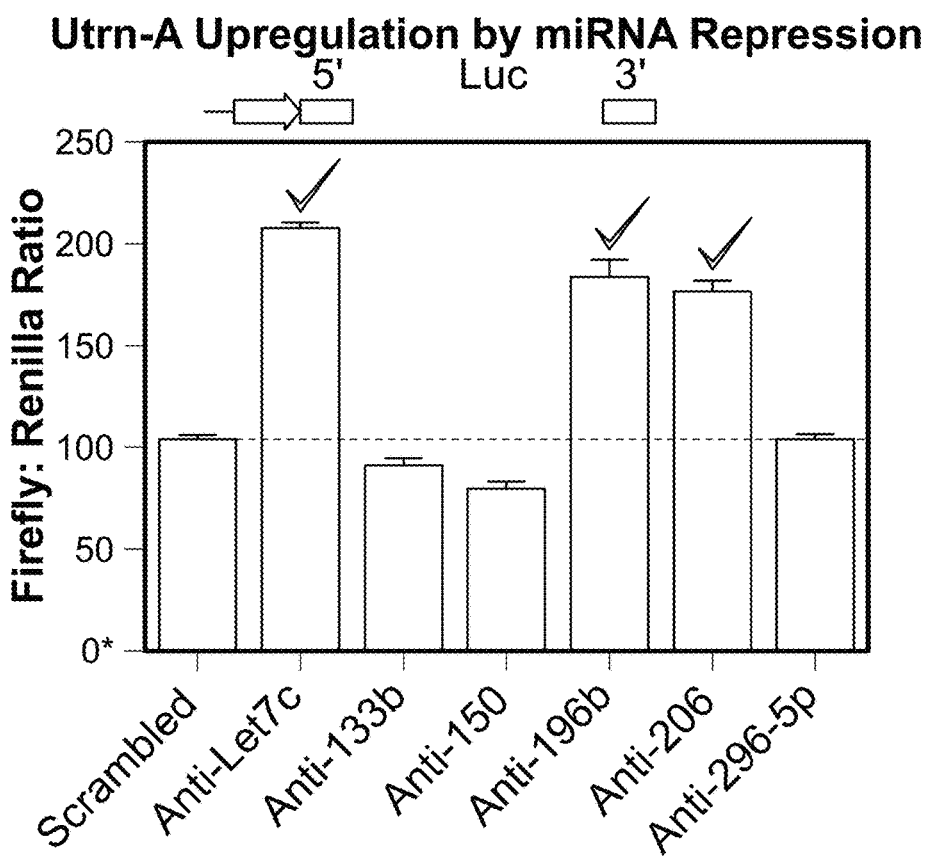
FIG. 6 is a graph showing an increase in light produced (due to luciferase) on inhibition of certain microRNAs.
Figure 7:
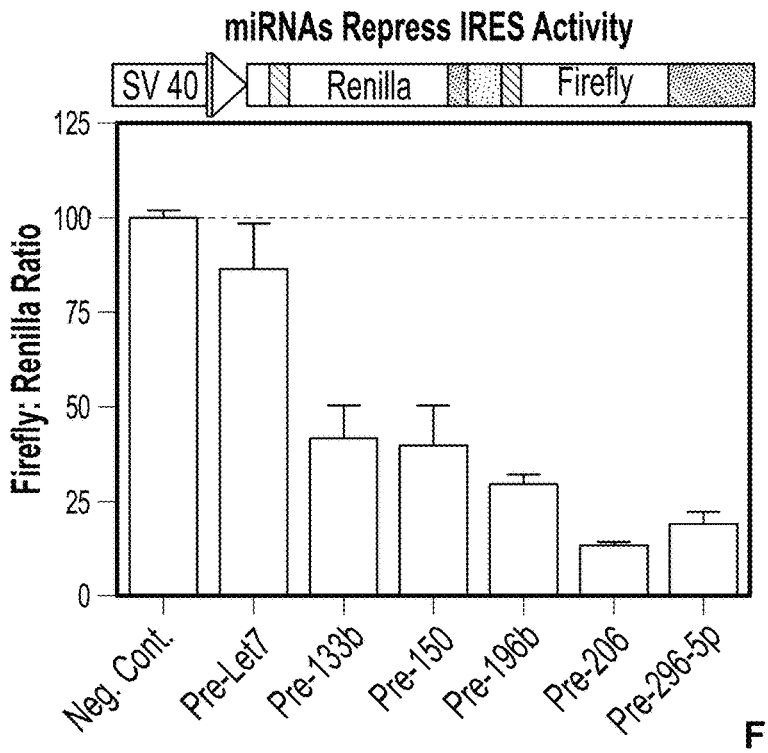
FIG. 7 is a graph showing the IRES repression activity by microRNA molecules that bind utrophin 3'-UTR on a reporter gene comprising the utrophin 3'-UTR.
Figure 8:
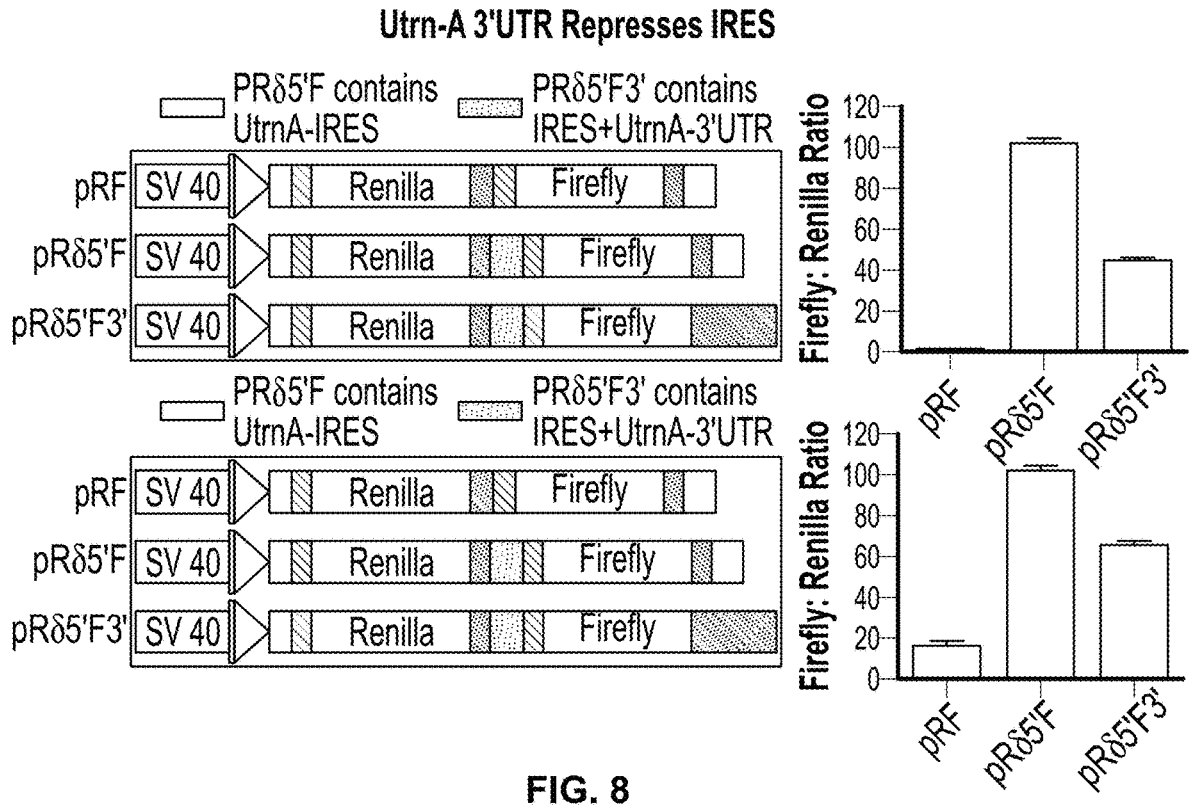
FIG. 8 shows that Utrophin 3'-UTR represses IRES. 5 bicistronic constructs comprising control, or utrophin-A or EMCV IRES with and without the utrophin 3'-UTR. 2 bar graphs showing ratio of expression of the two cistrons for each construct.
Figure 9:
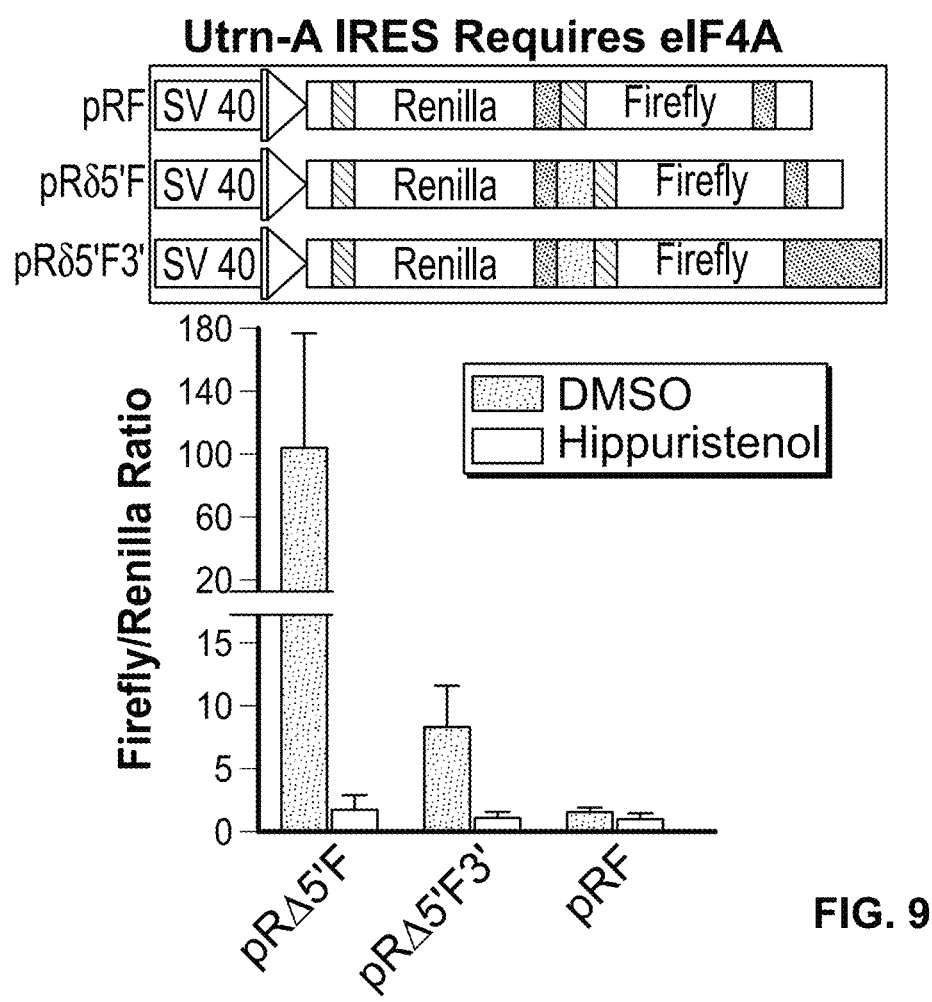
FIG. 9 shows that Utrophin-A IRES requires eIF4A. 3 bicistronic constructs comprising control, or utrophin-A IRES with and without the utrophin 3'-UTR. (B) A bar graph showing ratio of expression of the two cistrons for each construct with and without the eIF4A inhibitor hippuristanol.

C2C12 cells were transfected with a plasmid comprising a construct containing the 5'-UTR of the utrophin-A mRNA, a luciferase reporting gene, and the 3'-UTR of the utrophin mRNA as described in Examples 1 and 3. The transfected cells were treated with antisense sequences: anti-Let-7c, anti-miR-133b, anti-miR-150, anti-miR-196b, anti-miR-206, anti-miR-296-5p, or a scrambled control sequence. The results shown in FIGS. 6 and 12 demonstrate that the scrambled control sequence did not affect luciferase translation; still anti-Let-7c, anti-miR-196b, anti-miR-206, induced luciferase translation. Thus, neutralizing Let-7c, miR-196b, or miR-206 induce the translation of a gene comprising the 5'-UTR of the utrophin-A mRNA and the 3'-UTR of the utrophin mRNA. This experiment demonstrates that utrophin-A can be induced (upregulated) by at least 2 folds by neutralizing Let-7c, miR-196b, or miR-206 that act as repressors on the UTR segments of the utrophin mRNA. This experiment also provides that this upregulating sequence specific as specific microRNAs did not upregulate utrophin expression including miR-150, miR-133b and miR-296-5p.

The sequence of the negative control inhibitor is: 5'-AAGUGGAUAUUGUUGCCAUCA-3' (SEQ ID NO: 20) and the sequences of the scrambled pre-miRNA are: sense: 5'-AGUACUGCUUACGAUACGGtt-3' (SEQ ID NO: 21), and antisense: 5'-CCGUAUCGUAAGCAGUA-CUtt-3' (SEQ ID NO: 22).

Utrophin has two isoforms, A and B. They have different 5'-UTRs but the 3'-UTRs are the same. Therefore, any mechanism targeting the 3'-UTR would be effective for upregulation of either isoform. Utrophin-A and utrophin-B are very similar and either should be effective as a therapy. Accordingly, the results demonstrate the upregulation of both Utrophin-A and utrophin-B isoforms.

Example 5: Translational Regulation of Utrophin by miRNAs

Utrophin is the autosomal homolog of dystrophin, the product of the Duchenne Muscular Dystrophy (DMD) locus. Its regulation is of therapeutic interest as its overexpression can compensate for dystrophin's absence in animal models of DMD. The tissue distribution and transcriptional regulation of utrophin have been characterized extensively, and more recently translational control mechanisms that may underlie its complex expression patterns have begun to be identified.

Using a variety of bioinformatic, molecular and cell biology techniques, we show that the muscle isoform utrophin-A is predominantly suppressed at the translational level in C2C12 myoblasts. The extent of translational inhibition is estimated to be ~99% in C2C12 cells and is mediated by both the 5'- and 3'-UTRs of the utrophin-A mRNA. In this study we identify five miRNAs (let-7c, miR-150, miR-196b, miR-296-5p, miR-133b) that mediate the repression, and confirm repression by the previously identified miR-206. We demonstrate that this translational repression can be overcome by blocking the actions of miRNAs, resulting in an increased level of utrophin protein in C2C12 cells.

The present study has identified key inhibitory mechanisms featuring miRNAs that regulate utrophin expression, and demonstrated that these mechanisms can be targeted to increase endogenous utrophin expression in cultured muscle cells. Our results indicate that miRNA-mediated inhibitory mechanisms could be used for increasing utrophin expression as a therapy for DMD.

Materials and Methods
miRNA Prediction
miRNAs targeting the utrophin 3'-UTR were predicted using the miRanda v1.0b algorithm, with a cut-off for predictions of a score greater than 100 and minimum free energy of −14 kcal/mol.

Constructs
The mouse utrophin-A 5'-UTR was amplified with primers 5'CCATGGGATCCACGGCTCCGAGG3' (SEQ ID NO.: 80) and 5'CCATGGCTTGAATGAGTTTCAG TATAATCCAAAG3' (SEQ ID NO.: 81) and cloned upstream of luciferase at the NcoI site of pGL3 to construct 5'Luc. Cloning of the 5'-UTR at the NcoI site converted the poor Kozak consensus of aagATGG for native utrophin-A into a good Kozak consensus of gccATGG. pGL3 also contains a good Kozak sequence, accATGG. A ScaI-BamHI digested fragment of Riken clone 9430078L05 (NCBI Accession #AK035043) containing the mouse utrophin 3'-UTR was cloned at the XbaI site of pGL3 and 5'Luc by blunt end ligation to construct Luc3' and 5'Luc3', respectively. The final constructs contain the full 2.4 kb mouse utrophin 3'-UTR preceded by the final 200 bases of utrophin coding sequence.

Cell Culture
The mouse muscle C2C12 and human HeLa cell lines (both from ATCC) were cultured in DMEM with 10% FBS, glutamine, penicillin and streptomycin.

Transfection
All transfections were done with Lipofectamine 2000 (Invitrogen) according to the manufacturer's protocol. For 2OMePS transfections, the ratio was reduced to 1:1 1 Lipofectamine 2000:µg oligomer.

Ribosomal Profiling
C2C12 cells (70% confluent) were transfected with constructs in 100 mm dishes. Media was changed after 6 hours. Cycloheximide (final concentration 100 µg/ml) was added 24 post-transfection and incubated for 15 minutes at 37° C. Cells were washed twice with ice cold PBS, lysed in 300 µl ice cold lysis buffer (110 mM potassium acetate, 2 mM magnesium acetate, 10 mM HEPES [pH 7.5], 50 mM potassium chloride, 10 mM magnesium chloride, 2 mM DTT, 1% NP-40, 1% deoxycholate, complete-mini protease inhibitors (Roche), 500 U/ml RNasin, and 100 µg/ml cycloheximide), scraped into a tube, homogenized by passing 8 times through a 23 gauge needle at 4° C. and centrifuged (10 minutes, 14000 rpm). Supernatants were layered onto 11 ml of a 15-50% linear sucrose gradient and centrifuged (36000 rpm, 2 hours). Gradients were fractionated by upward displacement with 60% sucrose and absorbance monitored continuously at 254 nm. RNA was isolated from each fraction with Trizol (Invitrogen) and treated with DNaseTURBO (Ambion) followed by treatment with DNase-free (Ambion). RNA was reverse transcribed with random hexamers using the SuperScript First Strand Synthesis System (Invitrogen), according to the manufacturer's instructions. Utrophin-A mRNA copy number was quantified from 10 µl cDNA with 0.05 nM each of primers 5'ATCCAT-TTGGTAAAGGTTTTCTTCTG3' (SEQ ID NO.: 82) and 5'ACGAATTCAGTGAC ATCATTAAGTCC3' (SEQ ID NO.: 83) and Tamra-labeled 5'ATCATTGTGTTCATCA-GATC3' (SEQ ID NO.: 84) MGB probe (0.25 µM) in TaqMan mix (Applied Biosystems). A standard curve was generated from dilutions of a clone containing a unique region of the utrophin-A cDNA, amplified with primers 5'GCGTGCAGTGGACCATTTTTCAGATTTA3' (SEQ ID NO.: 85) and 5'GCGTGCA GATCGAGCGTTTATCCAT-TTG3'(SEQ ID NO.: 86). β-actin was quantified using pre-mixed reagents (Ambion). A standard curve was generated from dilutions of a β-actin cDNA clone amplified with primers 5'TTCTTTGCAGCTCCTTCGTTG3' (SEQ ID NO.: 87) and 5'TCAAGTCAG TGTACAGGCCAGC3' (SEQ ID NO.: 64). Luciferase transcript levels in transfected cells were determined by SYBR Green qPCR using 5 µl cDNA with 10 pmol primers 5'AAAGTTGCGCGGAG-GAGTT3' (SEQ ID NO.: 65) and 5'CCCTTCTTGGCCTT-TATGAGG3' (SEQ ID NO.: 66) (firefly luciferase) or 5'ATCGGACCCAGGATTCTTTTC3' (SEQ ID NO.: 67) and 5'CCATTTCATCAGGTGCATCT3' (SEQ ID NO.: 68) (*Renilla* luciferase) in SYBR Green PCR mix (Applied Biosystems). A standard curve was generated using dilutions of pGL3 (firefly luciferase) or pRL-TK (*Renilla*).

Luciferase Reporter Assay

C2C12 cells were plated in 24 well plates, 40,000 cells per well, 1 day before transfection. 400 ng pGL3 (1600 ng for 6-well plates) or equimolar amounts of other constructs were transfected, with 50 ng pRL-TK (Promega), per well. Reporter activity was measured by Dual Luciferase Assay (Promega) 6 or 24 hours after transfection.

RT-PCR for Luciferase and β-Actin

RNA was isolated using an RNeasy kit (Qiagen) and reverse-transcribed with random hexamers using the Super-Script First Strand Synthesis System (Invitrogen), according to the manufacturer's instructions. PCR amplification was done using primers 5'AAAGTTGCGCGGAGGAGTT3' (SEQ ID NO.: 65) and 5'CCCTTCTTGGCCTTTAT-GAGG3' (SEQ ID NO.: 66) for luciferase or 5'CGTGCGTGACATCAAAGAGAAGC3' (SEQ ID NO.: 69) and 5'CCCAAGAAGGAAGGCTGGAA AAG3' (SEQ ID NO.: 70) for β-actin.

Pre-miRNAs and miRNA Inhibitors

Pre-miRNAs or miRNA antisense inhibitors (Ambion) were transfected into C2C12 cells with 680 ng 5'Luc3' and 50 ng pRL-TK per well in 24-well plates. Pre-miRNAs for hsa-let-7c (PM10436), hsa-miR-133b (PM10029), hsa-miR-150 (PM10070), hsa-miR-196b (PM12946), hsa-miR-206 (PM10409) and hsa-miR-295-5p (PM10609) were used, with a scrambled pre-miRNA (pre-miRNA negative control #1). Inhibitors of hsa-let-7c (AM10436), hsa-miR-133b (AM1 0029), hsa-miR-150 (AM10070), hsa-miR-196b (AM12946), hsa-miR-206 (AM10409) and hsa-miR-295-5p (AM10609) were used, all targeting both human and mouse miRNAs, or scrambled inhibitor anti-miR negative control #1. The 2OMePS oligomer designed to block the let-7 target site in the utrophin 3'-UTR had the sequence CUGAGGUA-GAAAGGUGAUCAUGGCUC (SEQ ID NO: 24) while the inactive control 2OMePS had the sequence GUGAGCAC-UUCUUUCCUUCUUUUUU (SEQ ID NO.: 71).

miRNA Isolation, Reverse-Transcription and TaqMan Quantitative Real-Time PCR Analysis An RNeasy Plus Kit (Qiagen) and provided supplementary protocol and a miRVana kit (Ambion) were used to prepare total RNA, containing miRNA, from skeletal muscles (tibialis anterior (TA) and soleus) of adult Black10 mice and C2C12 cells, respectively. RNA quality was estimated with a NanoDrop ND-1000 Spectrometer (Thermo Scientific). 10 ng (skeletal muscles) or 320 ng (C2C12 cells) total RNA was converted to cDNA using TaqMan miRNA Assay primers and TaqMan miRNA Reverse Transcription Kit (both Applied Biosystems).

Targeted Sequences:

```
                                    (SEQ ID NO: 1)
let-7c      UGAGGUAGUAGGUUGUAUGGUU (SEQ ID NO: 3)
miR-133b    UUUGGUCCCCUUCAACCAGCUA (SEQ ID NO: 5)
miR-150     UCUCCCAACCCUUGUACCAGUG
```

-continued

```
                                    (SEQ ID NO: 7)
miR-196b    UAGGUAGUUUCCUGUUGUUGG (SEQ ID NO: 9)
miR-206     UGGAAUGUAAGGAAGUGUGUGG (SEQ ID NO: 11)
miR-296-5p  AGGGCCCCCCCUCAAUCCUGU
```

Quantitative PCR (qPCR) was performed on a ABI PRISM 7900HT Real-Time PCR system (Applied Biosystems), and data analyzed with SDS.2.3 software. Expression levels of miRNAs were normalized to the endogenous control RNU6 in skeletal muscle, and the endogenous control sno202 in C2C12 cells (both assays from Ambion).

Western Blotting

Cell lysates were prepared by scraping with TNEC lysis buffer (1.5 mM Tris-HCl pH 8, 2.15 mM NaCl, 3.1% Igepal CA630, 4.2 mM EDTA with Complete protease inhibitors (Roche)), incubating on ice for 20 minutes then centrifuging at 13 000 rpm in a benchtop centrifuge at 4° C. and removing and retaining supernatants. Protein concentration was assayed using a DC protein assay (Bio-Rad). 60-65 µg protein were combined with LDS sample buffer and NuPAGE reducing reagent (both Invitrogen) and heated to 99° C. in for 5 minutes, then separated on 3-8% Tris-Acetate gels (Invitrogen) with TA running buffer for 2 hours 15 minutes at 80 V. Proteins were transferred to PVDF membranes for overnight at 35 V, 4° C. in ice-cooled transfer buffer (25 mM Tris pH 8.3, 192 mM glycine, 20% methanol, 0.05% sodium dodecyl sulphate). Membranes were blocked for 1 hour at room temperature in 5% non fat milk in TBS (50 mM Tris pH 7.5, 150 mM NaCl), then probed for utrophin (upper half of membrane) with mouse monoclonal anti-utrophin antibody mancho 3 clone 8A4 (developed by Glenn E. Morris and obtained from the Developmental Studies Hybridoma Bank developed under the auspices of the NICHD and maintained by The University of Iowa Department of Biology) diluted 1:50 in 5% non fat milk in TBST (TBS with 0.05% Tween 20), or tubulin (lower half of membrane) with anti-alpha-tubulin antibody clone DM1A (Sigma) diluted 1:5000 in 5% non fat milk in TBS, for 1 hour at room temperature. Membranes were washed in 3 changes of TBST for 10 minutes each, then incubated with HRP-conjugated goat-anti-mouse IgG (Jackson ImmunoResearch), diluted 1:4000 in 5% non fat milk in TBS (for utrophin) or TBS (for utrophin), for 1 hour at room temperature. TBST washes were repeated, then bands were visualized using SuperSignal West Pico Chemiluminescent Substrate (Thermo Scientific) and images obtained using an LAS-3000 Imager (Fujifilm). For presentation clarity, images were then inverted to give dark bands on a light background. Band densities were quantified using ImageJ (www.rsbweb.nih.gov/ij/index.html).

Results

Figure 16:
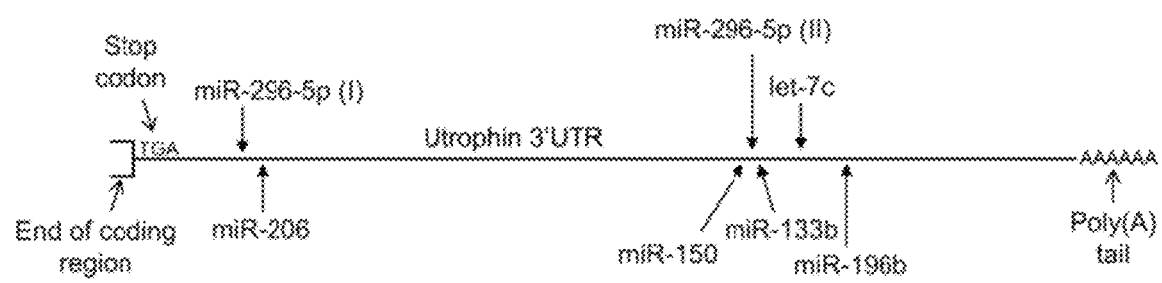
FIG. 16. Six miRNAs are predicted to target the utrophin 3'-UTR. The miRanda v1.0b algorithm was used to predict miRNAs that target the utrophin 3'-UTR. Six miRNAs (miR-296-5p, miR-206, miR-150, miR-133b, let-7c, and miR-196b) were strong candidates and their predicted target sites within the utrophin 3'-UTR are represented diagrammatically. Note that miR-296-5p has two putative binding sites, as shown.

Bioinformatic Predictions of miRNAs Targeting the Utrophin 3'-UTR miR-206 is the only miRNA that had been reported to target utrophin. However, the very large size (2.4 kb) of the utrophin 3'-UTR suggests it could be a target of several regulatory miRNAs. Therefore, we used the miRanda v1.0b algorithm to predict miRNAs that target the utrophin 3'-UTR, based on sequence and thermodynamic properties. Five additional miRNAs were found to be excellent candidates for targeting the mouse utrophin mRNA, namely, let-7c, miR-150, miR-196b, miR-296-5p, miR-133b and the previously reported miR-206. Interestingly, miR-133b and miR-206 are known to be muscle specific. These miRNAs are also predicted to target human utrophin. The positions of their predicted target sites in the utrophin 3'-UTR are shown in FIG. 16.

The Utrophin-A mRNA is Translationally Repressed

To validate the prediction that the utrophin-A mRNA is targeted by multiple miRNAs, we first used ribosomal profiling of the utrophin-A mRNA in mouse myoblast C2C12 cells to determine whether it is translationally repressed. As shown in FIG. 1D, the utrophin-A mRNA is found in lighter, monosomal fractions, indicating that it is associated with one or only a few ribosomes and is therefore being translated inefficiently. In contrast, the β-actin mRNA is found in heavier, polysomal fractions, indicating that it is associated with many ribosomes. Therefore, in C2C12 cells, the utrophin-A mRNA exists in a state of translational repression.

The 5'- and 3'-UTRs of Utrophin Mediate Translational Repression

As both the 3'- and 5'-UTRs of genes are known to mediate miRNA-based repression, we made four reporter constructs, based on the pGL3 vector (FIG. 1A), to determine the contributions of the 5'- and 3'-UTRs of the utrophin mRNA towards its translational repression. In 5'Luc, the 5'-UTR of the utrophin-A mRNA was cloned upstream of the luciferase coding region. The 3'-UTR was cloned downstream of the luciferase coding region to obtain Luc3'. In 5'Luc3', the luciferase coding region is flanked by the 5'- and 3'-UTRs of the utrophin-A mRNA.

Equimolar amounts of these constructs were transfected into C2C12 cells and luciferase activity was assayed. The addition of the 5'- or 3'-UTR reduced luciferase activity by ~92% or ~80% respectively, compared to the parent construct pGL3. The addition of both UTRs decreased luciferase activity by ~99%; an amount greater than each element alone suggesting co-operability between these elements (FIG. 1B). RT-PCR confirmed that there was no difference in mRNA levels produced by the four constructs (FIG. 1C), demonstrating that the inhibition was at the level of translation. Similar results were observed when HeLa cells were transfected with these constructs, suggesting that this mechanism is not limited to C2C12 cells.

To determine how the 5'- and 3'-UTRs contribute to the inefficient association of the utrophin-A mRNA with ribosomes, we performed ribosomal profiling on C2C12 cells transfected with the four reporter constructs described above. Compared to pGL3, the Luc3' mRNA was shifted towards lighter, less efficiently translating fractions (FIG. 1). An even greater shift was observed for 5'Luc3' (FIG. 1D); ~80% of the mRNA was present in fractions 2 and 3, which represent mostly translationally inactive, non-polysomal ribosomes. This suggests that the 3'-UTR of the utrophin mRNA causes a reduction in its ribosomal association, and that this effect is exacerbated in the presence of the 5'-UTR.

miRNAs Contribute to 3'-UTR-Mediated Repression of Utrophin Translation

Figure 17:
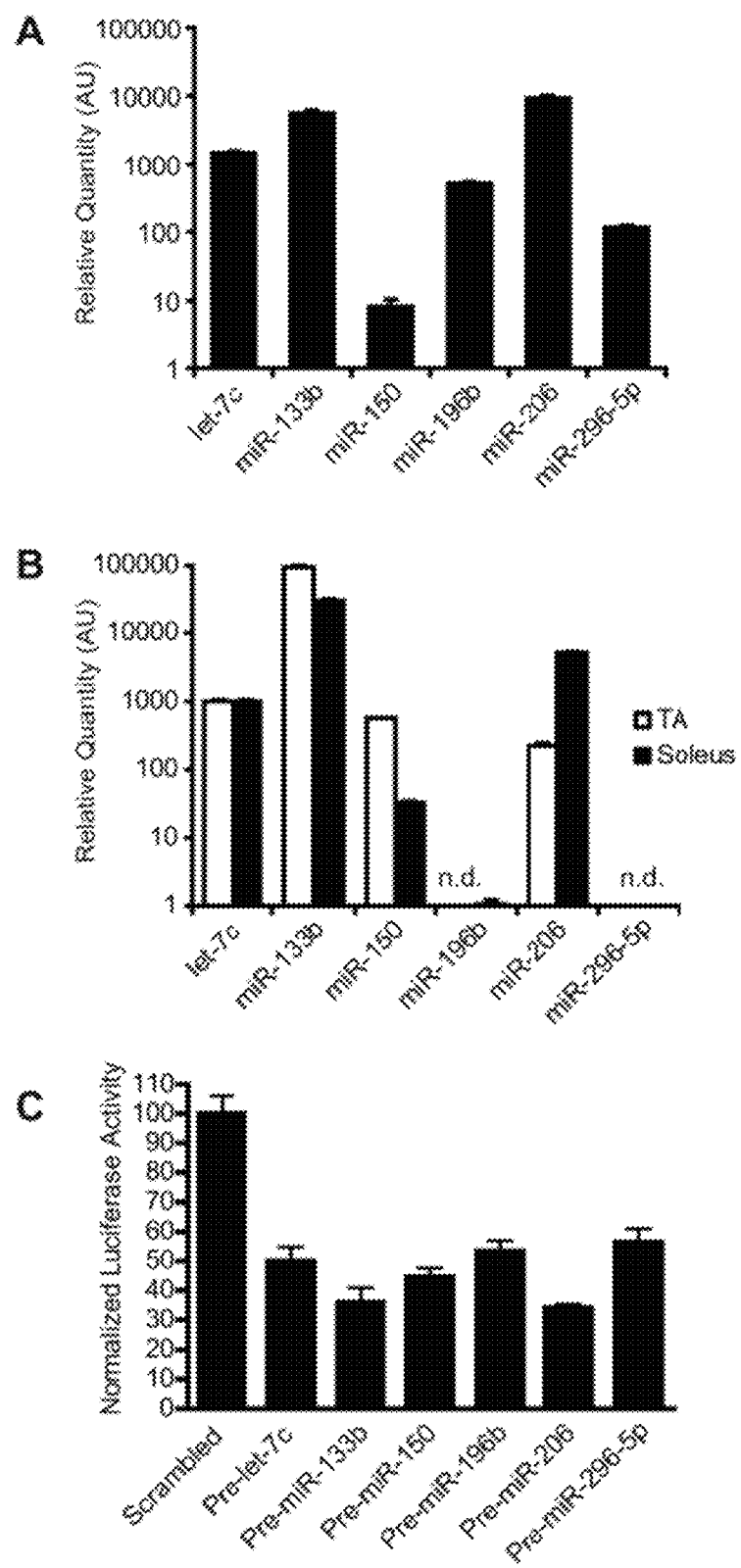
FIG. 17. Predicted miRNAs are expressed in C2C12 cells and skeletal muscle and can target the utrophin 3'-UTR. Expression levels of miRNAs in C2C12 cells (A) and TA and soleus muscles (B) were quantified using TaqMan miRNA assays. All six miRNAs are expressed in C2C12 cells. miR-150 was not detected (n.d.) in TA, while miR-296-5p was n.d. in TA or soleus. Bars represent mean±SD. (C) HeLa cells, which do not express miR-206, were transfected with 5'Luc3' and pRL-TK with different pre-miRNAs precursors or a scrambled negative control. Cells were harvested 6 hours post-transfection and a luciferase assay performed. Firefly luciferase activities were normalized to pRL-TK derived *Renilla* luciferase activity and expressed as percentage normalized luciferase activity of the negative control transfected cells. Normalized luciferase activity decreases in every pre-miRNA transfected set. Bars represent mean±SD from six independent experiments.

To validate the bioinformatic predictions and determine whether miRNAs are responsible for the translational repression mediated by the utrophin 3'-UTR, we first verified whether the six miRNAs were expressed in cultured C2C12 myoblasts and fast and slow skeletal muscles of mice. All six miRNAs were expressed in C2C12 cells and expressed at varying levels in muscle (FIGS. 17A and 17B).

Next, we co-transfected pre-miRNAs (miRNA precursor RNA stem-loops) for each of the miRNAs of interest or a scrambled pre-miRNA control, with the 5'Luc3' construct, in which the 3'- and 5'-UTRs of utrophin flank the coding sequence for firefly luciferase, into cultured HeLa cells. The Renilla luciferase expression plasmid pRL-TK was used as a control for transfection efficiency. HeLa cells were selected because they do not express endogenous miR-206, which might mask the effects (if any) of miR-206 added exogenously. A luciferase assay was performed 6 hours post-transfection. Compared to the scrambled control, all the pre-miRNAs tested produced a reduction in luciferase activity, confirming that all six miRNAs can target the utrophin 3'-UTR and repress translation (FIG. 17C).

miRNA Inhibition Relieves Utrophin 3'-UTR-Mediated Translational Repression

Figure 18:
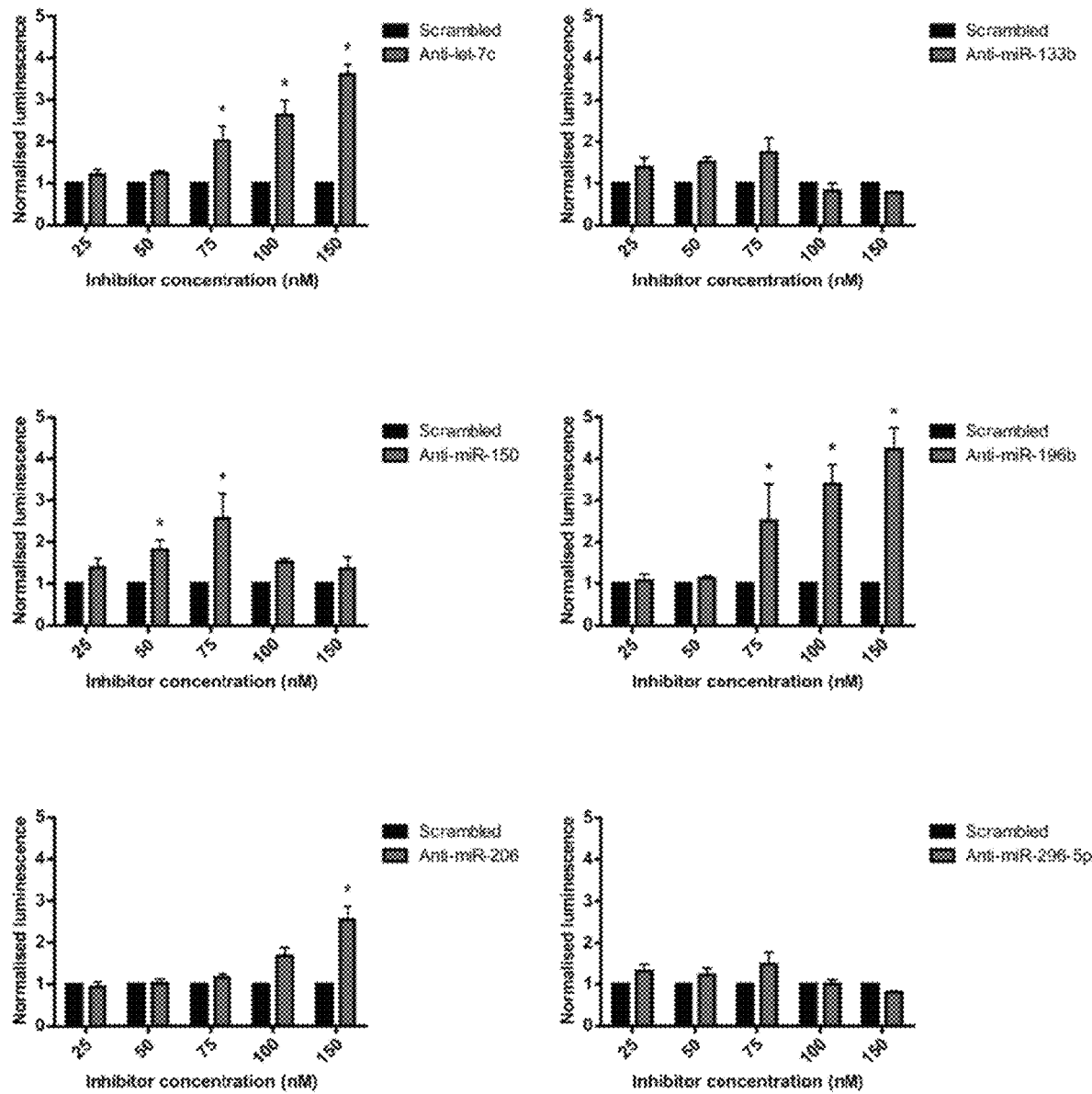
FIG. 18. miRNA inhibition can de-repress the utrophin 3'-UTR and upregulate translation. C2C12 cells were transfected with 5'Luc3', pRL-TK and different antisense miRNA inhibitors or a scrambled control inhibitor, at a range of concentrations. Luciferase assays were performed 24 hours post-transfection. Firefly/*Renilla* ratios in the presence of miRNA inhibitors were normalized to ratios in the presence of a scrambled inhibitor. Inhibitors of let-7, miR-150, miR-196b and miR-206 increased normalized luciferase activity, whereas inhibitors of miR-133b and miR-296-5p did not produce any significant upregulation. Bars represent mean±standard error from three independent experiments. *Significantly different from scrambled inhibitor by two-way ANOVA followed by Bonferroni post tests, p,0.05.
Figure 22:
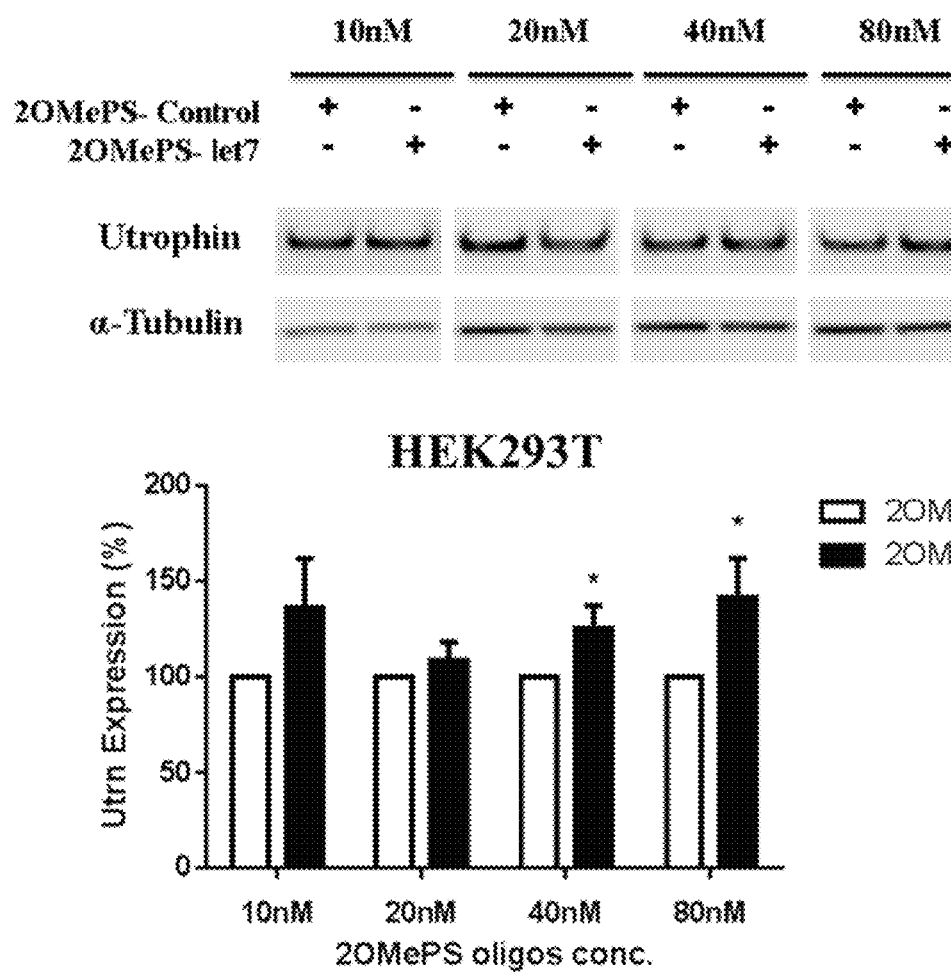
FIG. 22. Utrophin Let-7 blockers were able to upregulate endogenous utrophin protein in human HEK293T cells.
Figure 23:
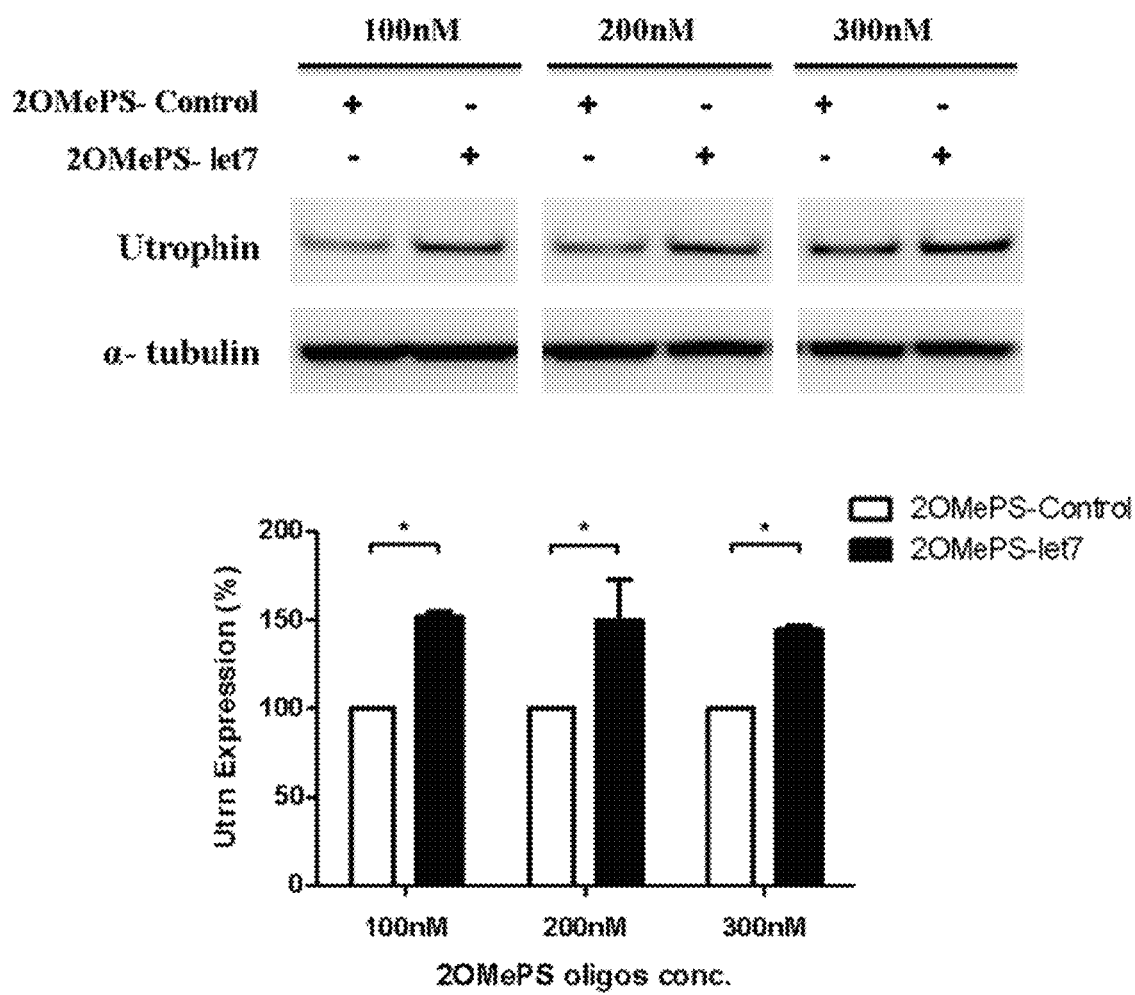
FIG. 23. Utrophin Let-7 blockers were able to upregulate endogenous utrophin protein in human HEK293T cells.
Figure 24:
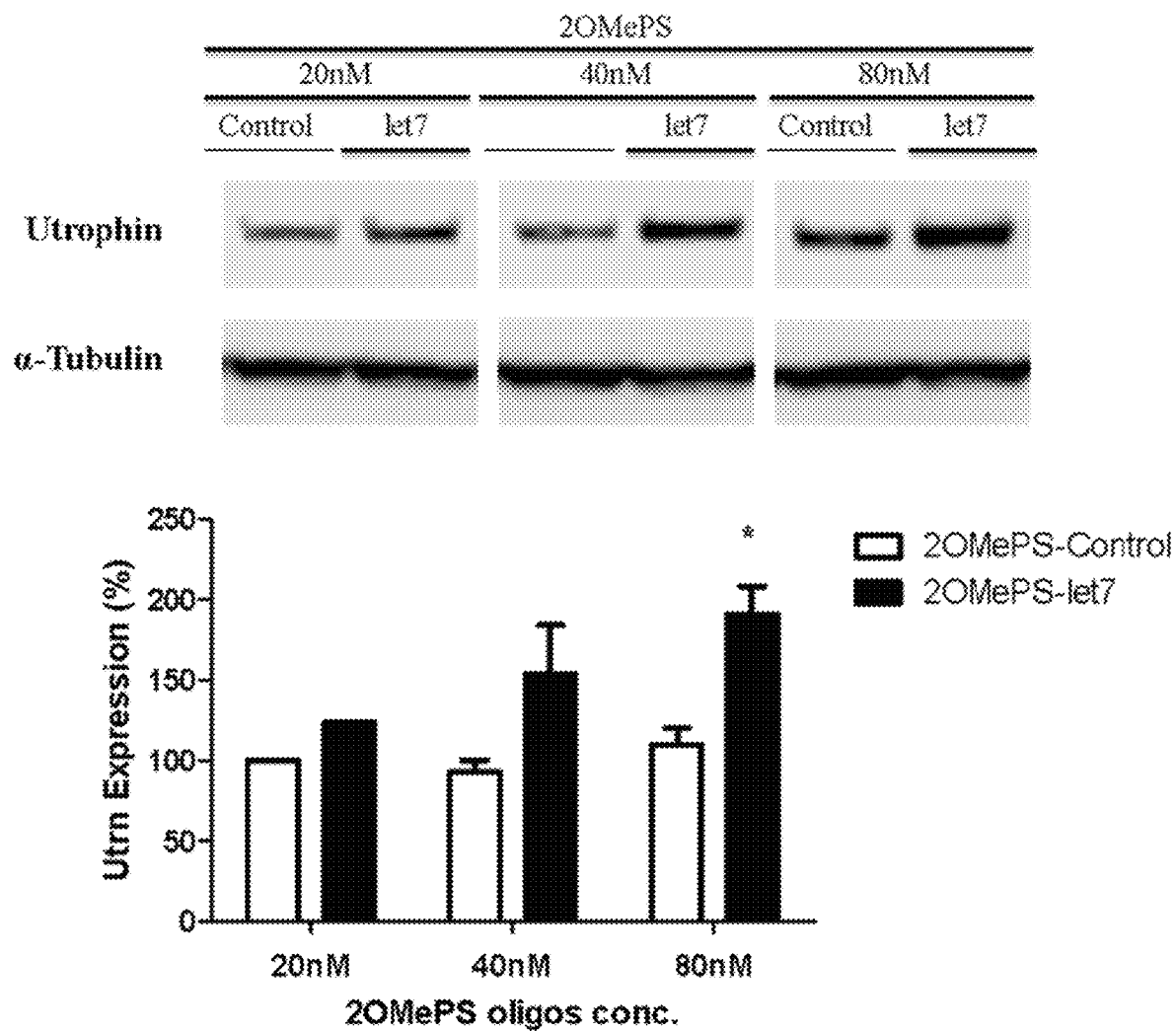
FIG. 24. Utrophin Let-7 blockers were able to upregulate endogenous utrophin protein in mouse C2C12 cells.

Having demonstrated that six miRNAs target the utrophin 3'-UTR, we asked whether inhibition of these miRNAs could de-repress the 3'-UTR and upregulate translation. Therefore, C2C12 cells were transfected with 5'Luc3' together with antisense inhibitors of the six utrophin-targeting miRNAs. Luciferase activity was assayed 24 hours post-transfection. As shown in FIG. 18, inhibitors of let-7c, miR-150, miR-196b and miR-206 were able to de-repress the utrophin 3'-UTR in a dose-dependent manner and produce increases of up to 4-fold in luciferase translation.

Next we wished to confirm that endogenous utrophin protein levels could be upregulated by inhibition of miR-NAs. To do this, we used oligomers consisting of 2-O-methyl modified bases on a phosphorothioate backbone (2OMePS). The 2OMePS were designed to bind to the utrophin 3'-UTR and block the let-7 family target site situated therein (FIG. 16), thus preventing utrophin translational repression by let-7c or other let-7 family members. This strategy should, in principle, be relatively specific for utrophin, rather than affecting other let-7 target genes. We used the 2OMePS chemistry because these oligomers are suitable for in vivo delivery and can be synthesized on a larger scale. Additionally, in our hands 2OMePS had lower cytotoxicity than the commercially available miRNA inhibitors. C2C12 cells were transfected with either a let-7-blocking 2OMePS or an inactivate control 2OMePS. DMSO (0.025%) was present in both cases due to co-testing of other substances. Cell lysates were harvested after 72 hours and levels of utrophin protein measured by Western blotting. As shown in FIG. 19, treatment with the let-7-blocking 2OMePS oligomer increased endogenous protein levels by over 2-fold, compared to the inactive control 2OMePS oligomer. This demonstrates that endogenous utrophin protein levels can be increased by blocking the actions of miRNAs, and validates the concept that miRNA inhibition could be used to upregulate utrophin, as a potential therapy for DMD.

In this study, we used a variety of bioinformatic, molecular and cell biological methods to demonstrate the role of miRNAs in the post-transcriptional control of utrophin expression. We show that at least six miRNAs target the utrophin 3'-UTR. We also demonstrate that inhibition of utrophin-targeting miRNAs can de-repress the utrophin 3'-UTR, leading to an upregulation of utrophin protein expression. These mechanisms could be targeted to upregulate utrophin in DMD.

Interestingly, we find that the 5'- and 3'-UTRs can act synergistically, such that each potentiates the inhibition caused by the other. Our ribosomal profiling experiments using reporter constructs shed light on the mechanisms of inhibition by the 5'- and 3'-UTRs, indicating that they cause an inhibition of translational initiation from the utrophin-A mRNA, thus limiting ribosome occupancy.

Having shown the importance of the 3'-UTR in repressing utrophin translation, and its interaction with the 5'-UTR, we demonstrated that this repression is mediated, at least in part, by miRNAs. We identified five new miRNAs (let-7c, miR-150, miR-196b, miR-296-5p and miR-133b) that target the utrophin 3'-UTR and confirmed the previously reported targeting by miR-206. Importantly from a therapeutic point of view, these six miRNAs can target utrophin in humans.

We tested whether antisense inhibition of these miRNAs could upregulate utrophin expression, and achieved this for four of the six miRNAs tested. It is not yet clear why inhibition of the other two miRNAs did not have the same effect. However, in addition to issues related to stability/chemistry of the inhibitors, some of the targeted miRNAs are only present at low levels in C2C12 cells, and therefore decreasing their expression would be predicted to have little effect on reporter construct expression.

Of the miRNAs studied, let-7c stood out as the best initial target as it is highly expressed in fast and slow skeletal muscles, and its antisense inhibition in C2C12 cells caused a 4-fold translational upregulation of the luciferase reporter. For this reason, we focused on let-7c for further experiments, and showed that blocking the binding of let-7 family miRNAs to the utrophin 3'-UTR, using a 2OMePS oligomer, could upregulate endogenous utrophin protein by over 2-fold, in C2C12 cells. The difference in the degree of response between the two experiments could be due to different time points examined (the utrophin gene is much larger than luciferase so more time was allowed to see a change in protein levels) or different amounts of transfection reagent used. Importantly, our results demonstrate that inhibition of miRNAs can de-repress the utrophin 3'-UTR and upregulate translation of utrophin protein, making it a viable therapeutic strategy for DMD.

For experiments investigating endogenous utrophin protein, we used 2OMePS oligomers designed to bind the utrophin 3'-UTR and block the actions of let-7 family miRNAs, in place of commercially produced antisense miRNA inhibitors. The success of these experiments is greatly encouraging, given that 2OMePS oligomers can be synthesized on a relatively large scale are suitable for use in vivo.

In conclusion, we have shown that the utrophin-A mRNA is subject to a significant degree of translational repression, mediated by its 5'- and 3'-UTRs, and that the actions of miRNAs contribute significantly to this repression. We identify five novel miRNAs that target the utrophin 3'-UTR and demonstrate that inhibition of miRNA targeting can de-repress the utrophin 3'-UTR, leading to an upregulation in utrophin protein translation. Therefore, utrophin upregulation by miRNA inhibition represents a novel therapeutic strategy for DMD.

Example 6: DMD Antisense Therapeutic Approach for Upregulation of Utrophin

In this example, a utrophin-upregulation based therapeutic approach for Duchenne's Muscular Dystrophy (DMD) is developed using oligonucleotides designed to block the let-7c miRNA binding site (let-7c site blocking 2'-O-methyl phosphorothioate oligonucleotides or "let-7 blockers") in the 3'-UTR of the Utrophin gene.

First, efficacy of let-7 blockers was validated in C2C12 (mouse) as well as human (HEK293T) cell lines in vitro. The let-7 SBO's were able to upregulate utrophin reporter constructs, as well as endogenous utrophin protein (FIG. 21-24).

Figure 25:
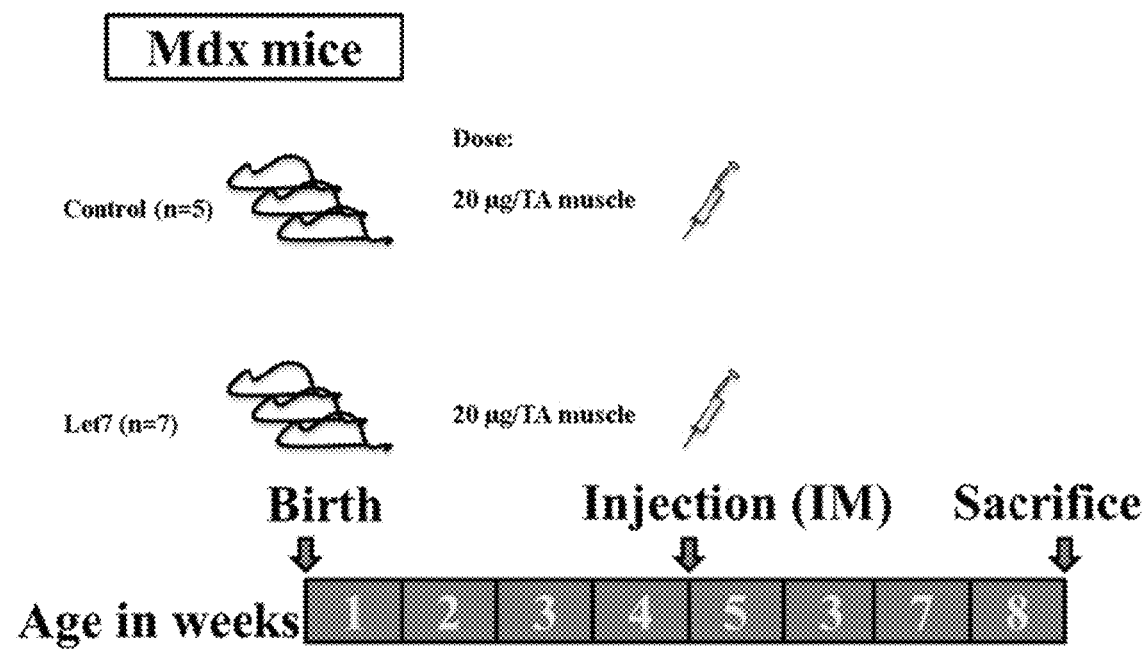
FIG. 25. Experimental scheme for pharmacodynamic studies of utrophin let-7 SBO injected intramuscularly in the mdx mouse model for DMD in vivo.
Figure 26:
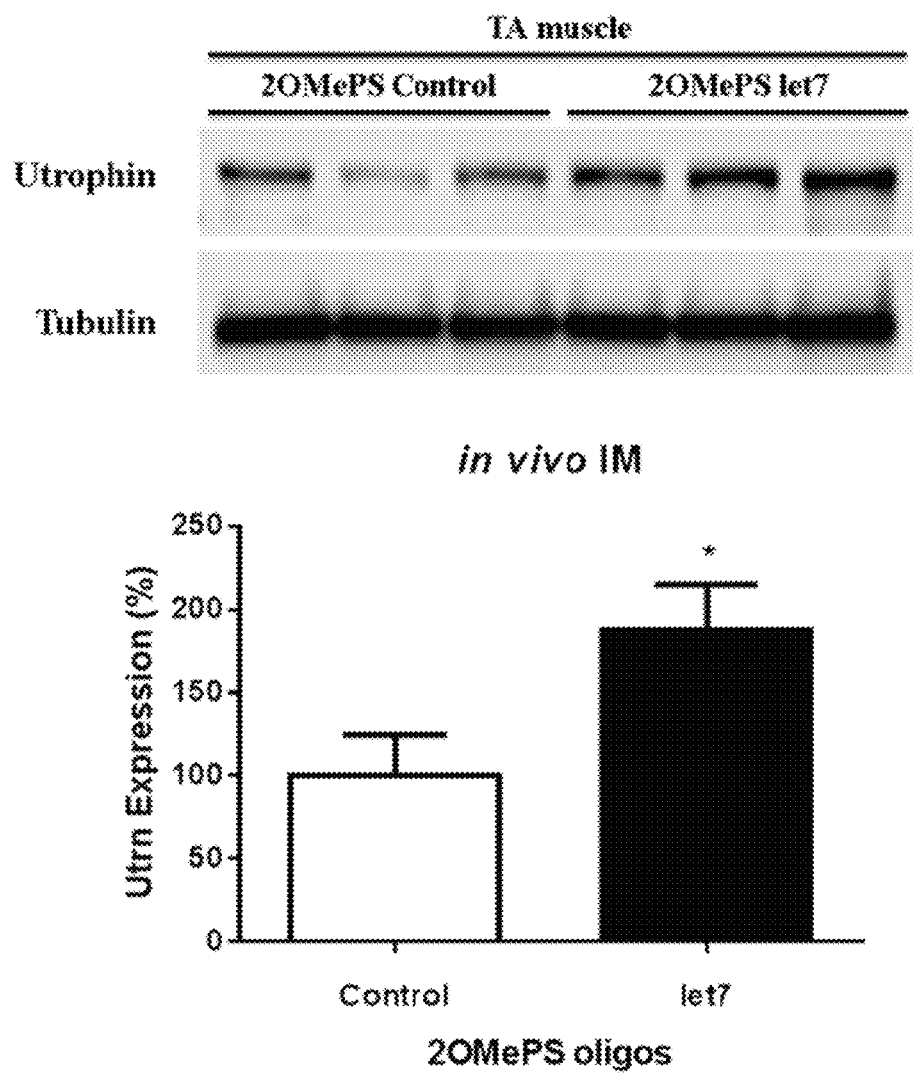
FIG. 26. Utrophin protein expression was upregulated significantly, as measured by Western blot, in Tibialis anterior (TA) muscles of mdx mouse model for DMD in vivo.

Second, pharmacodynic studies were successfully conducted in the mdx model for DMD in vivo (FIG. 25). Utrophin protein expression was upregulated significantly, as measured by Western blot, in Tibialis anterior (TA) muscles of 1 month old mdx mice that had been injected for 1 month with 20 micrograms of let7 SBO (FIG. 26).

Figure 27:
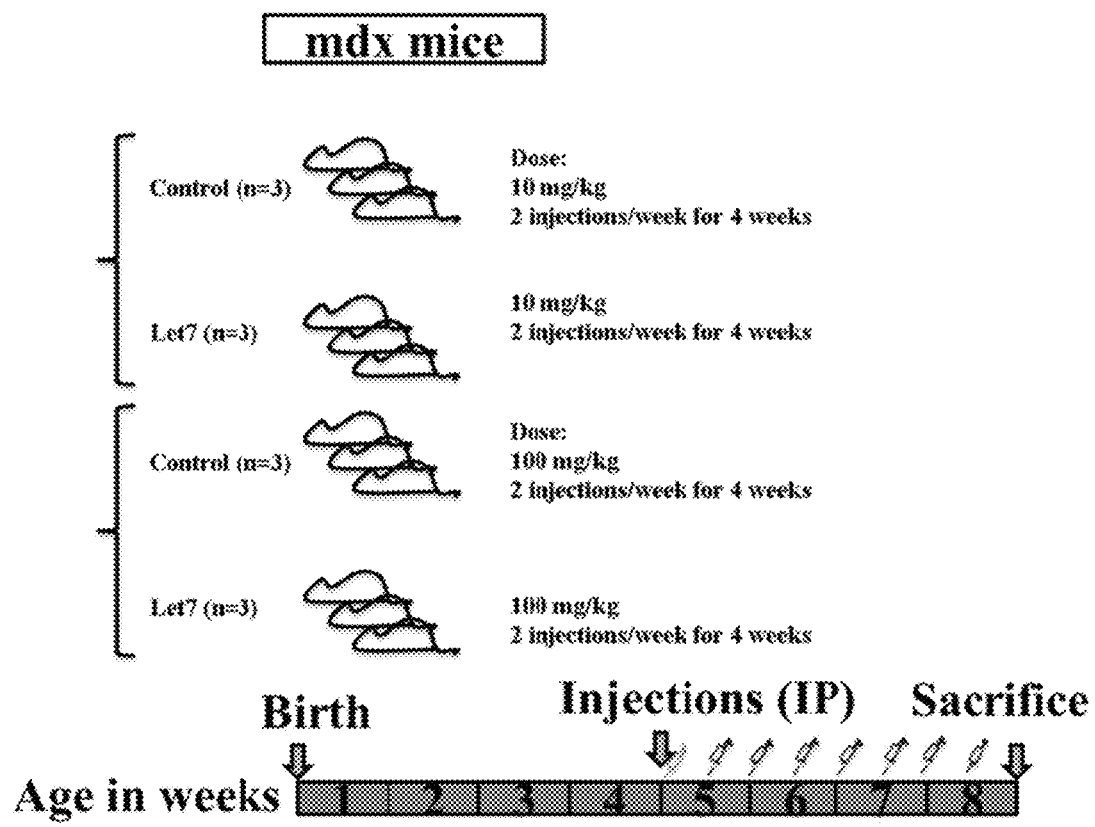
FIG. 27. Experimental scheme for studies of utrophin let-7 SBO administered systemically in the mdx mouse model for DMD in vivo.
Figure 28:
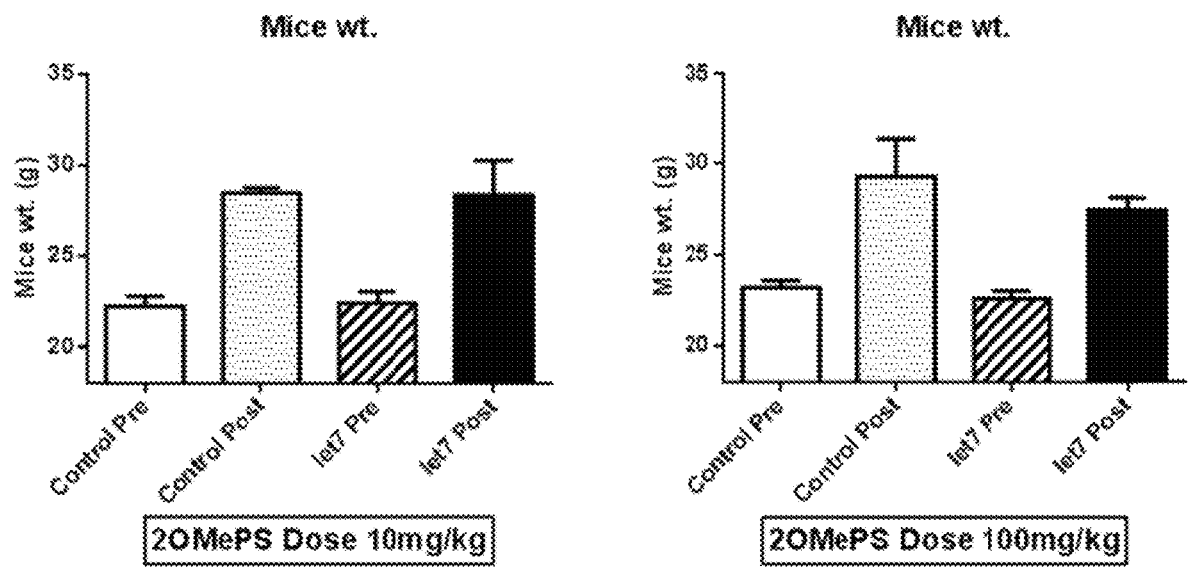
FIG. 28. Utrophin Let-7 SBO administration did not change body weight.

Third, using systemic delivery of let-7 blockers for 2 months in mdx mice to block of endogenous let-7c binding to the utrophin gene (FIG. 27) resulted in significant morphological, biochemical and physiological improvement of the dystrophic phenotype in vivo, without adverse effects such as a significant change in body weight relative to the control mice (FIG. 28)

Figure 29:
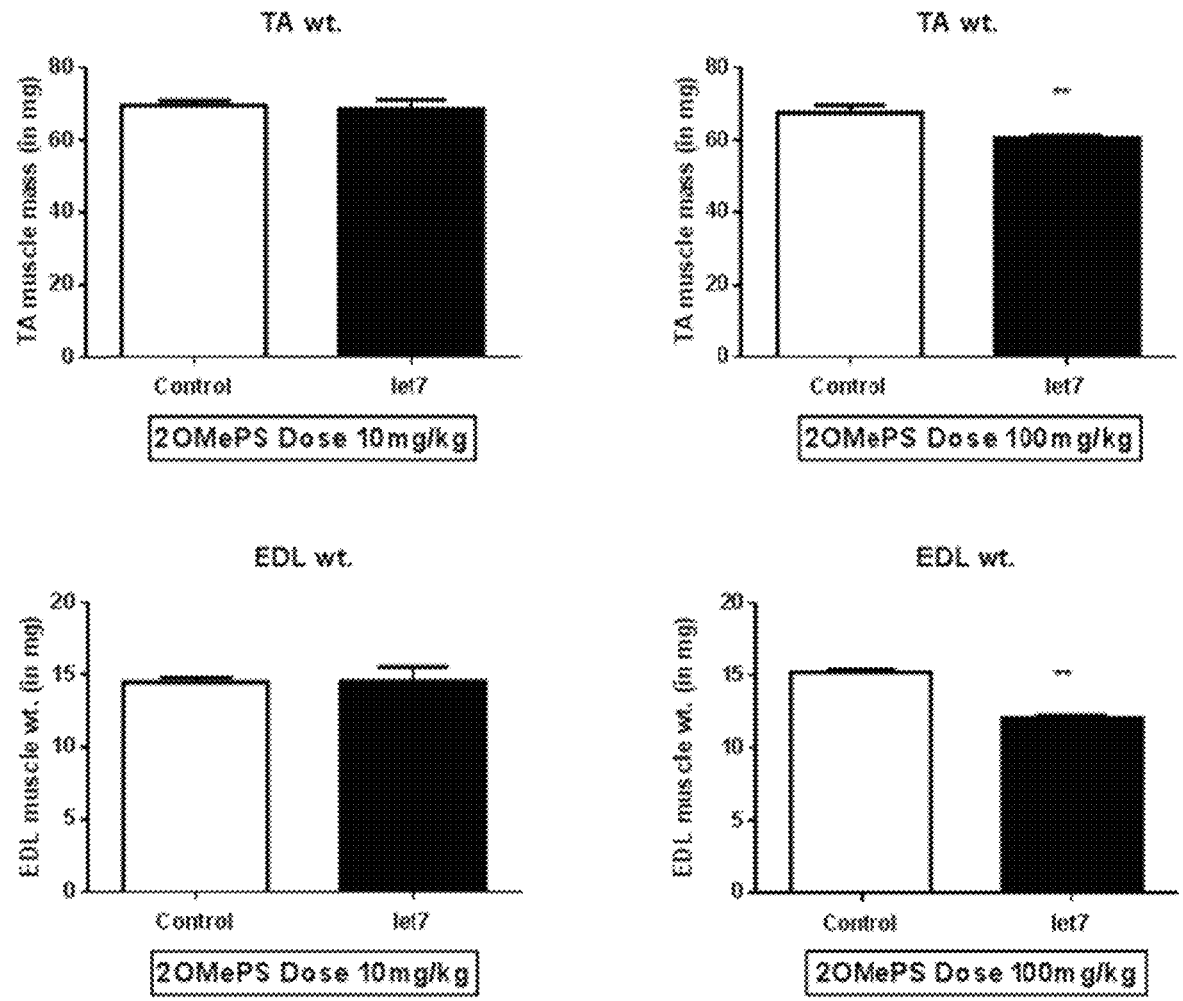
FIG. 29. Utrophin Let-7 SBO administration reduced extensor digitorum longus (EDL) muscle weight.
Figure 31:
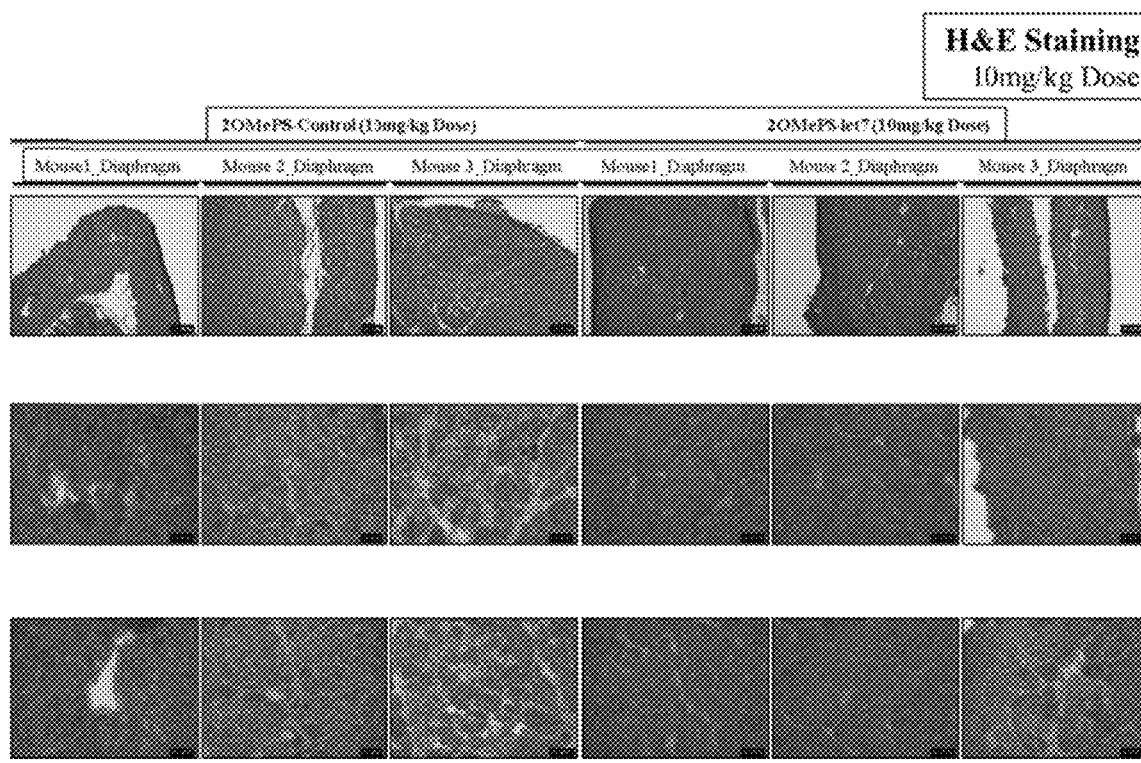
FIG. 31. Histopathological changes were decreased by let-7 treatment. H&E staining—10 mg/kg dose. Cryostat sections of Diaphragm muscle of Mdx mouse stained with hematoxylin and eosin after 1 month of treatment with 10 mg/kg 2OMePS-Control and 2OMePS-let7 oligos. (Note: images were stitched together side by side to give a single large 2D image frame at 10× magnification).
Figure 32:
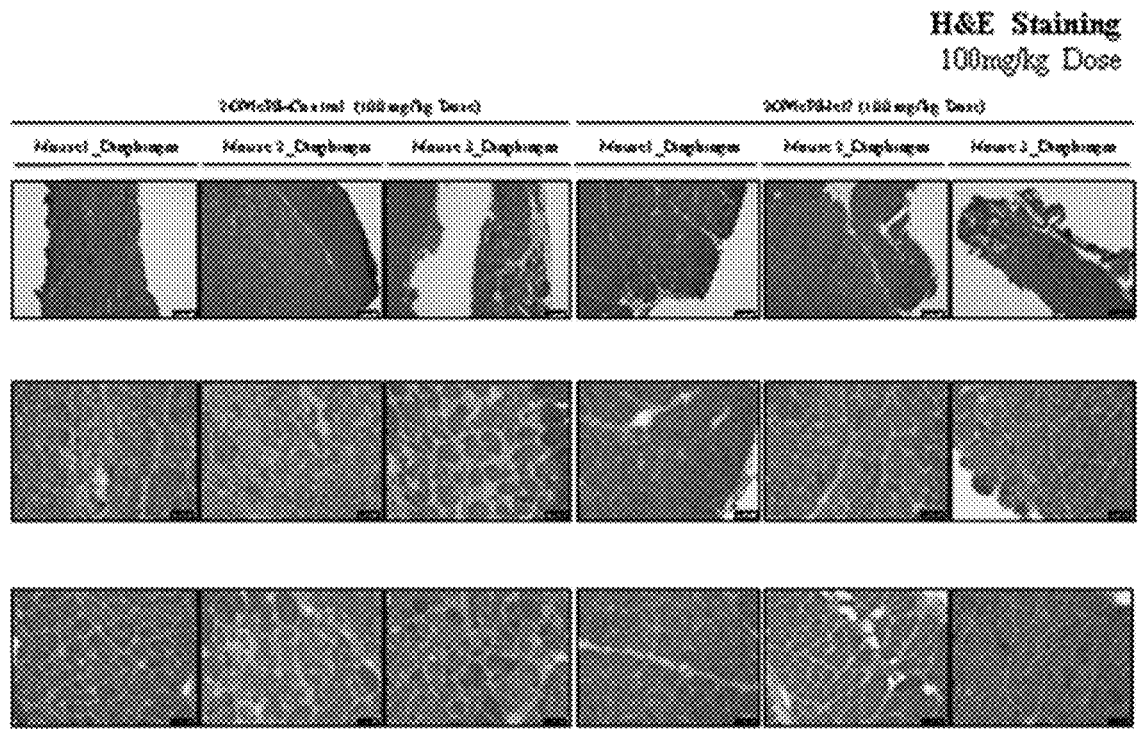
FIG. 32. Histopathological changes were decreased by let-7 treatment. H&E staining—100 mg/kg dose. Cryostat sections of Diaphragm muscle of Mdx mouse stained with hematoxylin and eosin after 1 month of treatment with 100 mg/kg 2OMePS-Control and 2OMePS-let7 oligos. (Note: images were stitched together side by side to give a single large 2D image frame at 10× magnification).
Figure 33:
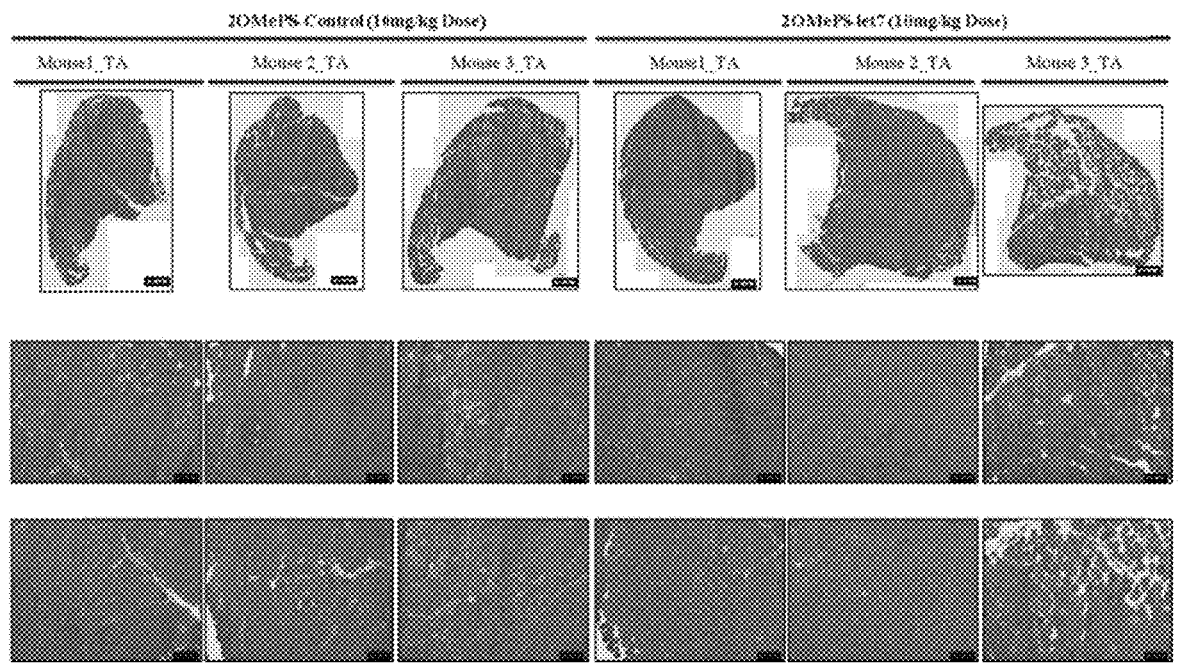
FIG. 33. Histopathological changes were decreased by let-7 treatment. H&E staining—10 mg/kg dose. Cryostat sections of TA muscle of Mdx mouse stained with hematoxylin and eosin after 1 month of treatment with 10 mg/kg 2OMePS-Control and 2OMePS-let7 oligos. (Note: images were stitched together side by side to give a single large 2D image frame at 10× magnification).
Figure 34:
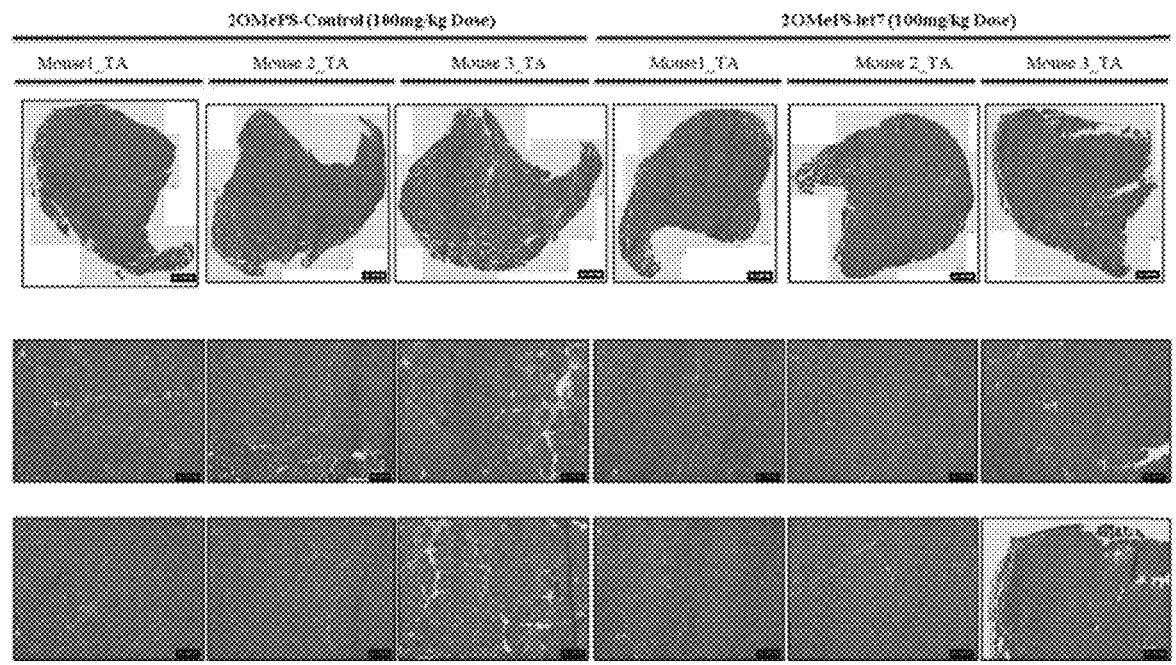
FIG. 34. Histopathological changes were decreased by let-7 treatment. H&E staining—100 mg/kg dose. Cryostat sections of TA muscle of Mdx mouse stained with hematoxylin and eosin after 1 month of treatment with 100 mg/kg 2OMePS-Control and 2OMePS-let7 oligos. (Note: images were stitched together side by side to give a single large 2D image frame at 10× magnification).
Figure 37:
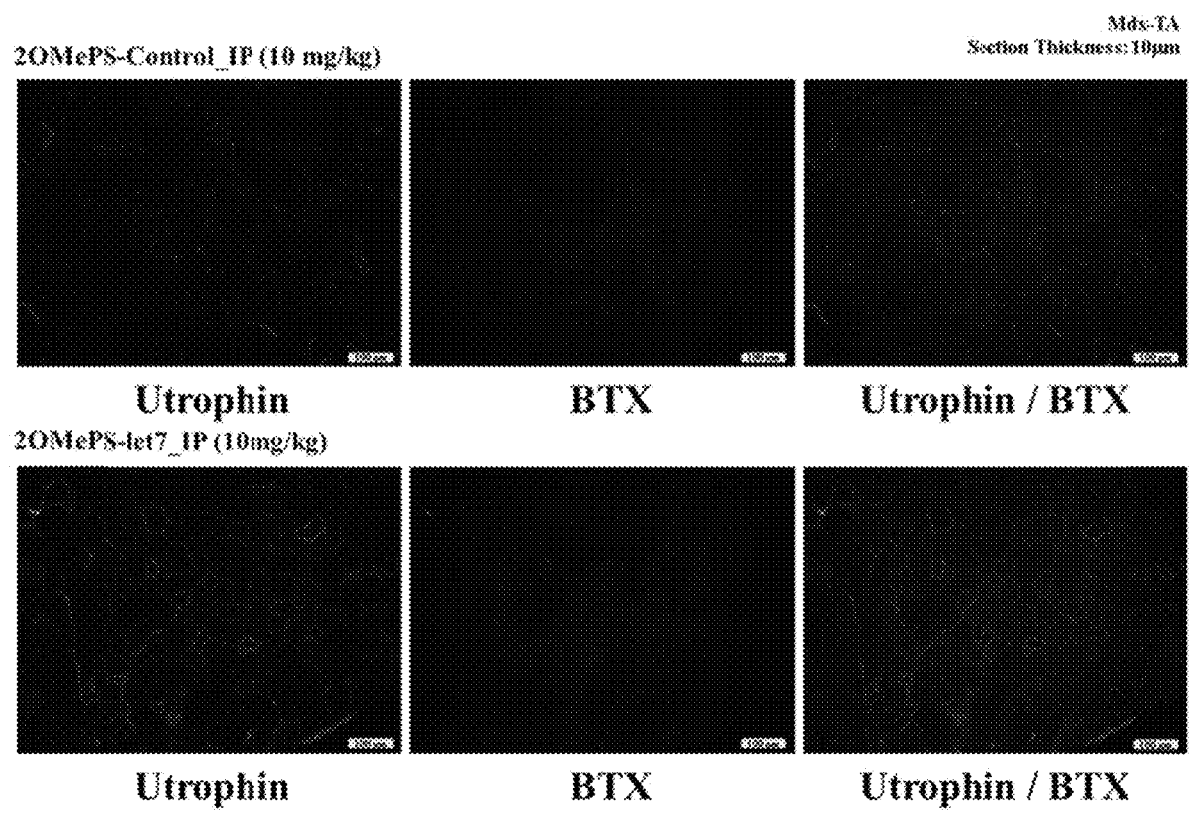
FIG. 37. Increased utrophin expression was seen in NMJ-poor areas after let-7 treatment.
Figure 38:
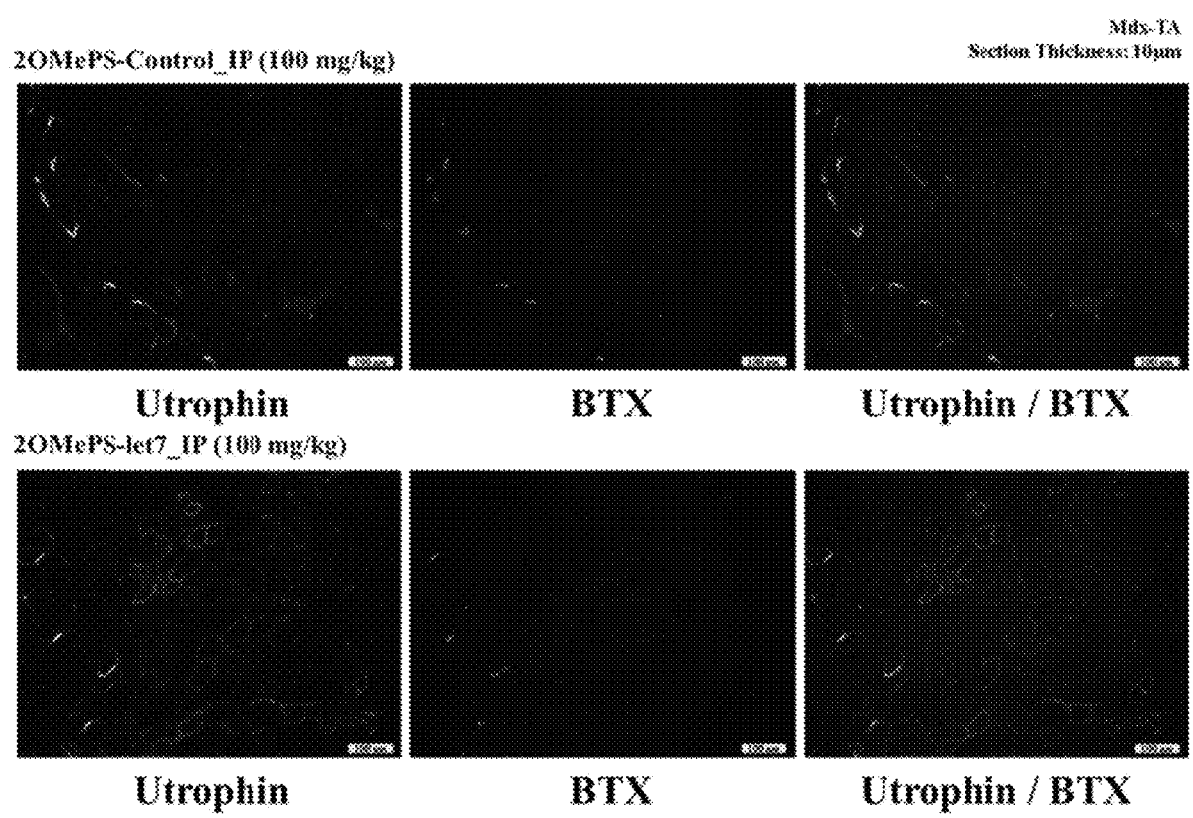
FIG. 38. Increased utrophin expression was seen in NMJ-rich areas after let-7 treatment.
Figure 39:
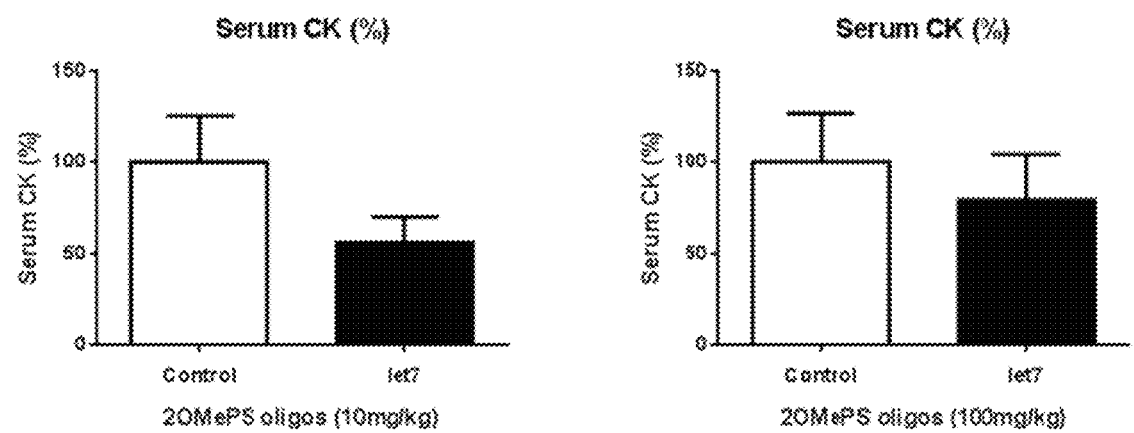
FIG. 39. Let-7 SBO treatment and serum CK reduction.
Figure 40:
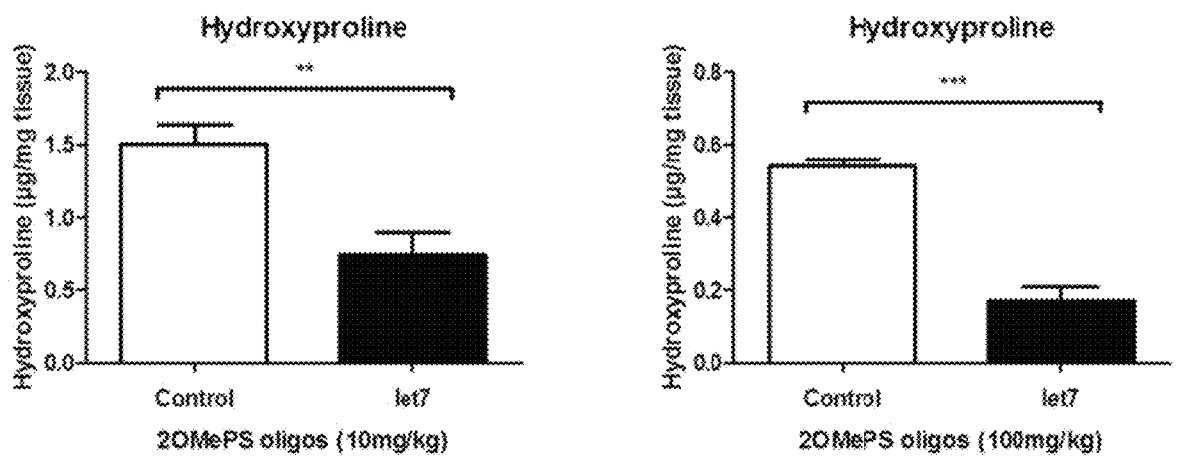
FIG. 40. Hydroxyproline content of fibularis muscles. Let-7 SBO treatment reduced fibrosis as evidenced by Hydroxyproline content.
Figure 41:
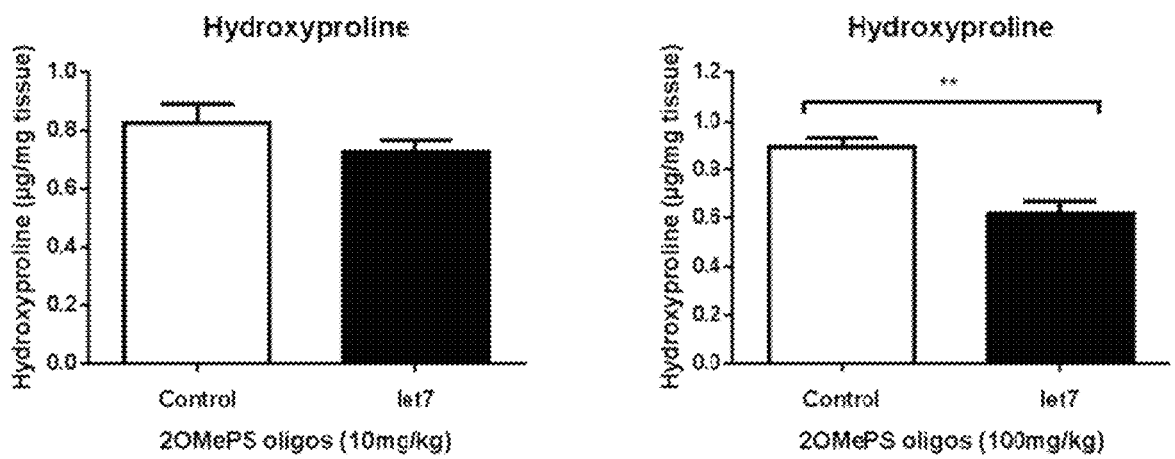
FIG. 41. Hydroxyproline content of Diaphragm. Utrophin let-7 SBO treatment reduced fibrosis as evidenced by Hydroxyproline content.
Figure 42:
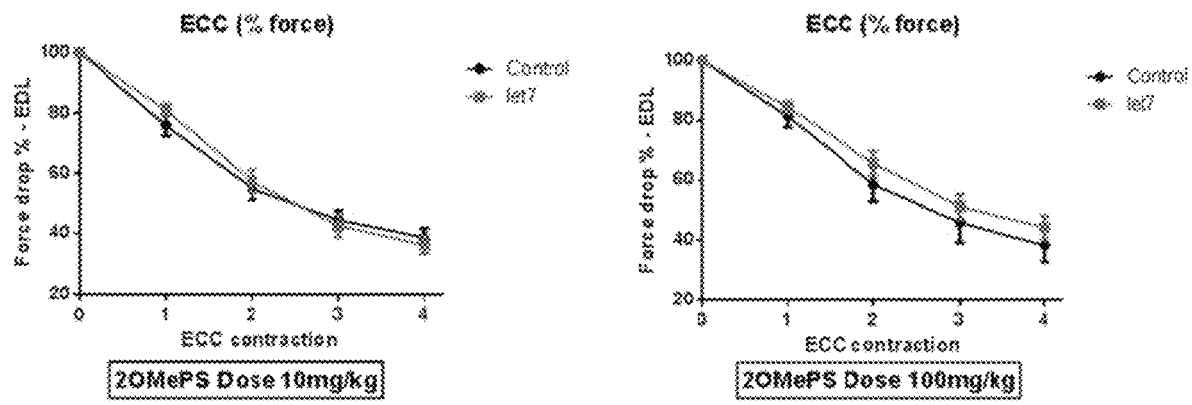
FIG. 42. Utrophin let-7 SBO treatment did not change post-eccentric contraction force drop.
Figure 43:
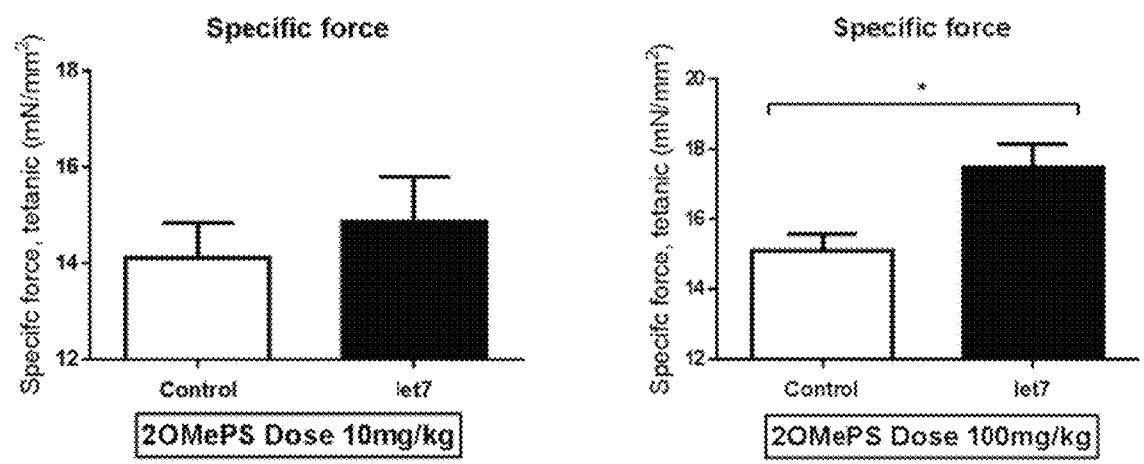
FIG. 43. Specific force of EDL muscles. Utrophin let-7 SBO treatment increased specific force.

Specifically, utrophin let-7 SBO treatment reduced extensor digitorum longus (EDL) muscle weight (FIG. 29). Utrophin let-7 SBO treatment decreased centrally nucleated fibers (CNFs) in TA muscle (FIG. 30). Histopathological changes were decreased by let-7c treatment in diaphragm and TA muscles (FIGS. 31-34). Let-7 SBO treatment also reduced muscle fiber size variability (FIG. 35). Let-7 SBO treatment was observed to increase utrophin protein expression in the diaphragm (FIG. 36). Increased utrophin expression was seen in both NMJ-poor (FIG. 37) and NMJ-rich (FIG. 38) areas. Serum CK reduction upon let-7 SBO treatment was measure (FIG. 39). As evidenced by hydroxyproline content, let-7 SBO treatment decreased muscle fibrosis (FIG. 40-41). While let-7 SBO treatment did not change post-eccentric contraction force drop in EDL muscles (FIG. 42), treat did decrease specific force in EDL muscles (FIG. 43).

In sum, the results establish that the let7 blockers as a therapeutic approach for DMD.

Example 7: Functional Improvement of Dystrophic Muscle by Repression of Utrophin:Let-7c Interaction Duchenne muscular dystrophy (DMD) is a fatal genetic disease caused by an absence of the 427 kD muscle-specific dystrophin isoform. Utrophin is the autosomal homolog of dystrophin and when overexpressed, can compensate for the absence of dystrophin and rescue the dystrophic phenotype of the mdx mouse model of DMD. Utrophin is subject to miRNA mediated repression by several miRNAs including let-7c. Inhibition of utrophin:let-7c interaction is predicted to 'repress the repression' and increase utrophin expression. We developed and tested the ability of an oligonucleotide, composed of 2'-O-methyl modified bases on a phosphorothioate backbone, to anneal to the utrophin 3'UTR and prevent let-7c miRNA binding, thereby upregulating utrophin expression and improving the dystrophic phenotype in vivo. Suppression of utrophin:let-7c interaction using bi-weekly intraperitoneal injections of let7 site blocking oligonucleotides (SBOs) for 1 month in the mdx mouse model for DMD, led to increased utrophin expression along with improved muscle histology, decreased fibrosis and increased specific force. The functional improvement of dystrophic muscle achieved using let7-SBOs demonstrates a novel utrophin upregulation-based therapeutic strategy for DMD.

Figure 44:
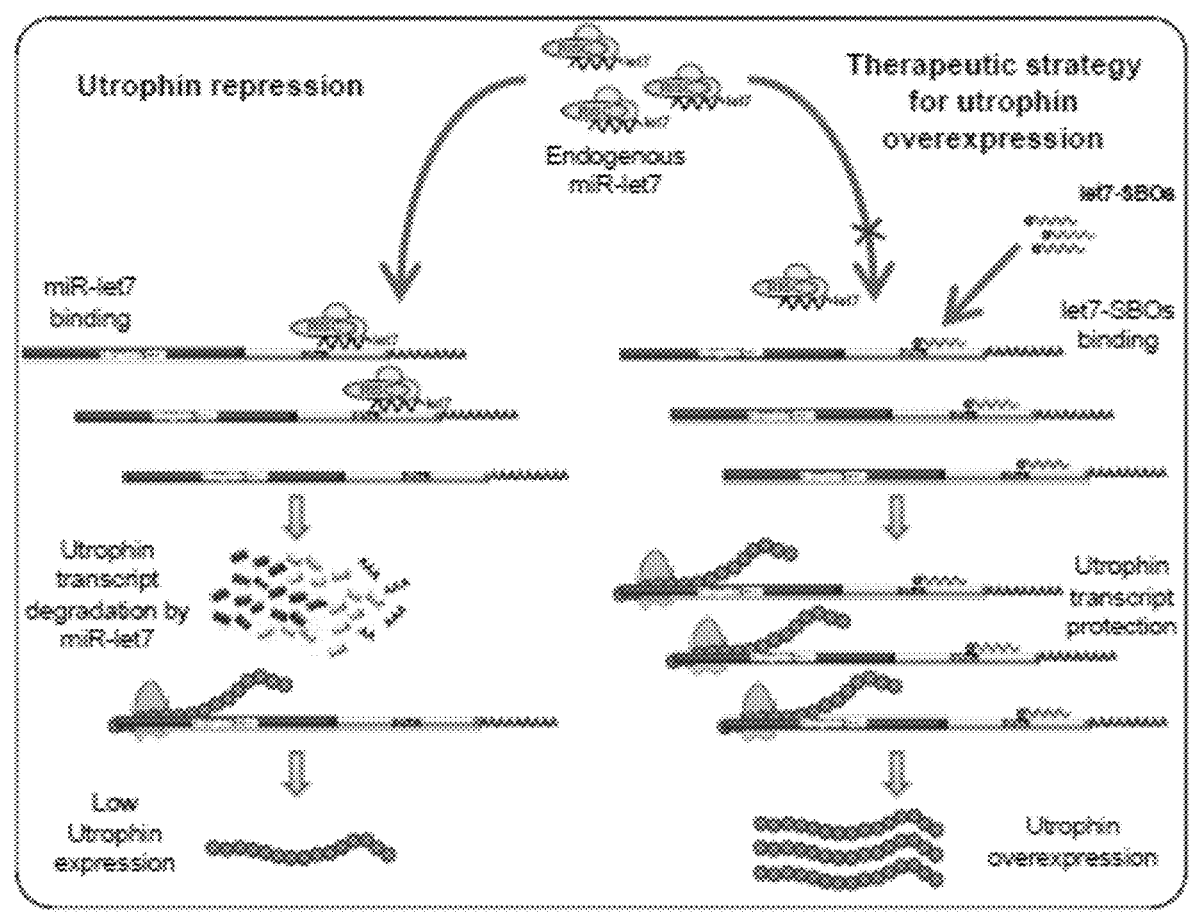
FIG. 44. Therapeutic strategy for utrophin upregulation. Schematic representation for let-7 miRNA mediated repression of utrophin in muscle and therapeutic strategy for utrophin upregulation by let7-SBOs. In left panel, the 3'UTR of utrophin-A contains a let-7 binding site that is targeted by the let-7 miRNA, associated with a RNA-induced silencing complex (RISC) leading to translational repression and decreased levels of utrophin protein. Right Panel shows let7-SBOs block the endogenous let-7 binding site of 3'UTR, preventing miRNAs from binding. In this case, the normally occurring miRNA-mediated repression of utrophin will be repressed, leading to an increase in utrophin expression.

Since let7-SBOs anneal to the utrophin 3'UTR, our blocking strategy is comparatively specific for utrophin (FIG. 44), rather than affecting other let-7 target genes as would be the case in using a let-7 miRNA sponge/antagomir strategy.

Materials and Methods

Cell Culture

The mouse muscle C2C12 myoblasts and human kidney HEK293T cell lines (both from ATCC) were cultured in DMEM with 10% FBS, glutamine, penicillin and streptomycin.

Oligonucleotides

The let7-SBOs (5'-CUG AGG UAG AAA GGU GAU CAU GGC UC-3'; SEQ ID NO: 24) and control oligonucleotides (5'-GUG AGC ACU UCU UUC CUU CUU UUU U-3'; SEQ ID NO.: 72), are 2'-O-methyl phosphorothioate RNA oligos with a phosphorothioate backbone. The let7-SBOs was designed to specifically target the let7 miRNA binding site in the utrophin 3'UTR. These oligonucleotides were synthesized on an Expedite 8909 Nucleic acid synthesizer using the 1 μmol thioate synthesis protocol supplied by the manufacturer.

Constructs

For luciferase assays in stable cell lines, we used the previously described C2C12-5'3' cell line containing the 5'- and 3'-UTRs of utrophin flanking the luciferase coding sequence and stably expressed in mouse C2C12 cells.

For luciferase assays in human HEK293T cells, we generated the pGL4:50-5'Luc3'Hu construct by amplifying the 5'-(forward 5'-gtccaagcctGTATTGATGTCAAGCT-GAACCA-3' (SEQ ID NO.: 73) and reverse 5'-act-taagcctCTTGCCAGAGTTTCAAGATAATC-3' (SEQ ID NO.: 74) primers) and 3'-UTRs (forward 5'-caggggccggccAGTATTCATCCGGCCAACC-3' (SEQ ID NO.: 75) and reverse 5'-caaaggccggccGTGTTAAAAT-TACTTTTATTCAGGATG-3' (SEQ ID NO.: 76) primers) of human utrophin and cloning them into the Hind III and Fse I sites that flank the luciferase coding sequence in the pGL4:50 vector (Promega, Madison, Wis.).

For transient transfections in mouse C2C12 cells, we used the previously described pGL3-5'Luc3' construct containing the mouse 5'- and 3'-UTRs of utrophin flanking the luciferase site [26]. The Q5 Site-Directed Mutagenesis Kit (New England Biolabs) was used for deleting the let-7 site (24 bp sequence 5'-AGCCATGATCACCTTTCTACCTCA-3' (SEQ ID NO: 18); deletion of bases from 3'UTR of utrophin (Accession number: NM_007124.2) from pGL3-5'Luc3' to create the pGL3-5'Luc3'-Δlet7 construct.

Transfection

All oligonucleotide transfections were done using Lipofectamine RNAiMAX Transfection Reagent (Invitrogen) according to the manufacturer's instructions. For oligonucleotide transfections, a 3:1 ratio of Lipofectamine RNAiMAX (μl):μg oligonucleotides was used. For the transfection of plasmid constructs we used the LF3000 Transfection Reagent (Invitrogen) according to the manufacturer's instructions.

Luciferase Reporter Assays

Cells (C2C12 or HEK293T) were plated in 24 well plates at 30,000 cells per well, 1 day before transfection. 500 ng pGL3-5'Luc3', pGL3-5'Luc3'-Δlet7 or equimolar amounts of other constructs were transfected, with 50 ng pRL-TK (Promega) and 100 nM let7-SBOs or control oligonucleotides, per well. Reporter activity was measured using the Dual Luciferase Assay (Promega) 24 hrs after transfection instructions using a TD 20/20 luminometer (Turner Designs, Sunnyvale, Calif.).

Treatment of Mdx Mice with Oligonucleotides and Sample Collection

Male mdx (C57BL/10ScSn-Dmd$^{mdx}$/J) mice were obtained from The Jackson Laboratory (Bar Harbor, Me., USA). Mice were housed at the animal facility at the University of Pennsylvania before initiation of experiments. All experiments were approved by the Institutional Animal Care and Use Committee at the University of Pennsylvania.

For an in vivo proof-of-principle, a single dose of 20 μg let7-SBOs and unrelated control oligonucleotides was injected in tibialis anterior (TA) muscles of 1 month old male mdx mice (n=3 for each group).

For systemic in vivo study the block randomization method was used to randomize mice into groups that result in equal sample sizes. Starting at an age of 1 month, mdx mice were treated intraperitoneally with low (10 mg; n=3) and high (100 mg; n=3) of let7-SBOs per kg body weight in 250 μl saline twice weekly for 1 month. For control 3 mdx mice in each group were injected intraperitoneally with low (10 mg) and high (100 mg) of control oligonucleotides per kg body weight in 250 μl saline twice weekly for 1 month.

Mice were sacrificed by carbon dioxide ($CO_2$) euthanasia followed by cervical dislocation after the final injection. Blood samples were taken by cardiac puncture under deep terminal anesthesia for serum analysis. Serum was collected by centrifuging at 2,000 g for 5 min and it was stored at −80° C. until analysis. After sacrifice, muscles and tissues were isolated, embedded in OCT and frozen in liquid nitrogen-cooled Isopentane, and stored at −80° C. Investigators were not blinded for the study. For all experiments sample sizes (n) are indicated in each figure legend.

Ex Vivo Physiological Assessment of Skeletal Muscle

Physiological properties, including isometric twitch force, isometric tetanic force, and force drop after ECCs, were quantified on freshly isolated EDL muscles from 2 months old mdx mice using an Aurora Mouse 1200A System equipped with Dynamic Muscle Control v.5.3 software, as described previously. EDL muscles were maintained in constantly oxygenated Ringer's solution (100 mM NaCl, 4.7 mM KCl, 3.4 mM $CaCl_2$, 1.2 mM $KH_2PO_4$, 1.2 mM $MgSO_4$, 25 mM HEPES and 5.5 mM D-glucose) at 24° C. Maximal isometric twitch and tetanic contractions were obtained using a stimulation frequency of 2500 Hz for 0.2 ms and 120 Hz for 500 ms respectively. Five min were allowed between two tetanic contractions to ensure muscle recovery. Muscle length was adjusted to obtain the maximal twitch response and this length was measured and recorded as optimal length ($L_O$). Muscle cross-sectional area (CSA) of EDL muscles was calculated by dividing the muscle mass by the product of the muscle density coefficient (1.06 g/cm$^3$), muscle $L_O$, and the fiber length coefficient (0.45 for EDL). Specific force was determined by normalizing maximum isometric tetanic force to CSA.

After testing the isometric properties of EDL, a series of five ECCs was applied. The force drop was calculated as the percent difference in tetanic force between the first and fifth ECC. At the end of the physiological assessment, EDL muscles were embedded in OCT and frozen in liquid nitrogen-cooled Isopentane, and stored at −80° C.

Western Blotting

Western blotting was performed as described. Cells and mouse muscles were processed in TNEC lysis buffer (1.5 mM Tris-HCl pH 8, 2.15 mM NaCl, 3.1% IGEPAL CA-630, 4.2 mM EDTA with Complete Protease Inhibitors-Roche). Protein concentration was assayed using a BCA Protein Assay Kit (Pierce). Approximately 30-40 μg protein were denatured with LDS sample buffer and NuPAGE reducing reagent (both Invitrogen) and heated to 72° C. in for 10 min, then separated on 3-8% Tris-Acetate gels (Invitrogen) with Tris-Acetate running buffer for 1.5 hrs at 100 V. Proteins were transferred to nitrocellulose membranes for 15 min at 25 V in ice-cold transfer buffer (25 mM Tris-Cl pH 8.3, 192 mM glycine, 20% methanol, 0.05% sodium dodecyl sulfate) using Trans-Blot Turbo transfer system (BioRad). Efficiency of transfer and the even loading of lanes was verified by using post-transfer Ponceau-S staining of the membrane. After digital scanning Ponceau-S staining was removed by TBST washing. Membranes were blocked for 1 hr at room temperature in 5% non-fat milk in TBST (50 mM Tris-Cl pH 7.5, 150 mM NaCl, 0.1% Tween 20), then probed for utrophin (upper half of membrane) with mouse monoclonal anti-utrophin antibody MANCHO3 clone 8A4 (developed by Glenn E. Morris and obtained from the Developmental Studies Hybridoma Bank, Iowa) diluted 1:50 in 0.5% non-fat milk in TBST, or α-tubulin (lower half of membrane) with anti-α-tubulin antibody clone DM1A (Sigma) or vinculin with anti-vinculin (7F9) mouse antibody (Santa Cruz Biotechnology) diluted 1:2500 in 0.5% non-fat milk in TBST, for 1 hr at room temperature. For probing c-Myc, Stat3 and Jak3 proteins anti-c-Myc Rabbit (D3N8F) mAb (1:1000 dilution), anti-Stat3 (D3Z2G) Rabbit mAb (1:1000 dilution) and anti-Jak3 Rabbit mAb (1:1000 dilution) were used in 0.5% non-fat milk in TBST, for 1 hr at room temperature. These antibodies were obtained from Cell Signaling Technology, Inc. Membranes were washed in 3 changes of TBST for 5 min each, then incubated with HRP-conjugated goat-anti-mouse IgG (Santa Cruz Biotechnology) or HRP-conjugated goat-anti-rabbit IgG (Santa Cruz Biotechnology), diluted 1:2500 in 0.5% non-fat milk in TBST (for utrophin or α-tubulin), for 1 hr at room temperature. TBST washes were repeated 3 times, then bands were visualized using SuperSignal West Pico Chemiluminescent Substrate (Thermo Fisher Scientific) and images obtained using G:Box chemiluminescence system (Syngene). For presentation clarity, images were then inverted to give dark bands on a light background. Band densities were quantified using AlphaEaseFC (Alpha Innotech Corp.).

RNA Isolation, Reverse-Transcription and Quantitative Real-Time PCR Analysis

Trizol reagent (Life Technologies) was used for total RNA isolation from mouse tissues (e.g., diaphragm, gastrocnemius and TA). 1 lag total RNA was converted to cDNA using random primers and SuperScript III First-Strand Synthesis System (Invitrogen). Quantitative PCR (qPCR) was performed on Quantstudio3 Real-Time PCR System (Applied Biosystems) using Power SYBR Green Master Mix (Applied Biosystems) and primers 5'-GCGTGCAGTGGACCATTTTTCAGATTTA-3' (SEQ ID NO.: 85) and 5'-GCGTGCAGATCGAGCGTTTATC-CATTTG-3' (SEQ ID NO.: 77) for utrophin or 5'-GGGCAT-CACCACGAAAATCTC-3' (SEQ ID NO.: 78) and 5'-CTGCCGTTGTCAAACACCT-3' (SEQ ID NO.: 79) for RPLP0. Data was analyzed on QuantStudio Design & Analysis Software (Applied Biosystems). Expression levels of Utrophin mRNAs were normalized to the endogenous control RPLP0 using AACt method.

Immunofluorescence Analysis

Immunofluorescence staining of utrophin was performed on TA cryosections. Frozen sections (10 m thick) were blocked for 1 hr in PBS containing 3% BSA and 0.05% Triton-X100, followed by 1 hr incubation with specific primary antibody rabbit anti-utrophin polyclonal antibody (1:200) (C-19 sc-7459; Santa Cruz Biotechnology, Inc.) in PBS containing 2% goat serum. After three PBS washes, sections were incubated for 1 hr with secondary antibody. For secondary staining, goat Alexa-594 anti-rabbit (1:1000) (R37117; Molecular Probes, Inc.) with α-Bungarotoxin (α-BTX), Alexa Fluor 488 conjugate (1:500) (B-13422; Molecular Probes, Inc.) were used. Control tissue sections were processed simultaneously in the same manner. Slides were rinsed three times for 5 min in PBS and mounted in ProLong Gold Antifade Mountant (P36930; Molecular Probes, Inc.). The fluorescence digital images were acquired using an Olympus BX51 microscope at an objective magnification of ×20 and Olympus DP12 digital camera.

Muscle Histology and Morphology

Frozen muscle 10 μm sections were cut at the mid belly of TA and diaphragm. Sections were fixed in ice-cold methanol for 5 min and then processed for histological examination by H&E staining. The entire muscle section was imaged and analyzed. The single-fiber area distributions and total number of fibers were determined for each muscle from digital images acquired using an Olympus BX51 microscope at an objective magnification of ×10 and Olympus DP12 digital camera and software. Morphometric measurements (i.e., centrally nucleated fiber, single-fiber minimal Feret's diameter) were made using the Image J image-processing software (rsbweb.nih.gov/ij). Minimal Feret's diameter values for each muscle section were plotted as a frequency histogram. Calculation of variance coefficients of the minimal Feret's diameter was calculated as described by Briguet et. al.

Serum CK Quantification

Fresh, un-hemolysed serum was isolated from blood samples. Serum CK was measured with the indirect colorimetric Creatine Kinase-SL Assay kit (Genzyme Diagnostics P.E.I. Inc., Charlottetown, Canada) according to the manufacturer's instructions.

Hydroxyproline Content

The content of the amino acid hydroxyproline has been used as a measure of the extent of fibrosis in dystrophic skeletal muscle. Hydroxyproline assay was performed as described. The TA muscle and the diaphragm were used for hydroxyproline quantification assay.

Statistical Analysis

Data were analyzed using the GraphPad Prism v5 statistical software package (GraphPad Software, La Jolla, Calif.). Data are reported as means±SD. F-test was performed to test equality of variance between populations/groups. For statistical significance Mann-Whitney U test, the 2-way analysis of variance (ANOVA) with a Bonferroni correction or Tukey's multiple comparison tests with statistical significance set at $P \leq 0.05$ was performed. Appropriate statistical tests have been mentioned in figure legends.

Results

Figure 45:
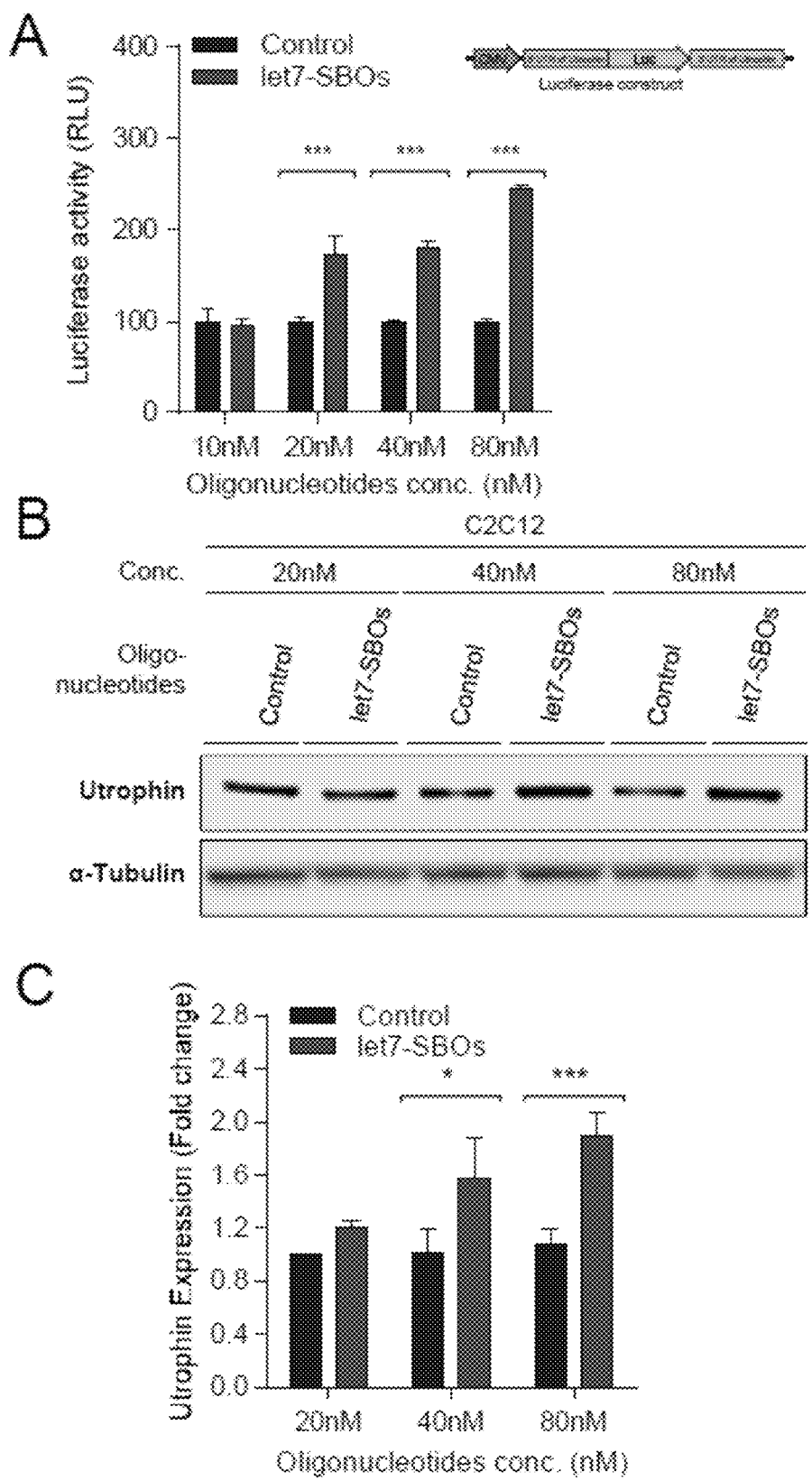
FIG. 45. Therapeutic strategy for utrophin upregulation validation in C2C12 cells. (A) Efficacy of let7-SBOs in C2C12-5'Luc3' utrophin reporter cells (cell line contains construct pGL4:50-5'Luc3' where reporter luciferase2 gene is flanked by the 5'- and 3'-UTRs of mouse utrophin-A). Cells transiently transfected with let7-SBOs/control oligonucleotides and luciferase activity measured 24 hrs post-transfection. Results shows significant increase in luciferase activity in C2C12-5'Luc3' utrophin reporter cells 24 hrs of post-transfection with let7-SBOs compared to control oligonucleotides at various concentrations. Bars represent mean±SD from 3 independent experiments. Statistical analysis was performed by 2-way ANOVA for multiple comparison followed by Bonferroni correction (***P≤0.001). (B) Endogenous utrophin protein expression in C2C12 cells 24 hrs after transfection with let7-SBOs or control oligonucleotides at various concentrations, assayed by western blotting. α-Tubulin staining was used to control for equal loading. (C) Quantification of utrophin normalized to α-tubulin band density in western blot assay. Bars represent mean±SD from 3 independent experiments and control. Control oligonucleotides treatment used as reference for utrophin expression in each independent experiment. Statistical analysis was performed by 2-way ANOVA for multiple comparison followed by Bonferroni correction (*P≤0.05, ***P≤0.001).
Figure 50:
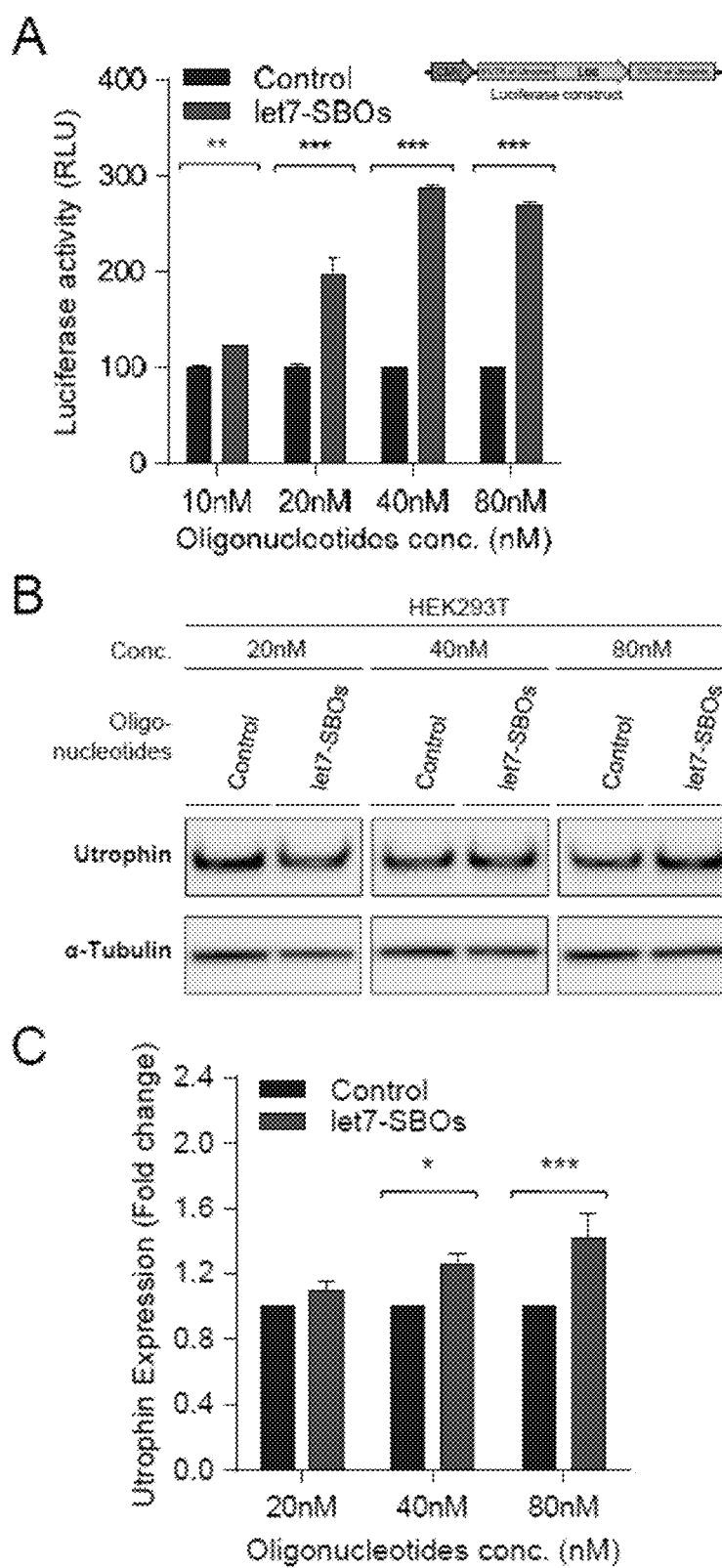
FIG. 50: Efficacy of let7-SBOs in human HEK293T cells. (A) HEK293 cells transiently transfected with firefly luciferase reporter construct pGL4:50-5'Luc3'Hu (the reporter luciferase2 gene is flanked by the 5'- and 3'-UTRs of human utrophin-A) and let7-SBOs/control oligonucleotides. Figure shows luciferase activity in HEK293T cells 24 hrs after transfection with let7-SBOs compared to control oligonucleotides at various concentrations. Bars represent mean±SD from 3 independent experiments. Statistical analysis was performed by 2-way ANOVA for multiple comparison followed by Bonferroni correction, P≤0.01, *P≤0.001. (B) Endogenous utrophin protein expression in HEK293T cells after 24 hrs of transient transfection with let7-SBOs or control oligonucleotides at different concentrations was assayed by western blotting. (C) Quantification of utrophin band density normalized to α-tubulin band density in western blot assay. Bars represent mean±SD from 3 independent experiments. Statistical analysis was performed by 2-way ANOVA for multiple comparison followed by Bonferroni correction (P≤0.05, ***P≤0.001).

To validate the blocking strategy, let7-SBOs was transiently transfected into mouse C2C12-5'Luc3' utrophin reporter cells, obtaining increased luciferase activity in a dose dependent manner (FIG. 45A). Increased endogenous utrophin expression was also noted in C2C12 cells after let7-SBOs transfection at different concentrations (FIGS. 45B and 45C). The let7-SBOs treatment in human HEK293T cells also showed increase in luciferase activity as well as utrophin expression, demonstrating the applicability of this approach across species (FIG. 50). We also validated the specificity of let7-SBOs and requirement of the let-7c site in the utrophin 3'UTR for increasing utrophin expression. We developed a reporter construct (pGL3-5'Luc3'-Δlet7) in which the let-7c binding site in the utrophin 3'UTR region was deleted using site directed mutagenesis. Luciferase assays after 24 hrs of transient transfection of pGL3-5'Luc3'-Δlet7 construct with control and let7-SBOs, in C2C12 cells showed no difference in luciferase activity compared to upregulation noted using the pGL3-5'Luc3' construct (FIG. 51). For an in vivo proof-of-principle, a single dose of 20 μg let7-SBOs and unrelated control oligonucleotides was injected in tibialis anterior (TA) muscles of 1 month old male mdx mice. After 1 month, we observed c.a. 1.9-fold utrophin overexpression (FIG. 52).

Figure 47:
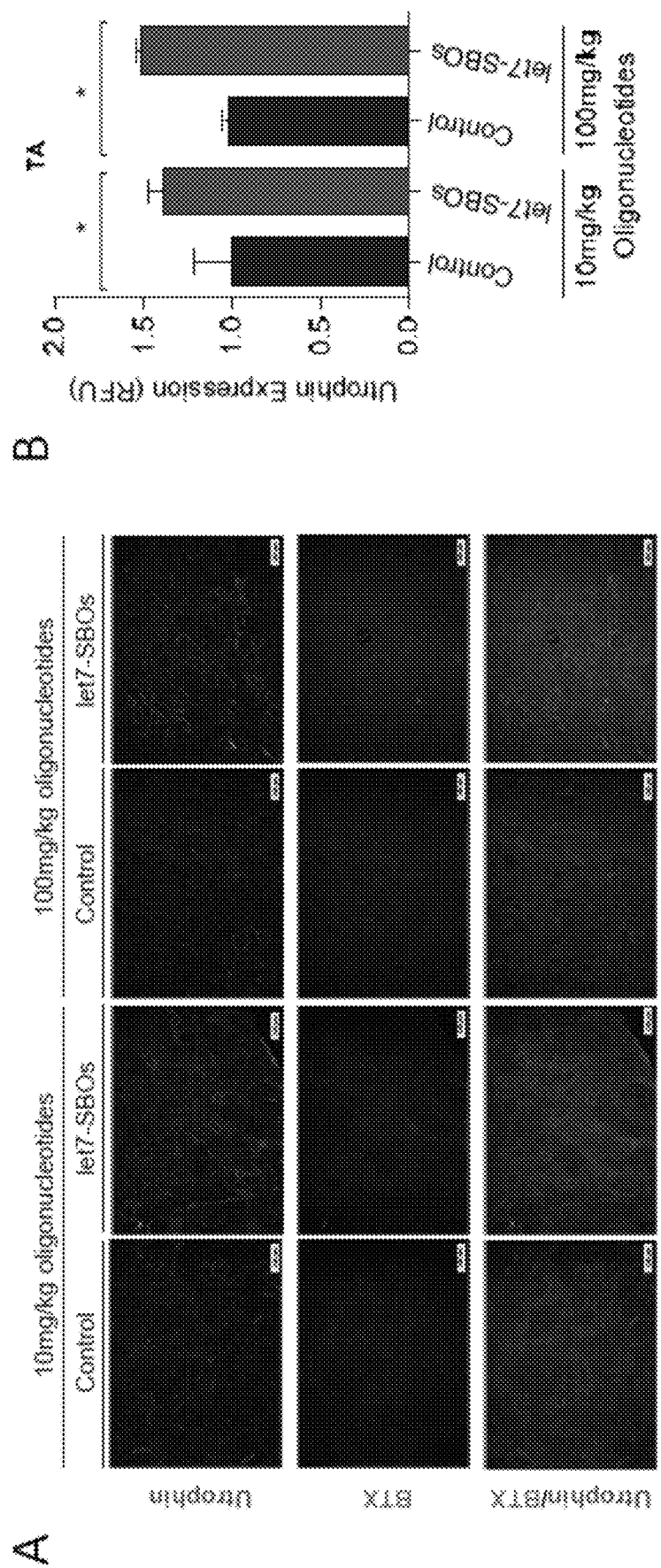
FIG. 47: Utrophin expression in TA muscle of mdx mice treated with intraperitoneal injection of let7-SBOs. (A) Expression and localization of utrophin in mdx mice treated with let7-SBOs. Frozen sections of the TA muscles immuno-labelled with anti-utrophin antibodies and α-BTX. Utrophin is restricted to the neuromuscular junctions in control muscles as revealed by utrophin and BTX staining however in let7-SBOs treated TA muscles utrophin was also expressed on the sarcolemma of muscle fibers. (Scale bar=100 μm). (B) Relative fluorescence quantification of utrophin expression in TA muscles with low and high dose let7-SBOs treatment compared with control oligonucleotides. Frozen 10 m thick sections of the TA muscles immuno-labelled with utrophin antibodies. Bars represent mean±SD (n=3 mice per experimental group). Statistical comparison was analyzed by Mann-Whitney U test (*P≤0.05).
Figure 49:
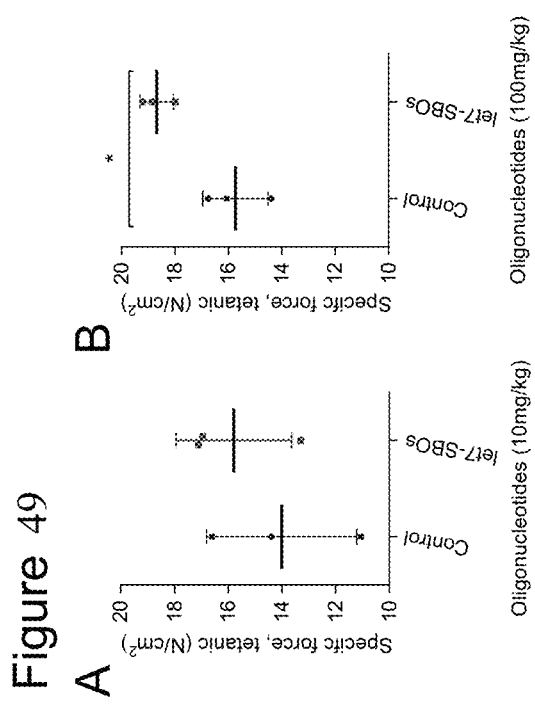
FIG. 49: Physiological analysis of EDL muscles from mdx mice treated with the intraperitoneal injections of let7-SBOs. (A) Normalized (specific) tetanic force of EDL with low dose let7-SBOs (n=3) treatment compared with control oligonucleotides (n=3). Significant differences were assessed by Mann-Whitney U test (*P≤0.05). (B) Normalized (specific) tetanic force of EDL with high dose let7-SBOs (n=3) treatment compared with control oligonucleotides (n=3). Significant differences were assessed by Mann-Whitney U test (*P≤0.05). Scatter dot plot represent mean±SD.
Figure 53:
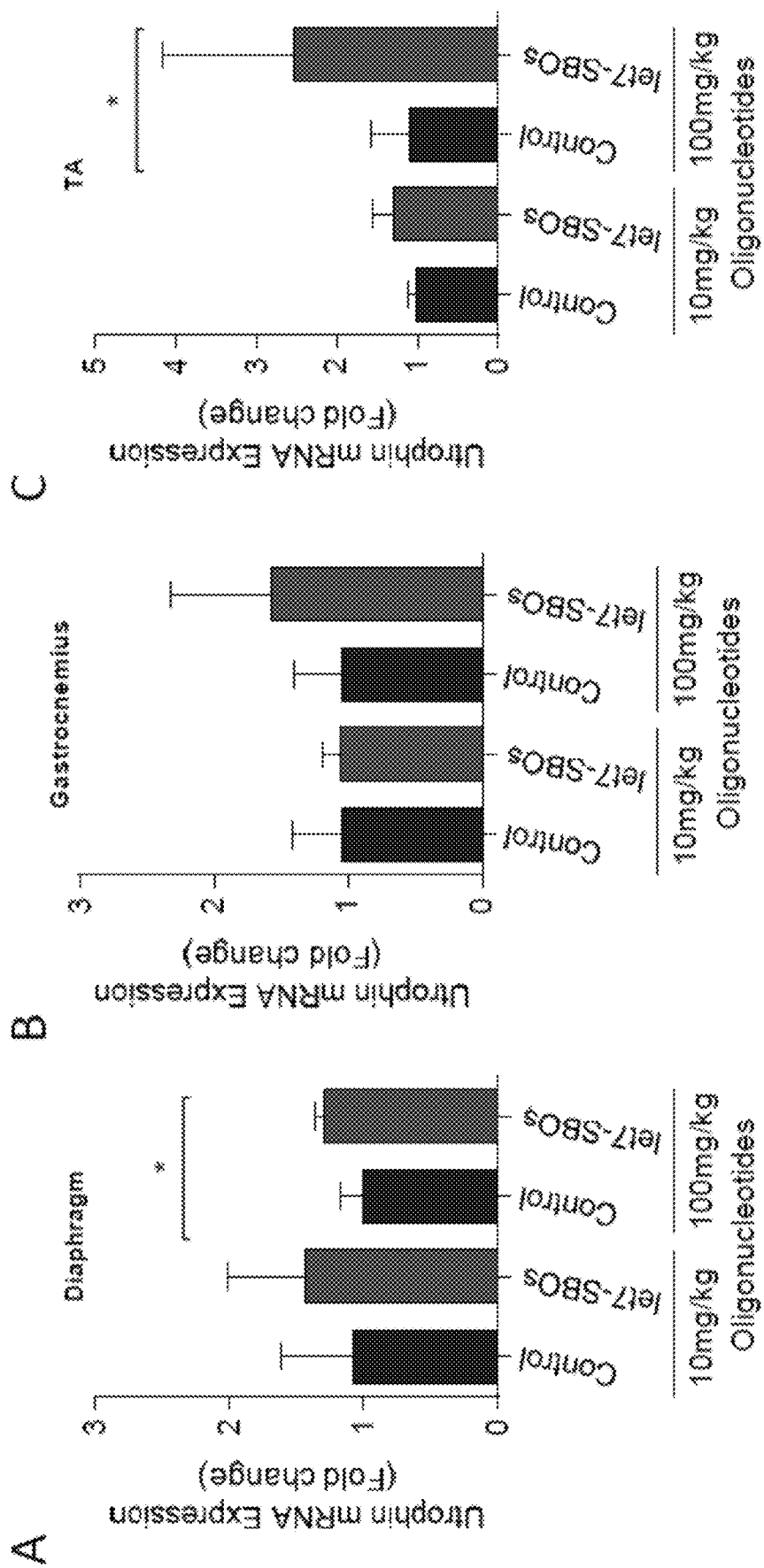
FIG. 53: Transcriptional expression of utrophin in TA muscle of mdx mice treated with intraperitoneal injection of let7-SBOs. (A-C) Utrophin mRNA expression by RT-qPCR in diaphragm (A), gastrocnemius (B) and TA (C) muscles of mdx mice (n=3 per group) with intramuscular injection of let7-SBOs and control oligonucleotides. RPLP0 was used as housekeeping gene. Bars represent mean±SD (n=3 mice per experimental group). Statistical comparison was analyzed by Mann-Whitney U test (P≤0.05).
Figure 54:
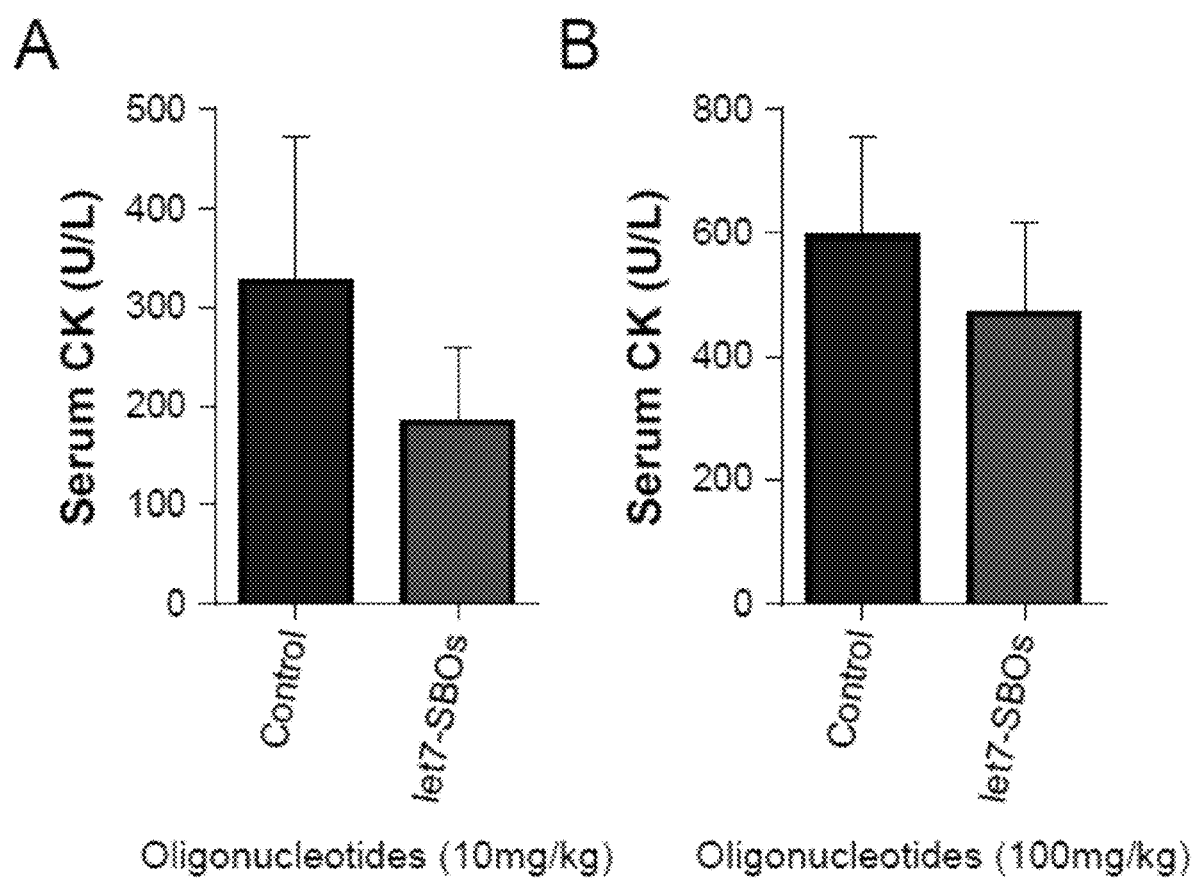
FIG. 54: Effect of let7-SBOs treatment in serum CK activity. Decrease in serum CK activity in mdx mice treated with the low dose (A) and high dose (B) of let7-SBOs compared to control oligonucleotides injected mdx mice. Scatter dot plot represent means±SD (n=3 in each group).

To test the ability of let7-SBOs treatment to improve the dystrophic phenotype and obtain proof-of-concept in vivo, 1 month old male mdx mice were injected bi-weekly with intraperitoneal injection of let7-SBOs and control oligonucleotides at two different doses (low dose 10 mg/kg and high dose 100 mg/kg) for 1 month. After a month of treatment mice were sacrificed and analyzed by morphological, biochemical and physiological means. We observed c.a. 1.4- and 1.8-fold increase of utrophin expression in diaphragm (FIGS. 46A and 46B), 1.3 and 1.7-fold increase in the gastrocnemius muscle (FIGS. 46C and 46D) and 2.1- and 3.2-fold increase in the TA muscle (FIGS. 46E and 46F) of both low and high dose let7-SBOs treatment compared to control oligonucleotides groups by western blot analysis. We also measured level of utrophin mRNA expression in diaphragm, gastrocnemius and TA muscles (FIG. 53) and observed significant increase in utrophin mRNA expression in diaphragm (c.a. 1.3-fold) and TA muscles (c.a. 2.5-fold) of high dose let7-SBOs treatment. Utrophin is enriched at the neuromuscular junction and myotendinous junction in adult skeletal muscle cells and extends the entire sarcolemma in developing and regenerating muscle. Immunofluorescence labeling for utrophin showed c.a. 1.4 (low dose) and 1.5-fold (high dose) increased utrophin at extrasynaptic sarcolemma of fibers in the TA muscles of let7-SBOs treated mdx mice compared to controls (FIGS. 47A and 47B). Morphologically, dystrophic muscles typically show a higher percentage of centrally nucleated fibers (CNF's). We observed significant reduction in the number of CNF's in TA (c.a. 11% and 14% reduction) and extensor digitorum longus (EDL) muscles (c.a. 9% and 7% reduction) in the low and high dose let7-SBOs treated mice, compared to controls (FIGS. 48A and 48B). Morphometric analyses of EDL muscles revealed a decrease in the variance coefficient of the minimal Feret's diameter in the low dose regimen (FIGS. 48C and 48D), indicating a decrease fiber heterogeneity and suggesting an improvement in dystrophic pathology. Details of these measurements and other morphometric parameters of measured are provided in Table 1. We next examined whether the dystrophic histopathology was improved by let7-SBOs treatment. Histological analysis showed a reduction in pathophysiological changes such as necrosis and cellular infiltration in diaphragm (FIG. 48E) and TA (FIG. 48F) muscles from treated mdx mice compared to controls in both low and high dose regimens. To determine whether the improvement in morphology was associated with biochemical improvement, we analyzed the hydroxyproline content of muscles as a biochemical marker for fibrosis. A significant reduction of hydroxyproline was found in the diaphragm (FIG. 48G) and TAs (FIG. 48H) of mdx mice treated with high dose of let7-SBOs compared to controls. No significant decrease in serum creatine kinase (CK) was noted (FIG. 54). To quantify functional improvement, we analyzed physiological properties of EDL muscle (Table 1). EDL muscles from high dose let7-SBOs treated mice showed increased specific strength compared to controls (Table 1). No changes were noted in post eccentric lengthening contraction (ECC) force drop (FIG. 55). Finally, we performed western assay for other let-7 target genes (e.g. c-Myc, Stat3, Jak3 etc.) to test our blocking strategy is comparatively specific for utrophin, and we have not observed any change in expression of these let-7 target genes (FIG. 56).

TABLE 1

Comparison of morphological and physiological properties of EDL muscle

| | 10 mg/kg dose | | 100 mg/kg dose | |
| --- | --- | --- | --- | --- |
| | Control oligonucleotides | let7-SBOs | Control oligonucleotides | let7-SBOs |
| Weight (mg) | 14.5 ± 1.0 (3) | 14.5 ± 2.4 (3) | 15.4 ± 0.5 (3) | 12.2 ± 0.6** (3) |
| CSA (mm$^2$) | 2.5 ± 0.2 (3) | 2.4 ± 0.4 (3) | 2.5 ± 0.1 (3) | 2.1 ± 0.1** (3) |
| Absolute force (mN) | 352.5 ± 56.7 (3) | 382.4 ± 81.6 (3) | 395.5 ± 13.6 (3) | 392.8 ± 17.3 (3) |
| Specific force (N cm$^{-2}$) | 14.0 ± 2.8 (3) | 15.8 ± 2.2 (3) | 15.8 ± 1.2 (3) | 18.7 ± 0.6* (3) |
| ECC force decrease (1-5) (%) | 36.3 ± 5.7 (3) | 40.2 ± 0.4 (3) | 51.5 ± 18.0 (3) | 44.1 ± 10.7 (3) |
| ECC force drop (5$^{th}$) (%) | 63.7 ± 5.7 (3) | 59.8 ± 0.4 (3) | 48.5 ± 18.0 (3) | 55.9 ± 10.7 (3) |
| Avg. of Minimal Feret's diameter (μM) | 32.01 ± 15.9 (1521) | 32.24 ± 13.8 (2046) | 30.6 ± 15.4 (1174) | 35.5 ± 16.2*** (1232) |
| Variance coefficient of Min. Feret's diameter | 499.5 ± 24.2 (3) | 431.3 ± 11.4* (3) | 489.4 ± 16.1 (3) | 444.0 ± 26.1 (3) |

Results are represented as mean ± SD; numbers in parentheses are n; asterisks, each dose of let7-SBOs treatment group compared with respective dose of control oligonucleotides and statistical significance was analyzed by Mann-Whitney U test (*P ≤ 0.05, P ≤ 0.01, *P ≤ 0.001). CSA, cross-sectional area.

In sum, the functional improvement of dystrophic muscle achieved using let7-SBOs demonstrates a novel utrophin upregulation-based therapeutic strategy for DMD.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A pharmaceutical composition comprising an antisense oligonucleotide that specifically hybridizes to a Let-7c microRNA binding sequence in a 3'-UTR of a utrophin mRNA 3' untranslated region (UTR) and inhibits the binding of the Let-7c microRNA to the utrophin mRNA 3'-UTR and at least one pharmaceutically acceptable excipient, wherein the antisense oligonucleotide is present in an amount effective in a human subject to inhibit the binding of Let-7 micro RNA with its utrophin mRNA 3'-UTR binding sequence, and wherein the antisense oligonucleotide comprises the sequence of SEQ ID NO: 25 (5'-CUG AGG UAG AAA GGU GGU CAU GGC UU-3').

2. The composition of claim 1, wherein the antisense oligonucleotide is a 2'-0-methyl phosphorothioate oligonucleotide.

3. The composition of claim 1, wherein the composition is formulated for injection to the subject.

4. The composition of claim 1, wherein the composition is formulated for intramuscular administration to the subject.

5. The composition of claim 1, further comprising at least one additional antisense oligonucleotide that specifically hybridizes to at least one additional microRNA binding sequence in the utrophin mRNA 3'-UTR and inhibits the binding of the at least one additional micro RNA to the utrophin mRNA 3'-UTR, wherein the additional micro RNA is selected from the group consisting of miR-133b, miR-150, miR-196b, miR-206, and miR-296-5p, and wherein the additional antisense oligonucleotide is present in an amount effective in a human subject to inhibit its binding with its corresponding utrophin mRNA 3'-UTR binding sequence.

6. The composition of claim 1, wherein the antisense oligonucleotide is present in an amount effective in the human subject to increase basal levels of translation of utrophin in a muscle cell in the subject by about 1.1 fold or more.

* * * * *